(12) United States Patent
De Both et al.

(10) Patent No.: US 12,398,399 B2
(45) Date of Patent: Aug. 26, 2025

(54) SHOOT REGENERATION BY OVEREXPRESSION OF CHK GENES

(71) Applicant: Keygene N.V., Wageningen (NL)

(72) Inventors: Michiel Theodoor Jan De Both, Wageningen (NL); Rik Hubertus Martinus Op Den Camp, Wageningen (NL); Bjorn Alexander Kloosterman, Wageningen (NL); Bernarda Gerharda Johanna Fierens-Onstenk, Wageningen (NL)

(73) Assignee: Keygene N.V., Wageningen (NL)

( * ) Notice: Subject to any disclaimer, the term of this patent is extended or adjusted under 35 U.S.C. 154(b) by 174 days.

(21) Appl. No.: 17/062,221

(22) Filed: Oct. 2, 2020

(65) Prior Publication Data

US 2021/0079415 A1 Mar. 18, 2021

Related U.S. Application Data

(63) Continuation of application No. PCT/EP2019/058614, filed on Apr. 5, 2019.

(30) Foreign Application Priority Data

Apr. 5, 2018 (EP) .................................. 18165895

(51) Int. Cl.
*C12N 15/82* (2006.01)

(52) U.S. Cl.
CPC ..... *C12N 15/8262* (2013.01); *C12N 15/8295* (2013.01)

(58) Field of Classification Search
None
See application file for complete search history.

(56) References Cited

U.S. PATENT DOCUMENTS

| 7,026,530 B2* | 4/2006 | Benfey ................ C07K 14/415 536/23.6 |
| 9,127,073 B2* | 9/2015 | Schmulling .......... C07K 14/415 |
| 2006/0185030 A1* | 8/2006 | Sheen .................. C07K 14/415 800/278 |

FOREIGN PATENT DOCUMENTS

| EP | 2 272 862 A1 | 1/2011 | |
| WO | WO-02/099079 A2 | 12/2002 | |
| WO | WO-2006057832 A2 * | 6/2006 | ......... C12N 15/8295 |

OTHER PUBLICATIONS

Kim et al 2006 (PNAS 103:3, p. 814-819) (Year: 2006).*
Nishimura et al 2004 (The Plant Cell 16: p. 1365-77), "Histidine Kinase Homologs That Act as Cytokinin Receptors Possess Overlapping Functions in the Regulation of Shoot and Root Growth in *Arabidopsis*." (Year: 2004).*
Zuo et al 2002 (Current Opinions in Biotechnology 13: p. 173-80) "Marker-free transformation: increasing transformation frequency by the use of regeneration-promoting genes" (Year: 2002).*
Hwang et al 2001 (Nature 413: p. 383-389) (Year: 2001).*
Debnath 2005 (HortScience 40(1): p. 189-192) (Year: 2005).*
International Search Report issued in PCT/EP2019/058614 dated May 24, 2019, 5 pages.
Riefler, Michael, et al., "*Arabidopsis* Cytokinin Receptor Mutants Reveal Functions in Shoot Growth, Leaf Senescence, Seed Size, Germination, Root Development, and Cytokinin Metabolism," The Plant Cell, vol. 18(1), Jan. 2006, pp. 40-54, XP-002362525.
Banno et al., "Overexpression of *Arabidopsis* ESR1 Induces Initiation of Shoot Regeneration", The Plant Cell, vol. 13, Dec. 2001, pp. 2609-2618 (10 pages).
Duclercq et al., "De novo shoot organogenesis: from art to science", Trends in Plant Science, vol. 16, No. 11, Nov. 2011 (10 pages).
Mok et al., "Cytokinin Metabolism and Action", Annu. Rev. Plant. Physiol. Plant Mol. Biol., vol. 52, 2001, pp. 89-118 (30 pages).
Quiroz-Figueroa et al., "Embryo production through somatic embryogenesis can be used to study cell differentiation in plants", Plant Cell Tiss Organ Cult, vol. 86, 2006, pp. 285-301 (17 pages).
Srinivasan et al., "Heterologous expression of the Baby Boom AP2/ERF transcription factor enhances the regeneration capacity of tobacco (*Nicotiana tabacum* L.)", Planta, vol. 225, 2007, pp. 341-351 (11 pages).
Hill et al., "Enhancing plant regeneration in tissue culture A molecular approach through manipulation of cytokinin sensitivity", Plant Signaling and Behavior, vol. 8(10), Oct. 2013, pp. 1-10.

* cited by examiner

*Primary Examiner* — Matthew R Keogh
(74) *Attorney, Agent, or Firm* — Sunit Talapatra; Foley & Lardner LLP

(57) ABSTRACT

Genetic modification of plants is hampered by the limited capacity of plant cells to regenerate. The current invention solves this problem by introducing or increasing the expression of a histidine kinase in a plant cell. Preferred histidine kinases are at least one of CHK2, CHK3 and CHK4. The invention therefore concerns a method for improving a cytokinin-induced regeneration capacity of a plant cell, wherein the method comprises a step of increasing or introducing the expression of a histidine kinase in the plant cell. The invention further pertains to a method for regenerating a plant, wherein the method comprises a step of introducing or increasing the expression of a histidine kinase and to a plant obtainable from such method. Moreover, the method concerns the use of at least one of CHK2, CHK3 and CHK4 for improving a cytokinin-induced regeneration capacity of a plant.

17 Claims, No Drawings

Specification includes a Sequence Listing.

SEQUENCE LISTING

<160> NUMBER OF SEQ ID NOS: 32

<210> SEQ ID NO 1
<211> LENGTH: 3531
<212> TYPE: DNA
<213> ORGANISM: Arabidopsis thaliana

<400> SEQUENCE: 1

```
atgtctataa cttgtgagct cttgaatctt acttcaaaga aagctaagaa gtcgtcgagc      60
agtgacaaga aatggctaaa gaagcctctc ttcttcctga ttttgtgtgg ctctttggta     120
attgttttgg ttatgttctt acggttaggt agaagtcaga aggaggagac agattcttgt     180
aatggagaag agaaagtgtt gtatagacat caaaatgtca caagaagtga gattcatgat     240
ttggtctctt tgttctctga ttcagatcag gtaacatcct ttgaatgtca taaggaatca     300
agccctggaa tgtggacaaa ctatggtatt acatgttccc tgagtgtgcg ttctgataaa     360
caagagacta gagggcttcc ctggaatctt ggcttaggac attctatctc atcaacatct     420
tgtatgtgtg gtaatcttga accgatttta cagcaacctg aaaaccttga ggaagaaaac     480
catgaagaag ggctggagca gggtttgtca tcgtatttaa gaaatgcatg gtggtgtcta     540
atccttggtg tgttagtgtg ccataagatt tatgtatctc attctaaagc acgaggtgag     600
aggaaagaga aagtacatct gcaagaggct ttagctccaa agaagcagca acaacgtgct     660
cagacttctt ctagaggggc tggaagatgg aggaagaata tccttctcct tggtattta     720 ggaggagttt ccttctctgt ttggtggttt tgggacacta atgaggagat cataatgaaa     780
aggagggaga ctttggcaaa catgtgtgac gaacgagcac gtgttttaca agatcagttc     840
aatgttagct tgaaccatgt tcatgccttg tctattcttg tatctacatt tcatcatggt     900
aaaatcccat ctgccattga tcagagaaca tttgaagaat atactgagag aacaaacttt     960
gagaggccac ttactagtgg tgtagcgtat gctttgaaag tcccacactc agaaagagag    1020
aaatttgaaa aggagcatgg atgggcaata aagaaaatgg aaactgagga ccagacagtt    1080
gtacaagatt gtgttcctga aaactttgat cccgcaccga ttcaagacga atacgcgcca    1140
gttatatttg ctcaagaaac tgtttcccat attgtatcgg tcgacatgat gtctggagaa    1200
gaagaccgtg aaaacatctt acgggcaagg gcatcaggaa aaggagtgtt aacatctcca    1260
tttaagcttc ttaagtcaaa tcatcttggt gttgtgttga cctttgctgt ctatgacacg    1320
agcctaccgc ctgatgctac agaagaacag cgtgttgaag caactattgg gtaccttggt    1380
gcatcatatg atatgccatc gctggtggag aaacttcttc accaacttgc cagcaaacag    1440
acaattgctg tggatgttta cgacacaact aacacttcag gtctaataaa aatgtatggc    1500
tcagaaattg gggatataag tgagcagcat ataagtagcc ttgattttgg tgatccatca    1560
aggaaccatg agatgcattg caggtttaag cataaacttc ccattccctg gacagcgata    1620
```

| | |
|---|---|
| acaccgtcga tcttagttct ggttattact tttcttgttg gttatatttt atatgaagcc | 1680 |
| atcaaccgaa ttgcgacagt tgaagaggat tgtcagaaga tgagggaact caaagctcgt | 1740 |
| gctgaggccg ctgacattgc aaagtcacag ttcctagcaa ctgtttctca tgagatacgg | 1800 |
| actccgatga atggagtttt aggaatgctg aaaatgctga tggacaccga tcttgatgcg | 1860 |
| aagcagatgg actatgcgca aactgctcat ggcagtggga aggatcttac atcactaata | 1920 |
| aatgaggttc ttgatcaggc aaagattgaa tccggaaggc tcgagcttga aaatgtgcct | 1980 |
| tttgatatgc gttttattct tgataatgtt tcatctctcc tctctggcaa ggcaaatgaa | 2040 |
| aaaggaattg agttggccgt ttatgtttct agtcaagttc ctgatgttgt agtcggtgat | 2100 |
| ccgagtcggt tccggcagat cattacaaac ctggttggaa actcaatcaa attcacacag | 2160 |
| gaaaggggac acatatttat ctcagtgcac cttgcagatg aggtaaagga gcctcttact | 2220 |
| attgaagacg cagtgctaaa acagcgacta gctttaggat gcagcgagtc cggtgagaca | 2280 |
| gttagcgggt ttcctgcggt aaatgcatgg ggaagctgga agaatttcaa gacatgttac | 2340 |
| agtactgaga gtcagaattc tgatcaaatc aaattgctag ttacagtgga ggacactgga | 2400 |
| gttggcatac ctgtggatgc acaaggccga atcttcacac cttttatgca agccgacagt | 2460 |
| tccacatcgc ggacttatgg tggaactggc ataggtttga gtataagcaa acgtttggtt | 2520 |
| gaactcatgc aaggagagat ggggtttgtg agtgagcccg ggataggcag tactttttca | 2580 |
| tttactggag ttttcgggaa agcagaaaca aatacgtcga ttactaagct ggaacgattc | 2640 |
| gatctagcta ttcaggagtt tacaggattg agagcattag ttattgataa cagaaacatt | 2700 |
| agagcagagg tcaccaggta cgaacttcgg agactgggaa tatctgcaga cattgtttca | 2760 |
| agtctgagaa tggcatgcac ttgttgtatc agcaaattag aaaatttggc tatgattcta | 2820 |
| atagacaaag acgcctggaa caaggaagaa ttttcagtac ttgacgagtt gtttacccga | 2880 |
| agcaaagtaa cctttacaag agtcccaaag atttttcttt tggcaacttc tgcaactctt | 2940 |
| actgagcgca gtgagatgaa gtctactggt ctcatcgatg aggtggtgat aaagcctctt | 3000 |
| cggatgagtg tcttaatatg ttgcttgcaa gaaacccttg tcaatggcaa gaagaggcaa | 3060 |
| ccgaacagac agcgaagaaa tcttggacac ttgctaagag aaaaacagat tctggttgtg | 3120 |
| gatgataatc ttgtgaacag acgagttgca gaaggtgcac ttaagaaata tggagctatt | 3180 |
| gttacatgcg ttgagagtgg caaagctgca ttggcaatgc ttaagccgcc tcataacttc | 3240 |
| gatgcttgct tcatggatct ccagatgcct gaaatggatg gatttgaagc gacaaggaga | 3300 |
| gtccgtgagc tggagaggga aatcaataag aaaaatagctt ctggagaagt ttcagctgaa | 3360 |
| atgttctgta aatttagtag ttggcacgtc ccgatattag caatgacagc agatgttatt | 3420 |
| caggctactc atgaagaatg catgaaatgt ggaatggatg gttatgtatc aaaaccgttt | 3480 |
| gaagaggaag tgctctacac agcggtagca agattctttg aaccttgtta a | 3531 |

<210> SEQ ID NO 2
<211> LENGTH: 3111
<212> TYPE: DNA
<213> ORGANISM: Arabidopsis thaliana

<400> SEQUENCE: 2

| | |
|---|---|
| atgagtctgt tccatgtgct agggtttggt gtcaagattg gcatctctt ctggatgcta | 60 |
| tgctgctggt ttgtttcttg gttcgttgat aatgggatcg aggacaagtc tggtctttta | 120 |
| gttggctctg tcggtgatct tgagaagact aagatgacta cgttgaagaa gaagaacaag | 180 |
| atgtggttct ggaataagat ctctagcagc ggactcaaga tcccgagttt ctcttatcag | 240 |

```
tttcttggct ctgttaaatt caacaaggcg tggtggagga agcttgtggt ggtttgggtt      300
gtcttctggg tcttggtctc tatttggacg ttttggtact ttagctcgca agctatggag      360
aagaggaaag agacgctagc tagtatgtgt gatgagagag ctcgtatgct gcaggatcag      420
ttcaacgtta gcatgaatca tgttcaagcc atgtctatct tgatctcaac cttccaccat      480
ggcaagattc cttctgctat cgatcagaga acattctcag agtacactga tagaacttcc      540
tttgagaggc ctcttactag cggggtagct tatgctatga gggtgctcca ttcagagagg      600
gaagagttcg agaggcaaca aggttggact attaggaaga tgtattctct gaacaaaac       660 ccagttcaca aggatgacta tgacctggaa gctttggaac catcccctgt ccaagaagag      720
tacgctccag tcatctttgc tcaggacact gtttctcacg ttgtttctct cgatatgctg      780
tctgggaaag aagatcgtga aaacgttttg cgggccagga gttcaggtaa aggggttttg      840
acagctcctt tcccattgat aaagacaaat agacttgggg tgatcctgac atttgcagtg      900
tacaagagag atctcccctc caatgcaacg ccaaaagaga gaattgaggc tactaacggg      960
tatctcgggg gagtgtttga cattgagtcc ctggtagaaa acttgcttca acagctggct     1020
agcaagcaaa cgattcttgt caatgtgtac gatatcacca atcactctca accgattagc     1080
atgtatggta caaatgtgtc ggctgatggg ttggaacgtg ttagtccact aatctttggc     1140
gatccattga gaaagcatga gatgcgttgc agatttaagc agaaaccacc atggccagtg     1200
ctatcaatgg tgacatcatt cggtatcctt gtgattgcgt tacttgttgc acatataatc     1260
cacgcaaccg ttagtcgaat acacaaagtt gaagaagatt gtgataaaat gaagcagctc     1320
aagaaaaagg ctgaagcagc agatgttgca aagtcacagt tccttgccac tgtttcacat     1380
gaaatcagaa ctccaatgaa tggtgttcta ggaatgttgc atatgcttat ggacacagag     1440
ttagatgtta cgcaacagga ttatgttagg accgcacagg caagtggaaa agctttagtc     1500
tcgctaataa atgaggtttt ggaccaagca aagattgaat ctggaaagct tgaacttgag     1560
gaggtgcggt ttgatttgag aggaatatta gatgatgtcc tgtcactctt ctctagcaag     1620
tcccaacaaa aggggggtgga gttggcagta tacatatctg atcgtgttcc agatatgtta     1680
attggtgatc ctgggaggtt tcgacaaata ctcacaaatc ttatgggtaa ttccattaag     1740
ttcactgaga aaggacacat cttttgtaact gttcatttgg tggatgagct attttgaatct     1800 atcgatggag agacagcatc atctccggaa agtacactga gtgggcttcc agttgcagac     1860
cggcagagga gctgggaaaa ctttaaagct ttcagctcca acgggcatcg gagctttgaa     1920
ccatctcccc ctgatataaa cctaatcgtc tcagttgagg atactggcgt agggatccct     1980
gtagaagcgc agtcccgtat ttttacgcct ttcatgcaag tcggaccatc catatccagg     2040
acgcatggag gcacaggaat tggacttagc ataagcaaat gtctagttgg actgatgaag     2100
ggagaaattg gattctcgag tactcccaag gttgggtcca cattcacatt tactgctgta     2160
ttttccaatg ggatgcaacc agctgaaaga aagaatgaca caaccagcc catattctcg       2220 gaattccggg gcatgaaagc tgtggttgtg gaccataggc ctgcaagggc aaaagtctcg     2280
tggtaccatt tcagcgtcct tggaattcga gtcgaagtag ttccacgtgt tgaacaggct     2340
ctacattatc tgaagattgg tactaccact gtgaatatga tactcataga gcaagaaata     2400 tggaatagg aagcagatga tttcattaaa aagctacaga aagaccctct tttcctttct       2460
cctaagttga ttttgttagc aaactcagta gaatcgtcaa tatcagaggc tttatgcacc     2520
ggtatagatc ctccaatagt gatagtgaaa ccattgaggg cgagtatgct agcagcaact     2580
```

| | |
|---|---:|
| ttgcagaggg gattgggtat tggaatcaga gaaccacctc aacacaaggg acctcctgct | 2640 |
| ttgattctca ggaatcttct ccttggtaga aaaattttaa tcgtggatga taacaacgta | 2700 |
| aacctcagag tggcagcggg agctctgaaa aagtacggag ctgatgtggt ctgcgctgag | 2760 |
| agtgggataa aggcaatctc attgcttaag ccacctcacg agtttgatgc ttgcttcatg | 2820 |
| gacattcaga tgccagaaat ggatggattt gaagctacaa ggagaatacg agatatggaa | 2880 |
| gaggagatga acaagagaat aaagaatggg gaggctttga tagtagagaa cggtaacaaa | 2940 |
| acaagctggc atcttccggt attagcaatg acggcagatg tgatccaagc aacgcatgag | 3000 |
| gaatgtctga agtgtggaat ggatgggtat gtatcaaaac catttgaagc agagcagctg | 3060 |
| tacagggaag tttctcgctt tttcaattcg ccttcagata cagaatcata a | 3111 |

<210> SEQ ID NO 3
<211> LENGTH: 3243
<212> TYPE: DNA
<213> ORGANISM: Arabidopsis thaliana

<400> SEQUENCE: 3

| | |
|---|---:|
| atgagaagag attttgtgta taataataat gcaatgttca atcctctcac aactcattac | 60 |
| agctcagata tgaactgggc actcaacaat catcaagaag aagaagaaga gccacgaaga | 120 |
| attgaaattt ctgattccga gtcactagaa aacttgaaaa gcagcgattt ttatcaactg | 180 |
| ggtggtggtg gtgctctgaa ttcgtcagaa aagccgagaa gatcgatttt ttggcgttcg | 240 |
| gggttgatgg gttttgcgaa gatgcagcag cagcaacagc ttcagcattc agtggcggtg | 300 |
| aagatgaaca taataataa taacgatcta atgggtaata aaaaagggtc aactttcata | 360 |
| caagaacatc gagcattgtt accaaaagct tgattctgt ggatcatcat tgttgggttt | 420 |
| ataagcagtg ggatttatca gtggatggat gatgctaata agattagaag ggaagaggtt | 480 |
| ttggtcagca tgtgtgatca aagagctaga atgttgcagg atcaatttag tgttagtgtt | 540 |
| aatcatgttc atgctttggc tattctcgtc tccactttc attaccacaa gaacccttct | 600 |
| gcaattgatc aggagacatt tgcggagtac acggcaagaa cagcatttga gagaccgttg | 660 |
| ctaagtggag tggcttatgc tgaaaaagtt gtgaattttg agaggagat gtttgagcgg | 720 |
| cagcacaatt gggttataaa gacaatggat agaggagagc cttcaccggt tagggatgag | 780 |
| tatgctcctg ttatattctc tcaagatagt gtctcttacc ttgagtcact cgatatgatg | 840 |
| tcaggcgagg aggatcgtga aatattttg cgagctagag aaaccggaaa agctgtcttg | 900 |
| actagccctt ttaggttgtt ggaaactcac catctcggag ttgtgttgac attccctgtc | 960 |
| tacaagtctt ctcttcctga aaatccgact gtcgaagagc gtattgcagc cactgcaggg | 1020 |
| taccttggtg gtgcgtttga tgtggagtct ctagtcgaga atttacttgg tcagcttgct | 1080 |
| ggtaaccaag caatagttgt gcatgtgtat gatatcacca atgcatcaga tccacttgtc | 1140 |
| atgtatggta atcaagatga agaagccgac agatctctct tcatgagag caagctcgat | 1200 |
| tttggagacc ccttcaggaa acataagatg atatgcaggt accaccaaaa ggcaccaata | 1260 |
| ccgttgaatg tgctcacaac tgtgccattg ttctttgcga ttggttttctt ggtgggttat | 1320 |
| atactgtatg gtgcagctat gcacatagta aaagtcgaag atgatttcca tgaaatgcaa | 1380 |
| gagcttaaag ttcgagcaga agctgctgat gtcgctaaat cgcagtttct tgctaccgtg | 1440 |
| tctcacgaga tcaggacacc aatgaatggc attctcggaa tgcttgctat gctcctagat | 1500 |
| acagaactaa gctcgacaca gagagattac gctcaaaccg ctcaagtatg tggtaaagct | 1560 |
| ttgattgcat tgataaatga ggttcttgat cgcgccaaga ttgaagctgg aaagctggag | 1620 |

```
ttggaatcag taccatttga tatccgttca atattggatg atgtcctttc tctattctct    1680
gaggagtcaa ggaacaaaag cattgagctc gcggttttcg tttcagacaa agtaccagag    1740
atagtcaaag gagattcagg gagatttaga cagataatca taaaccttgt tggaaattcg    1800
gttaaattca cagagaaagg acatatcttt gttaaagtcc atcttgcgga caatcaaaa    1860
gatgaatctg aaccgaaaaa tgcattgaat ggtggagtgt ctgaagaaat gatcgttgtt    1920
tccaaacagt caagttacaa cacattgagc ggttacgaag ctgctgatgg tcggaatagc    1980
tgggattcat tcaagcattt ggtctctgag gagcagtcat tatcggagtt tgatatttct    2040
agcaatgtta ggcttatggt ttcaatcgaa gacacgggta ttggaatccc tttagttgcg    2100
caaggccgtg tgtttatgcc gtttatgcaa gcagatagct cgacttcaag aaactatgga    2160
ggtactggta ttggtttgag tataagcaag tgtcttgttg aacttatgcg tggtcagata    2220
aatttcataa gccggcctca tattggaagc acgttctggt tcacggctgt tttagagaaa    2280
tgcgataaat gcagtgcgat taaccatatg aagaaaccta atgtggaaca cttgccttct    2340
acttttaaag gaatgaaagc tatagttgtt gatgctaagc ctgttagagc tgctgtgact    2400
agataccata tgaaaagact cggaatcaat gttgatgtcg tgacaagtct caaaaccgct    2460
gttgttgcag ctgctgcgtt tgaaagaaac ggttctcctc tcccaacaaa accgcaactt    2520
gatatgatct tagtagagaa agattcatgg atttcaactg aagataatga ctcagagatt    2580
cgtttattga attcaagaac caacggaaac gttcatcaca gtctccgaa actagctcta    2640
ttcgcaacaa acatcacaaa ttcggagttc gacagagcta atccgcagg atttgcagat    2700
acggtaataa tgaaaccgtt aagagcaagc atgattgggg cgtgtctgca acaagttctc    2760
gagctgagaa aaacaagaca acaacatcca gaaggatcat cacccgcaac tctcaagagc    2820
ttgcttacag ggaagaagat tcttgtggtt gatgataata tagttaacag gagagtagct    2880
gcaggagctc tcaagaaatt tggagcagaa gtggtttgtg cagagagtgg tcaagttgct    2940
ttgggtttgc ttcagattcc acacactttc gatgcttgct tcatggatat tcaaatgcca    3000
cagatggacg gatttgaagc aactcgtcag ataagaatga tggagaagga aactaaagag    3060
aagacaaatc tcgaatggca tttaccgatt ctagcgatga ctgcggatgt gatacacgcg    3120
acctacgagg aatgtctgaa aagtgggatg atggttacg tctccaaacc ttttgaagaa    3180
gagaatctct ataaatccgt tgccaaatca ttcaaaccta tcctatctc accttcgtcg    3240
taa                                                                  3243
```

<210> SEQ ID NO 4
<211> LENGTH: 1176
<212> TYPE: PRT
<213> ORGANISM: Arabidopsis thaliana

<400> SEQUENCE: 4

```
Met Ser Ile Thr Cys Glu Leu Leu Asn Leu Thr Ser Lys Lys Ala Lys
1               5                   10                  15

Lys Ser Ser Ser Asp Lys Lys Trp Leu Lys Lys Pro Leu Phe Phe
            20                  25                  30

Leu Ile Leu Cys Gly Ser Leu Val Ile Leu Val Met Phe Leu Arg
            35                  40                  45

Leu Gly Arg Ser Gln Lys Glu Glu Thr Asp Ser Cys Asn Gly Glu Glu
        50                  55                  60

Lys Val Leu Tyr Arg His Gln Asn Val Thr Arg Ser Glu Ile His Asp
65                  70                  75                  80
```

```
Leu Val Ser Leu Phe Ser Asp Ser Asp Gln Val Thr Ser Phe Glu Cys
                85                  90                  95

His Lys Glu Ser Ser Pro Gly Met Trp Thr Asn Tyr Gly Ile Thr Cys
            100                 105                 110

Ser Leu Ser Val Arg Ser Asp Lys Gln Glu Thr Arg Gly Leu Pro Trp
        115                 120                 125

Asn Leu Gly Leu Gly His Ser Ile Ser Ser Thr Ser Cys Met Cys Gly
    130                 135                 140

Asn Leu Glu Pro Ile Leu Gln Gln Pro Glu Asn Leu Glu Glu Glu Asn
145                 150                 155                 160

His Glu Glu Gly Leu Glu Gln Gly Leu Ser Ser Tyr Leu Arg Asn Ala
                165                 170                 175

Trp Trp Cys Leu Ile Leu Gly Val Leu Val Cys His Lys Ile Tyr Val
            180                 185                 190

Ser His Ser Lys Ala Arg Gly Glu Arg Lys Glu Lys Val His Leu Gln
        195                 200                 205

Glu Ala Leu Ala Pro Lys Lys Gln Gln Gln Arg Ala Gln Thr Ser Ser
    210                 215                 220

Arg Gly Ala Gly Arg Trp Arg Lys Asn Ile Leu Leu Leu Gly Ile Leu
225                 230                 235                 240

Gly Gly Val Ser Phe Ser Val Trp Trp Phe Trp Asp Thr Asn Glu Glu
                245                 250                 255

Ile Ile Met Lys Arg Arg Glu Thr Leu Ala Asn Met Cys Asp Glu Arg
            260                 265                 270

Ala Arg Val Leu Gln Asp Gln Phe Asn Val Ser Leu Asn His Val His
        275                 280                 285

Ala Leu Ser Ile Leu Val Ser Thr Phe His His Gly Lys Ile Pro Ser
    290                 295                 300

Ala Ile Asp Gln Arg Thr Phe Glu Glu Tyr Thr Glu Arg Thr Asn Phe
305                 310                 315                 320

Glu Arg Pro Leu Thr Ser Gly Val Ala Tyr Ala Leu Lys Val Pro His
                325                 330                 335

Ser Glu Arg Glu Lys Phe Glu Lys Glu His Gly Trp Ala Ile Lys Lys
            340                 345                 350

Met Glu Thr Glu Asp Gln Thr Val Val Gln Asp Cys Val Pro Glu Asn
        355                 360                 365

Phe Asp Pro Ala Pro Ile Gln Asp Glu Tyr Ala Pro Val Ile Phe Ala
    370                 375                 380

Gln Glu Thr Val Ser His Ile Val Ser Val Asp Met Met Ser Gly Glu
385                 390                 395                 400

Glu Asp Arg Glu Asn Ile Leu Arg Ala Arg Ala Ser Gly Lys Gly Val
                405                 410                 415

Leu Thr Ser Pro Phe Lys Leu Leu Lys Ser Asn His Leu Gly Val Val
            420                 425                 430

Leu Thr Phe Ala Val Tyr Asp Thr Ser Leu Pro Pro Asp Ala Thr Glu
        435                 440                 445

Glu Gln Arg Val Glu Ala Thr Ile Gly Tyr Leu Gly Ala Ser Tyr Asp
    450                 455                 460

Met Pro Ser Leu Val Glu Lys Leu Leu His Gln Leu Ala Ser Lys Gln
465                 470                 475                 480

Thr Ile Ala Val Asp Val Tyr Asp Thr Thr Asn Thr Ser Gly Leu Ile
                485                 490                 495
```

```
Lys Met Tyr Gly Ser Glu Ile Gly Asp Ile Ser Glu Gln His Ile Ser
            500                 505                 510

Ser Leu Asp Phe Gly Asp Pro Ser Arg Asn His Glu Met His Cys Arg
        515                 520                 525

Phe Lys His Lys Leu Pro Ile Pro Trp Thr Ala Ile Thr Pro Ser Ile
    530                 535                 540

Leu Val Leu Val Ile Thr Phe Leu Val Gly Tyr Ile Leu Tyr Glu Ala
545                 550                 555                 560

Ile Asn Arg Ile Ala Thr Val Glu Glu Asp Cys Gln Lys Met Arg Glu
                565                 570                 575

Leu Lys Ala Arg Ala Glu Ala Ala Asp Ile Ala Lys Ser Gln Phe Leu
            580                 585                 590

Ala Thr Val Ser His Glu Ile Arg Thr Pro Met Asn Gly Val Leu Gly
        595                 600                 605

Met Leu Lys Met Leu Met Asp Thr Asp Leu Asp Ala Lys Gln Met Asp
    610                 615                 620

Tyr Ala Gln Thr Ala His Gly Ser Gly Lys Asp Leu Thr Ser Leu Ile
625                 630                 635                 640

Asn Glu Val Leu Asp Gln Ala Lys Ile Glu Ser Gly Arg Leu Glu Leu
                645                 650                 655

Glu Asn Val Pro Phe Asp Met Arg Phe Ile Leu Asp Asn Val Ser Ser
            660                 665                 670

Leu Leu Ser Gly Lys Ala Asn Glu Lys Gly Ile Glu Leu Ala Val Tyr
        675                 680                 685

Val Ser Ser Gln Val Pro Asp Val Val Gly Asp Pro Ser Arg Phe
690                 695                 700

Arg Gln Ile Ile Thr Asn Leu Val Gly Asn Ser Ile Lys Phe Thr Gln
705                 710                 715                 720

Glu Arg Gly His Ile Phe Ile Ser Val His Leu Ala Asp Glu Val Lys
                725                 730                 735

Glu Pro Leu Thr Ile Glu Asp Ala Val Leu Lys Gln Arg Leu Ala Leu
            740                 745                 750

Gly Cys Ser Glu Ser Gly Glu Thr Val Ser Gly Phe Pro Ala Val Asn
        755                 760                 765

Ala Trp Gly Ser Trp Lys Asn Phe Lys Thr Cys Tyr Ser Thr Glu Ser
770                 775                 780

Gln Asn Ser Asp Gln Ile Lys Leu Leu Val Thr Val Glu Asp Thr Gly
785                 790                 795                 800

Val Gly Ile Pro Val Asp Ala Gln Gly Arg Ile Phe Thr Pro Phe Met
                805                 810                 815

Gln Ala Asp Ser Ser Thr Ser Arg Thr Tyr Gly Gly Thr Gly Ile Gly
            820                 825                 830

Leu Ser Ile Ser Lys Arg Leu Val Glu Leu Met Gln Gly Glu Met Gly
        835                 840                 845

Phe Val Ser Glu Pro Gly Ile Gly Ser Thr Phe Ser Phe Thr Gly Val
850                 855                 860

Phe Gly Lys Ala Glu Thr Asn Thr Ser Ile Thr Lys Leu Glu Arg Phe
865                 870                 875                 880

Asp Leu Ala Ile Gln Glu Phe Thr Gly Leu Arg Ala Leu Val Ile Asp
                885                 890                 895

Asn Arg Asn Ile Arg Ala Glu Val Thr Arg Tyr Glu Leu Arg Arg Leu
            900                 905                 910

Gly Ile Ser Ala Asp Ile Val Ser Ser Leu Arg Met Ala Cys Thr Cys
```

```
                    915                 920                 925
Cys Ile Ser Lys Leu Glu Asn Leu Ala Met Ile Leu Ile Asp Lys Asp
            930                 935                 940
Ala Trp Asn Lys Glu Glu Phe Ser Val Leu Asp Glu Leu Phe Thr Arg
945                 950                 955                 960
Ser Lys Val Thr Phe Thr Arg Val Pro Lys Ile Phe Leu Leu Ala Thr
                965                 970                 975
Ser Ala Thr Leu Thr Glu Arg Ser Glu Met Lys Ser Thr Gly Leu Ile
            980                 985                 990
Asp Glu Val Val Ile Lys Pro Leu Arg Met Ser Val Leu Ile Cys Cys
            995                 1000                1005
Leu Gln Glu Thr Leu Val Asn Gly Lys Lys Arg Gln Pro Asn Arg
        1010                1015                1020
Gln Arg Arg Asn Leu Gly His Leu Leu Arg Glu Lys Gln Ile Leu
        1025                1030                1035
Val Val Asp Asp Asn Leu Val Asn Arg Arg Val Ala Glu Gly Ala
        1040                1045                1050
Leu Lys Lys Tyr Gly Ala Ile Val Thr Cys Val Glu Ser Gly Lys
        1055                1060                1065
Ala Ala Leu Ala Met Leu Lys Pro Pro His Asn Phe Asp Ala Cys
        1070                1075                1080
Phe Met Asp Leu Gln Met Pro Glu Met Asp Gly Phe Glu Ala Thr
        1085                1090                1095
Arg Arg Val Arg Glu Leu Glu Arg Glu Ile Asn Lys Lys Ile Ala
        1100                1105                1110
Ser Gly Glu Val Ser Ala Glu Met Phe Cys Lys Phe Ser Ser Trp
        1115                1120                1125
His Val Pro Ile Leu Ala Met Thr Ala Asp Val Ile Gln Ala Thr
        1130                1135                1140
His Glu Glu Cys Met Lys Cys Gly Met Asp Gly Tyr Val Ser Lys
        1145                1150                1155
Pro Phe Glu Glu Glu Val Leu Tyr Thr Ala Val Ala Arg Phe Phe
        1160                1165                1170
Glu Pro Cys
        1175

<210> SEQ ID NO 5
<211> LENGTH: 1036
<212> TYPE: PRT
<213> ORGANISM: Arabidopsis thaliana

<400> SEQUENCE: 5

Met Ser Leu Phe His Val Leu Gly Phe Gly Val Lys Ile Gly His Leu
1               5                   10                  15

Phe Trp Met Leu Cys Cys Trp Phe Val Ser Trp Phe Val Asp Asn Gly
            20                  25                  30

Ile Glu Asp Lys Ser Gly Leu Leu Val Gly Ser Val Gly Asp Leu Glu
        35                  40                  45

Lys Thr Lys Met Thr Thr Leu Lys Lys Lys Asn Lys Met Trp Phe Trp
50                  55                  60

Asn Lys Ile Ser Ser Ser Gly Leu Lys Ile Pro Ser Phe Ser Tyr Gln
65                  70                  75                  80

Phe Leu Gly Ser Val Lys Phe Asn Lys Ala Trp Trp Arg Lys Leu Val
                85                  90                  95
```

```
Val Val Trp Val Val Phe Trp Val Leu Val Ser Ile Trp Thr Phe Trp
            100                 105                 110

Tyr Phe Ser Ser Gln Ala Met Glu Lys Arg Lys Glu Thr Leu Ala Ser
            115                 120                 125

Met Cys Asp Glu Arg Ala Arg Met Leu Gln Asp Gln Phe Asn Val Ser
            130                 135                 140

Met Asn His Val Gln Ala Met Ser Ile Leu Ile Ser Thr Phe His His
145                 150                 155                 160

Gly Lys Ile Pro Ser Ala Ile Asp Gln Arg Thr Phe Ser Glu Tyr Thr
            165                 170                 175

Asp Arg Thr Ser Phe Glu Arg Pro Leu Thr Ser Gly Val Ala Tyr Ala
            180                 185                 190

Met Arg Val Leu His Ser Glu Arg Glu Glu Phe Glu Arg Gln Gln Gly
            195                 200                 205

Trp Thr Ile Arg Lys Met Tyr Ser Leu Glu Gln Asn Pro Val His Lys
            210                 215                 220

Asp Asp Tyr Asp Leu Glu Ala Leu Glu Pro Ser Val Gln Glu Glu
225                 230                 235                 240

Tyr Ala Pro Val Ile Phe Ala Gln Asp Thr Val Ser His Val Val Ser
            245                 250                 255

Leu Asp Met Leu Ser Gly Lys Glu Asp Arg Glu Asn Val Leu Arg Ala
            260                 265                 270

Arg Ser Ser Gly Lys Gly Val Leu Thr Ala Pro Phe Pro Leu Ile Lys
            275                 280                 285

Thr Asn Arg Leu Gly Val Ile Leu Thr Phe Ala Val Tyr Lys Arg Asp
290                 295                 300

Leu Pro Ser Asn Ala Thr Pro Lys Glu Arg Ile Glu Ala Thr Asn Gly
305                 310                 315                 320

Tyr Leu Gly Gly Val Phe Asp Ile Glu Ser Leu Val Glu Asn Leu Leu
            325                 330                 335

Gln Gln Leu Ala Ser Lys Gln Thr Ile Leu Val Asn Val Tyr Asp Ile
            340                 345                 350

Thr Asn His Ser Gln Pro Ile Ser Met Tyr Gly Thr Asn Val Ser Ala
            355                 360                 365

Asp Gly Leu Glu Arg Val Ser Pro Leu Ile Phe Gly Asp Pro Leu Arg
            370                 375                 380

Lys His Glu Met Arg Cys Arg Phe Lys Gln Lys Pro Pro Trp Pro Val
385                 390                 395                 400

Leu Ser Met Val Thr Ser Phe Gly Ile Leu Val Ile Ala Leu Leu Val
            405                 410                 415

Ala His Ile Ile His Ala Thr Val Ser Arg Ile His Lys Val Glu Glu
            420                 425                 430

Asp Cys Asp Lys Met Lys Gln Leu Lys Lys Ala Glu Ala Ala Asp
            435                 440                 445

Val Ala Lys Ser Gln Phe Leu Ala Thr Val Ser His Glu Ile Arg Thr
            450                 455                 460

Pro Met Asn Gly Val Leu Gly Met Leu His Met Leu Met Asp Thr Glu
465                 470                 475                 480

Leu Asp Val Thr Gln Gln Asp Tyr Val Arg Thr Ala Gln Ala Ser Gly
            485                 490                 495

Lys Ala Leu Val Ser Leu Ile Asn Glu Val Leu Asp Gln Ala Lys Ile
            500                 505                 510

Glu Ser Gly Lys Leu Glu Leu Glu Glu Val Arg Phe Asp Leu Arg Gly
```

```
                515                 520                 525
Ile Leu Asp Asp Val Leu Ser Leu Phe Ser Lys Ser Gln Gln Lys
        530                 535                 540

Gly Val Glu Leu Ala Val Tyr Ile Ser Asp Arg Val Pro Asp Met Leu
545                 550                 555                 560

Ile Gly Asp Pro Gly Arg Phe Arg Gln Ile Leu Thr Asn Leu Met Gly
                565                 570                 575

Asn Ser Ile Lys Phe Thr Glu Lys Gly His Ile Phe Val Thr Val His
            580                 585                 590

Leu Val Asp Glu Leu Phe Glu Ser Ile Asp Gly Glu Thr Ala Ser Ser
        595                 600                 605

Pro Glu Ser Thr Leu Ser Gly Leu Pro Val Ala Asp Arg Gln Arg Ser
    610                 615                 620

Trp Glu Asn Phe Lys Ala Phe Ser Ser Asn Gly His Arg Ser Phe Glu
625                 630                 635                 640

Pro Ser Pro Pro Asp Ile Asn Leu Ile Val Ser Val Glu Asp Thr Gly
                645                 650                 655

Val Gly Ile Pro Val Glu Ala Gln Ser Arg Ile Phe Thr Pro Phe Met
            660                 665                 670

Gln Val Gly Pro Ser Ile Ser Arg Thr His Gly Gly Thr Gly Ile Gly
        675                 680                 685

Leu Ser Ile Ser Lys Cys Leu Val Gly Leu Met Lys Gly Glu Ile Gly
    690                 695                 700

Phe Ser Ser Thr Pro Lys Val Gly Ser Thr Phe Thr Phe Thr Ala Val
705                 710                 715                 720

Phe Ser Asn Gly Met Gln Pro Ala Glu Arg Lys Asn Asp Asn Asn Gln
                725                 730                 735

Pro Ile Phe Ser Glu Phe Arg Gly Met Lys Ala Val Val Val Asp His
            740                 745                 750

Arg Pro Ala Arg Ala Lys Val Ser Trp Tyr His Phe Gln Arg Leu Gly
        755                 760                 765

Ile Arg Val Glu Val Val Pro Arg Val Glu Gln Ala Leu His Tyr Leu
    770                 775                 780

Lys Ile Gly Thr Thr Thr Val Asn Met Ile Leu Ile Glu Gln Glu Ile
785                 790                 795                 800

Trp Asn Arg Glu Ala Asp Asp Phe Ile Lys Lys Leu Gln Lys Asp Pro
                805                 810                 815

Leu Phe Leu Ser Pro Lys Leu Ile Leu Leu Ala Asn Ser Val Glu Ser
            820                 825                 830

Ser Ile Ser Glu Ala Leu Cys Thr Gly Ile Asp Pro Pro Ile Val Ile
        835                 840                 845

Val Lys Pro Leu Arg Ala Ser Met Leu Ala Ala Thr Leu Gln Arg Gly
    850                 855                 860

Leu Gly Ile Gly Ile Arg Glu Pro Pro Gln His Lys Gly Pro Pro Ala
865                 870                 875                 880

Leu Ile Leu Arg Asn Leu Leu Gly Arg Lys Ile Leu Ile Val Asp
                885                 890                 895

Asp Asn Asn Val Asn Leu Arg Val Ala Ala Gly Ala Leu Lys Lys Tyr
            900                 905                 910

Gly Ala Asp Val Val Cys Ala Glu Ser Gly Ile Lys Ala Ile Ser Leu
        915                 920                 925

Leu Lys Pro Pro His Glu Phe Asp Ala Cys Phe Met Asp Ile Gln Met
    930                 935                 940
```

```
Pro Glu Met Asp Gly Phe Glu Ala Thr Arg Arg Ile Arg Asp Met Glu
945                 950                 955                 960

Glu Glu Met Asn Lys Arg Ile Lys Asn Gly Glu Ala Leu Ile Val Glu
                965                 970                 975

Asn Gly Asn Lys Thr Ser Trp His Leu Pro Val Leu Ala Met Thr Ala
            980                 985                 990

Asp Val Ile Gln Ala Thr His Glu Glu Cys Leu Lys Cys Gly Met Asp
        995                 1000                1005

Gly Tyr Val Ser Lys Pro Phe Glu Ala Glu Gln Leu Tyr Arg Glu
    1010                1015                1020

Val Ser Arg Phe Phe Asn Ser Pro Ser Asp Thr Glu Ser
    1025                1030                1035

<210> SEQ ID NO 6
<211> LENGTH: 1080
<212> TYPE: PRT
<213> ORGANISM: Arabidopsis thaliana

<400> SEQUENCE: 6

Met Arg Arg Asp Phe Val Tyr Asn Asn Ala Met Phe Asn Pro Leu
1               5                   10                  15

Thr Thr His Tyr Ser Ser Asp Met Asn Trp Ala Leu Asn Asn His Gln
                20                  25                  30

Glu Glu Glu Glu Pro Arg Ile Glu Ile Ser Asp Ser Glu Ser
            35                  40                  45

Leu Glu Asn Leu Lys Ser Ser Asp Phe Tyr Gln Leu Gly Gly Gly Gly
50                  55                  60

Ala Leu Asn Ser Ser Glu Lys Pro Arg Lys Ile Asp Phe Trp Arg Ser
65                  70                  75                  80

Gly Leu Met Gly Phe Ala Lys Met Gln Gln Gln Gln Leu Gln His
                85                  90                  95

Ser Val Ala Val Lys Met Asn Asn Asn Asn Asn Asp Leu Met Gly
                100                 105                 110

Asn Lys Lys Gly Ser Thr Phe Ile Gln Glu His Arg Ala Leu Leu Pro
            115                 120                 125

Lys Ala Leu Ile Leu Trp Ile Ile Val Gly Phe Ile Ser Ser Gly
        130                 135                 140

Ile Tyr Gln Trp Met Asp Asp Ala Asn Lys Ile Arg Arg Glu Glu Val
145                 150                 155                 160

Leu Val Ser Met Cys Asp Gln Arg Ala Arg Met Leu Gln Asp Gln Phe
                165                 170                 175

Ser Val Ser Val Asn His Val His Ala Leu Ala Ile Leu Val Ser Thr
                180                 185                 190

Phe His Tyr His Lys Asn Pro Ser Ala Ile Asp Gln Glu Thr Phe Ala
        195                 200                 205

Glu Tyr Thr Ala Arg Thr Ala Phe Glu Arg Pro Leu Leu Ser Gly Val
    210                 215                 220

Ala Tyr Ala Glu Lys Val Val Asn Phe Glu Arg Glu Met Phe Glu Arg
225                 230                 235                 240

Gln His Asn Trp Val Ile Lys Thr Met Asp Arg Gly Glu Pro Ser Pro
                245                 250                 255

Val Arg Asp Glu Tyr Ala Pro Val Ile Phe Ser Gln Asp Ser Val Ser
            260                 265                 270

Tyr Leu Glu Ser Leu Asp Met Met Ser Gly Glu Glu Asp Arg Glu Asn
```

```
              275                 280                 285
Ile Leu Arg Ala Arg Glu Thr Gly Lys Ala Val Leu Thr Ser Pro Phe
290                 295                 300
Arg Leu Leu Glu Thr His His Leu Gly Val Val Leu Thr Phe Pro Val
305                 310                 315                 320
Tyr Lys Ser Ser Leu Pro Glu Asn Pro Thr Val Glu Glu Arg Ile Ala
                325                 330                 335
Ala Thr Ala Gly Tyr Leu Gly Gly Ala Phe Asp Val Glu Ser Leu Val
                340                 345                 350
Glu Asn Leu Leu Gly Gln Leu Ala Gly Asn Gln Ala Ile Val Val His
                355                 360                 365
Val Tyr Asp Ile Thr Asn Ala Ser Asp Pro Leu Val Met Tyr Gly Asn
370                 375                 380
Gln Asp Glu Glu Ala Asp Arg Ser Leu Ser His Glu Ser Lys Leu Asp
385                 390                 395                 400
Phe Gly Asp Pro Phe Arg Lys His Lys Met Ile Cys Arg Tyr His Gln
                405                 410                 415
Lys Ala Pro Ile Pro Leu Asn Val Leu Thr Thr Val Pro Leu Phe Phe
                420                 425                 430
Ala Ile Gly Phe Leu Val Gly Tyr Ile Leu Tyr Gly Ala Ala Met His
                435                 440                 445
Ile Val Lys Val Glu Asp Asp Phe His Glu Met Gln Glu Leu Lys Val
                450                 455                 460
Arg Ala Glu Ala Ala Asp Val Ala Lys Ser Gln Phe Leu Ala Thr Val
465                 470                 475                 480
Ser His Glu Ile Arg Thr Pro Met Asn Gly Ile Leu Gly Met Leu Ala
                485                 490                 495
Met Leu Leu Asp Thr Glu Leu Ser Ser Thr Gln Arg Asp Tyr Ala Gln
                500                 505                 510
Thr Ala Gln Val Cys Gly Lys Ala Leu Ile Ala Leu Ile Asn Glu Val
                515                 520                 525
Leu Asp Arg Ala Lys Ile Glu Ala Gly Lys Leu Glu Leu Glu Ser Val
530                 535                 540
Pro Phe Asp Ile Arg Ser Ile Leu Asp Asp Val Leu Ser Leu Phe Ser
545                 550                 555                 560
Glu Glu Ser Arg Asn Lys Ser Ile Glu Leu Ala Val Phe Val Ser Asp
                565                 570                 575
Lys Val Pro Glu Ile Val Lys Gly Asp Ser Gly Arg Phe Arg Gln Ile
                580                 585                 590
Ile Ile Asn Leu Val Gly Asn Ser Val Lys Phe Thr Glu Lys Gly His
                595                 600                 605
Ile Phe Val Lys Val His Leu Ala Glu Gln Ser Lys Asp Glu Ser Glu
                610                 615                 620
Pro Lys Asn Ala Leu Asn Gly Val Ser Glu Glu Met Ile Val Val
625                 630                 635                 640
Ser Lys Gln Ser Ser Tyr Asn Thr Leu Ser Gly Tyr Glu Ala Ala Asp
                645                 650                 655
Gly Arg Asn Ser Trp Asp Ser Phe Lys His Leu Val Ser Glu Glu Gln
                660                 665                 670
Ser Leu Ser Glu Phe Asp Ile Ser Ser Asn Val Arg Leu Met Val Ser
                675                 680                 685
Ile Glu Asp Thr Gly Ile Gly Ile Pro Leu Val Ala Gln Gly Arg Val
                690                 695                 700
```

Phe Met Pro Phe Met Gln Ala Asp Ser Ser Thr Ser Arg Asn Tyr Gly
705                 710                 715                 720

Gly Thr Gly Ile Gly Leu Ser Ile Ser Lys Cys Leu Val Glu Leu Met
            725                 730                 735

Arg Gly Gln Ile Asn Phe Ile Ser Arg Pro His Ile Gly Ser Thr Phe
        740                 745                 750

Trp Phe Thr Ala Val Leu Glu Lys Cys Asp Lys Cys Ser Ala Ile Asn
    755                 760                 765

His Met Lys Lys Pro Asn Val Glu His Leu Pro Ser Thr Phe Lys Gly
770                 775                 780

Met Lys Ala Ile Val Val Asp Ala Lys Pro Val Arg Ala Val Thr
785                 790                 795                 800

Arg Tyr His Met Lys Arg Leu Gly Ile Asn Val Asp Val Val Thr Ser
                805                 810                 815

Leu Lys Thr Ala Val Val Ala Ala Ala Phe Glu Arg Asn Gly Ser
            820                 825                 830

Pro Leu Pro Thr Lys Pro Gln Leu Asp Met Ile Leu Val Glu Lys Asp
        835                 840                 845

Ser Trp Ile Ser Thr Glu Asp Asn Asp Ser Glu Ile Arg Leu Leu Asn
    850                 855                 860

Ser Arg Thr Asn Gly Asn Val His His Lys Ser Pro Lys Leu Ala Leu
865                 870                 875                 880

Phe Ala Thr Asn Ile Thr Asn Ser Glu Phe Asp Arg Ala Lys Ser Ala
                885                 890                 895

Gly Phe Ala Asp Thr Val Ile Met Lys Pro Leu Arg Ala Ser Met Ile
            900                 905                 910

Gly Ala Cys Leu Gln Gln Val Leu Glu Leu Arg Lys Thr Arg Gln Gln
        915                 920                 925

His Pro Glu Gly Ser Ser Pro Ala Thr Leu Lys Ser Leu Leu Thr Gly
    930                 935                 940

Lys Lys Ile Leu Val Val Asp Asp Asn Ile Val Asn Arg Arg Val Ala
945                 950                 955                 960

Ala Gly Ala Leu Lys Lys Phe Gly Ala Glu Val Val Cys Ala Glu Ser
                965                 970                 975

Gly Gln Val Ala Leu Gly Leu Leu Gln Ile Pro His Thr Phe Asp Ala
            980                 985                 990

Cys Phe Met Asp Ile Gln Met Pro  Gln Met Asp Gly Phe  Glu Ala Thr
        995                 1000                1005

Arg Gln  Ile Arg Met Met Glu  Lys Glu Thr Lys Glu  Lys Thr Asn
    1010                1015                1020

Leu Glu Trp His Leu Pro Ile  Leu Ala Met Thr Ala  Asp Val Ile
    1025                1030                1035

His Ala  Thr Tyr Glu Glu Cys  Leu Lys Ser Gly Met  Asp Gly Tyr
    1040                1045                1050

Val Ser  Lys Pro Phe Glu Glu  Glu Asn Leu Tyr Lys  Ser Val Ala
    1055                1060                1065

Lys Ser  Phe Lys Pro Asn Pro  Ile Ser Pro Ser Ser
    1070                1075                1080

<210> SEQ ID NO 7
<211> LENGTH: 4595
<212> TYPE: DNA
<213> ORGANISM: Arabidopsis thaliana

<400> SEQUENCE: 7

```
atgtctataa cttgtgagct cttgaatctt acttcaaaga aagctaagaa gtcgtcgagc      60
agtgacaaga aatggctaaa gaagcctctc ttcttcctga ttttgtgtgg ctctttggta     120
attgttttgg ttatgttctt acggttaggt agaagtcaga aggaggagac agattcttgt     180
aatggagaag agaaagtgtt gtatagacat caaaatgtca caagaagtga gattcatgat     240
ttggtctctt tgttctctga ttcagatcag gtaattgcat gaattgactt gtatttgttg     300
aaattgagct tttgaatacg caccagattt gccttaaagt gtaacagttt ctctgtattt     360
gttgtaggta acatcctttg aatgtcataa ggaatcaagc cctggaatgt ggacaaacta     420
tggtattaca tgttccctga gtgtgcgttc tgataaacaa gagactagag ggcttccctg     480
gaatcttggc ttaggacatt ctatctcatc aacatcttgt atgtgtggta atcttgaacc     540
ggtaagataa tattcgattc gacaacatgt gaaggaaatg ctttaagatt tggtgtttag     600
ctagttctca caaagttta ttgtgaatgt gtttggttat gagtagattt tacagcaacc     660
tgaaaacctt gaggaagaaa accatgaaga agggctggag cagggtttgt catcgtattt     720
aagaaatgca tggtggtgtc taatccttgg tgtgttagtg tgccataaga tttatgtatc     780
tcattctaaa gcacgaggtg agaggaaaga gaaagtacat ctgcaagagg ctttagctcc     840
aaagaagcag caacaacgtg ctcagacttc ttctagaggg gctggaagat ggaggaagaa     900
tatccttctc cttggtattt taggaggagt ttccttctct gtttggtggt tttgggacac     960
taatgaggag atcataatga aaaggaggga gactttggca acatgtgtg acgaacgagc    1020
acgtgtttta caagatcagt tcaatgttag cttgaaccat gttcatgcct tgtctattct    1080
tgtatctaca tttcatcatg gtaaaatccc atctgccatt gatcaggtga tgttttttc    1140
ttactgctaa atacattttg tgtctcaagt ttatgtttaa atcatcaact tctgttacat    1200
ttacagagaa catttgaaga atatactgag agaacaaact tgagaggcc acttactagt    1260
ggtgtagcgt atgctttgaa agtcccacac tcagaaagag agaaatttga aaaggagcat    1320
ggatgggcaa taagaaaat ggaaactgag gaccagacag ttgtacaaga ttgtgttcct    1380
gaaaactttg atcccgcacc gattcaagac gaatacgcgc cagttatatt tgctcaagaa    1440
actgtttccc atattgtatc ggtcgacatg atgtctggag aagtcagtaa cgtctaaaag    1500
tttcttgaac tattttgcca aaccaatgtc cttaaaagag aattcaaaag tctaactatt    1560
ttgcaggaag accgtgaaaa catcttacgg gcaagggcat caggaaaagg agtgttaaca    1620
tctccattta agcttcttaa gtcaaatcat cttggtgttg tgttgacctt tgctgtctat    1680
gacacgagcc taccgcctga tgctacagaa gaacagcgtg ttgaagcaac tattgggtac    1740
tacttctact taaatgatt ctaggactga agaaattgaa cctatgtaac aaagaatgat    1800
ctctggacca gaaatatta ataagataca cttaaaaaca ggtaccttgg tgcatcatat    1860
gatatgccat cgctggtgga gaacttctt caccaacttg ccagcaaaca gacaattgct    1920
gtggatgttt acgacacaac taacacttca ggtctaataa aaatgtatgg ctcagaaatt    1980
ggggatataa gtgagcagca tataagtagc cttgattttg gtgatccatc aaggaaccat    2040
gagatgcatt gcaggttagt tagctctaac tgttatggta cattttata agatatgttt    2100
cacttctctg tttctgaag tatgaaagtg gcatttttca tttacaggtt taagcataaa    2160
cttcccattc cctggacagc gataacaccg tcgatcttag ttctggttat tacttttctt    2220
gttggttata ttttatatga agccatcaac cgaattgcga cagttgaaga ggattgtcag    2280
aagatgaggg aactcaaagc tcgtgctgag gccgctgaca ttgcaaagtc acaggtgatc    2340
```

```
tttgtgaatc atatagtctc aaaagcttta cttgtttttt cactgaaatg cttcttattt    2400
tgcagttcct agcaactgtt tctcatgaga tacggactcc gatgaatgga gttttaggta    2460
cttttctac ttatccttgg tcaatattgc atgttctctt aaaatcagct gaaacgttta    2520
agcattttgt tacaggaatg ctgaaaatgc tgatggacac cgatcttgat gcgaagcaga   2580
tggactatgc gcaaactgct catggcagtg ggaaggatct tacatcacta ataaatgagg    2640
ttcttgatca ggcaaagatt gaatccggaa ggctcgagct tgaaaatgtg ccttttgata   2700
tgcgttttat tcttgataat gtttcatctc tcctctctgg caaggcaaat gaaaaaggaa   2760
ttgaggtata attataaact gcatgacctt ctactttctt aatgttttca tatggcaaac    2820
aaattccata tgtaatgaaa tgttgacttc ttgttacagt tggccgttta tgtttctagt    2880
caagttcctg atgttgtagt cggtgatccg agtcggttcc ggcagatcat tacaaacctg    2940
gttggaaact caatcaaagt aatttactcc ttacttctta cagaacaaca ggcttcacga   3000
atctctacta ttacagtact catttgttat ttacttaata acagttcaca caggaaaggg   3060
gacacatatt tatctcagtg caccttgcag atgaggtaaa ggagcctctt actattgaag    3120
acgcagtgct aaaacagcga ctagctttag gatgcagcga gtccggtgag acagttagcg    3180
ggtttcctgc ggtaaatgca tggggaagct ggaagaattt caagacatgt tacagtactg    3240
agagtcagaa ttctgatcaa atcaaattgc tagttacagt ggaggacact ggagttggca   3300
tacctgtgga tgcacaaggc cgaatcttca cccttttat gcaagccgac agttccacat    3360
cgcggactta tggtggaact ggcataggtt tgagtataag caaacgtttg gttgaactca   3420
tgcaaggaga gatggggttt gtgagtgagc ccgggatagg cagtactttt tcatttactg    3480
gagttttcgg gaaagcagaa acaaatacgt cgattactaa gctggaacga ttcgatctag    3540
ctattcagga gtttacagga ttgagagcat tagttattga taacagaaac attagagcag    3600
aggtcaccag gtacgaactt cggagactgg gaatatctgc agacattgtt tcaagtctga   3660
gaatggcatg cacttgttgt atcaggtact ttacgtacat tagtgtctgt ctgtctttag    3720
agattatagt gagttcacta aaagcgtttt attgttctgg aatctttgca gcaaattaga    3780
aaatttggct atgattctaa tagacaaaga cgcctggaac aaggaagaat ttcagtact    3840
tgacgagttg tttacccgaa gcaaagtaac ctttacaaga gtcccaaaga ttttctttt    3900
ggcaacttct gcaactctta ctgagcgcag tgagatgaag tctactggtc tcatcgatga   3960
ggtggtgata aagcctcttc ggatgagtgt cttaatatgt tgcttgcaag aaacccttgt   4020
caatggcaag aagaggcaac cgaacagaca gcgaagaaat cttggacact tgctaagaga    4080
aaaacagatt ctggttgtgg atgataatct tgtgaacaga cgagttgcag aaggtgcact    4140
taagaaatat ggagctattg ttacatgcgt tgagagtggc aaagctgcat ggcaatgct    4200
taagccgcct cataacttcg atgcttgctt catggatctc cagatgcctg aaatggatgg    4260
gtagataact attttcaat cttatctctt cagcttgttc atttcttgga tgtcgtcctt   4320
ggtaacttta taatttttg cgcagatttg aagcgacaag gagagtccgt gagctggaga    4380
gggaaatcaa taagaaaata gcttctggag aagtttcagc tgaaatgttc tgtaaattta    4440
gtagttggca cgtcccgata ttagcaatga cagcagatgt tattcaggct actcatgaag    4500
aatgcatgaa atgtggaatg gatggttatg tatcaaaacc gtttgaagag gaagtgctct    4560
acacagcggt agcaagattc tttgaacctt gttaa                               4595
```

<210> SEQ ID NO 8

<211> LENGTH: 4248
<212> TYPE: DNA
<213> ORGANISM: Arabidopsis thaliana

<400> SEQUENCE: 8

| | | | | | |
|---|---|---|---|---|---|
| atgagtctgt | tccatgtgct | agggtttggt | gtcaagattg | ggcatctctt | ctggatgcta | 60 |
| tgctgctggt | ttgtttcttg | gttcgttgat | aatgggatcg | aggacaagtc | tggtctttta | 120 |
| gttggctctg | tcggtgatct | tgagaagact | aagatgacta | cgttgaagaa | gaagaacaag | 180 |
| atgtggttct | ggaataagat | ctctagcagc | ggactcaaga | tcccgagttt | ctcttatcag | 240 |
| tttcttggct | ctgttaaatt | caacaaggcg | tggtggagga | agcttgtggt | ggtttgggtt | 300 |
| gtcttctggg | tcttggtctc | tatttggacg | ttttggtact | ttagctcgca | agctatggag | 360 |
| aagaggaaag | agacgctagc | tagtatgtgt | gatgagagag | ctcgtatgct | gcaggatcag | 420 |
| ttcaacgtta | gcatgaatca | tgttcaagcc | atgtctatct | tgatctcaac | cttccaccat | 480 |
| ggcaagattc | cttctgctat | cgatcaggta | ttctcgattc | cgcatcttct | tgtcttctaa | 540 |
| tctgtttgga | ttgatgcctg | agatctagtc | ttgcttgtag | tacataagtt | gttcctacgg | 600 |
| tgtagtatat | gaacggtcct | tggatgatgg | tagcttttt | cattcaactt | gctctcgaat | 660 |
| ttcagttagg | atttacaatt | ttgctgattg | ttgcttacag | tctttgtatt | tagctaacac | 720 |
| ttggtagctt | gattcctatc | ttcttgagta | ttagtgaaca | gtaactaaca | ttaagaagct | 780 |
| ttgtgtagag | aacattctca | gagtacactg | atagaacttc | ctttgagagg | cctcttacta | 840 |
| gcggggtagc | ttatgctatg | agggtgctcc | attcagagag | ggaagagttc | gagaggcaac | 900 |
| aaggttggac | tattaggaag | atgtattctc | ttgaacaaaa | cccagttcac | aaggatgact | 960 |
| atgacctgga | agctttggaa | ccatcccctg | tccaagaaga | gtacgctcca | gtcatctttg | 1020 |
| ctcaggacac | tgtttctcac | gttgtttctc | tcgatatgct | gtctgggaaa | gtaagcttct | 1080 |
| ttactggttc | taattttact | gttttatgt | aatttactat | catggtctac | actcactacc | 1140 |
| gggcgaatcc | tgccgacatg | gctagttcat | atttcaatct | cggcttaccg | attaagttgt | 1200 |
| tttgatcatt | ttatttaaag | tttagagcac | tgttttaact | gatacttatt | ctcactcaat | 1260 |
| tcctcttgat | aggaagatcg | tgaaaacgtt | ttgcgggcca | ggagttcagg | taaaggggtt | 1320 |
| ttgacagctc | ctttcccatt | gataaagaca | aatagacttg | gggtgatcct | gacatttgca | 1380 |
| gtgtacaaga | gagatctccc | ctccaatgca | acgccaaaag | agagaattga | ggctactaac | 1440 |
| gggtgtgtag | cataggcgtc | taaataaata | ataacgcata | agttttacaa | cattattttt | 1500 |
| gctcattcat | ctcttttgat | gcccctgaag | gtatctcggg | ggagtgtttg | acattgagtc | 1560 |
| cctggtagaa | aacttgcttc | aacagctggc | tagcaagcaa | acgattcttg | tcaatgtgta | 1620 |
| cgatatcacc | aatcactctc | aaccgattag | catgtatggt | acaaatgtgt | cggctgatgg | 1680 |
| gttggaacgt | gttagtccac | taatctttgg | cgatccattg | agaaagcatg | agatgcgttg | 1740 |
| caggtacttg | cagttggcac | atacatatgt | ctgtaatttc | ttcttgtttg | caagaatcca | 1800 |
| ggtgctaaca | ttttgttgtg | agcttcttcc | tctttgtaga | tttaagcaga | aaccaccatg | 1860 |
| gccagtgcta | tcaatggtga | catcattcgg | tatccttgtg | attgcgttac | ttgttgcaca | 1920 |
| tataatccac | gcaaccgtta | gtcgaataca | caaagttgaa | aagattgtg | ataaaatgaa | 1980 |
| gcagctcaag | aaaaaggctg | aagcagcaga | tgttgcaaag | tcacaggtaa | atacatcatc | 2040 |
| ctcagttgat | aaatttccac | agcatattaa | actttctatg | acagagagaa | gagttgtaat | 2100 |
| ctaactttt | tttatgcagt | tccttgccac | tgtttcacat | gaaatcagaa | ctccaatgaa | 2160 |
| tggtgttcta | ggtgagtatc | gaaatggcca | ctatgttgcc | tccttctctc | acctatgccc | 2220 |

-continued

```
atgaatattt tctgaagaac aaacttaacc aaatattctc atgttgactt tgatctgggg      2280
tgtaggaatg ttgcatatgc ttatggacac agagttagat gttacgcaac aggattatgt      2340
taggaccgca caggcaagtg aaaagcttt agtctcgcta ataaatgagg ttttggacca       2400
agcaaagatt gaatctggaa agcttgaact tgaggaggtg cggtttgatt tgagaggaat      2460
attagatgat gtcctgtcac tcttctctag caagtcccaa caaaggggg tggaggtaac      2520 ttactatatg atctgcaaag caagggttgt aactgatagc aagtctttct tactgatttt      2580
ttgagtgttg ctgatgaacg cagttggcag tatacatatc tgatcgtgtt ccagatatgt      2640
taattggtga tcctgggagg tttcgacaaa tactcacaaa tcttatgggt aattccatta      2700
aggtaaactt ttttattatg ttttttttctg accattcctt gcatccgagt tgatcaacgg     2760
agctgatcat ttatatatat tctggcagtt cactgagaaa ggacacatct ttgtaactgt      2820
tcatttggtg gatgagctat ttgaatctat cgatggagag acagcatcat ctccggaaag      2880
tacactgagt gggcttccag ttgcagaccg gcagaggagc tgggaaaact ttaaagcttt      2940
cagctccaac gggcatcgga gctttgaacc atctccccct gatataaacc taatcgtctc      3000
agttgaggat actggcgtag ggatccctgt agaagcgcag tcccgtattt ttacgccttt      3060
catgcaagtc ggaccatcca tatccaggac gcatggaggc acaggaattg gacttagcat      3120
aagcaaatgt ctagttggac tgatgaaggg agaaattgga ttctcgagta ctcccaaggt      3180
tgggtccaca ttcacattta ctgctgtatt ttccaatggg atgcaaccag ctgaaagaaa      3240
gaatgacaac aaccagccca tattctcgga attccggggc atgaaagctg tggttgtgga      3300
ccataggcct gcaagggcaa aagtctcgtg gtaccatttt cagcgtcttg gaattcgagt      3360
cgaagtagtt ccacgtgttg aacaggctct acattatctg aagattggta ctaccactgt      3420
gaatatgata ctcatagagc aagaaatatg gaataggaa gcagatgatt tcattaaaaa       3480
gctacagaaa gaccctcttt tcctttctcc taagttgatt ttgttagcaa actcagtaga      3540
atcgtcaata tcagaggctt tatgcaccgg tatagatcct ccaatagtga tagtgaaacc      3600 attgaggcg agtatgctag cagcaacttt gcagagggga ttgggtattg gaatcagaga      3660
accacctcaa cacaagggac tcctgctttt gattctcagg aatcttctcc ttggtagaaa      3720
aattttaatc gtggatgata caacgtaaa cctcagagtg gcagcgggag ctctgaaaaa      3780
gtacggagct gatgtggtct gcgctgagag tgggataaag gcaatctcat tgcttaagcc      3840
acctcacgag tttgatgctt gcttcatgga cattcagatg ccagaaatgg atgggtatgc      3900
ctgattggta tactagtttt tttgaaaagt tcgaaatatg taataagaaa attgaaatgt      3960
ttttctgccc tgtctttctg cagatttgaa gctacaagga gaatacgaga tatggaagag      4020
gagatgaaca agagaataaa gaatgggag ctttgatag tagagaacgg taacaaaaca        4080
agctggcatc ttccggtatt agcaatgacg gcagatgtga tccaagcaac gcatgaggaa      4140
tgtctgaagt gtggaatgga tgggtatgta tcaaaaccat ttgaagcaga gcagctgtac      4200
agggaagttt ctcgcttttt caattcgcct tcagatacag aatcataa                  4248
```

<210> SEQ ID NO 9
<211> LENGTH: 4685
<212> TYPE: DNA
<213> ORGANISM: Arabidopsis thaliana

<400> SEQUENCE: 9

```
atgagaagag attttgtgta taataataat gcaatgttca atcctctcac aactcattac      60
```

```
aggtaactaa aataatttct ccatgtgctt gcttattagt cgttcttcct aatgttatgt      120
ttctctctgt gttctttctt tctttggtca aagctttaat tttttttcta ttgttggatt      180
tgagacagtg aacatagcta tgttcttgtt ccaataataa acaatcacgc ctgtaaagag      240
cttatgattg attagtgtgt tttttagtat taattaattt ctctgacaat aattacttag      300
tttttaattc ttctctgtaa gaaacctttg gaaactgagc aaagttgctt cttttgagaa      360
ccatgcgttt cttttctctct tttgttcttg aattcgcaaa aacatgtcct ttttcgtcta      420
caggtttcta gggtttgttt ctgtactata aactatgttt atggtaacat tcttaatcat      480
aactacacta ccaatgcttt tatgttatat gtatgcaaaa aaggctctaa cttttgtttt      540 cttttcactat tgtttcttct tttgttctct attgttgtag ctcagatatg aactgggcac      600
tcaacaatca tcaagaagaa gaagaagagc cacgaagaat tgaaatttct gattccgagt      660
cactagaaaa cttgaaaagc agcgattttt atcaactggg tggtggtggt gctctgaatt      720
cgtcagaaaa gccgagaaag atcgattttt ggcgttcggg gttgatgggt tttgcgaaga      780
tgcagcagca gcaacagctt cagcattcag tggcggtgaa gatgaacaat aataataata      840
acgatctaat gggtaataaa aagggtcaa cttttcataca agaacatcga gcattgttac      900
caaaagcttt gattctgtgg atcatcattg ttgggtttat aagcagtggg atttatcagt      960
ggatggatga tgctaataag attagaaggg aagaggtttt ggtcagcatg tgtgatcaaa     1020
gagctagaat gttgcaggat caatttagtg ttagtgttaa tcatgttcat gctttggcta     1080
ttctcgtctc cacttttcat taccacaaga acccttctgc aattgatcag gtcagtgtgt     1140
gctttattaa aagctcaaag ctttggtgaa attttttgatt cataaatgca aagttgactt     1200
tttttggaac cagaagtttt tgaaatttac tcttttatgt ttggttattg agtaaatgaa     1260
gggaaattta ggccctttgct ttactcattg gtttgtggct aattttgcag gagacatttg     1320
cggagtacac ggcaagaaca gcatttgaga gaccgttgct aagtggagtg gcttatgctg     1380
aaaaagttgt gaattttgag agggagatgt ttgagcggca gcacaattgg gttataaaga     1440
caatggatag aggagagcct tcaccggtta gggatgagta tgctcctgtt atattctctc     1500
aagatagtgt ctcttacctt gagtcactcg atatgatgtc aggcgaggta atataaacat     1560
tatcagacac ttatggtttt gttttttcgg ttaagtatcc gacctgcacc tcttctgaat     1620
tttggctatc ttttctgcag gaggatcgtg agaatatttt gcgagctaga gaaaccggaa     1680
aagctgtctt gactagcect tttaggttgt tggaaactca ccatctcgga gttgtgttga     1740
cattccctgt ctacaagtct tctcttcctg aaaatccgac tgtcgaagag cgtattgcag     1800
ccactgcagg gtaaagttcc catctgatta ctggagcaaa cttttgcttg tgatcatgta     1860
aaaagagatt ttcgagattt catgattggt ttatgtgtgt gatcatgtaa aggaaagagg     1920 tttttttgaga tttcaagatt ggtttgtgtg taaagtaaag attgatgctt gaatttgaaa     1980
tgcaggtacc ttggtggtgc gtttgatgtg gagtctctag tcgagaattt acttggtcag     2040
cttgctggta accaagcaat agttgtgcat gtgtatgata tcaccaatgc atcagatcca     2100
cttgtcatgt atggtaatca agatgaagaa gccgacagat ctctctctca tgagagcaag     2160
ctcgattttg gagaccccctt caggaaacat aagatgatat gcaggtacca cacagaaaat     2220
cttaaagcta aaatactctc tgatatctaa aaactgatat cttgtttgaa caatttcgag     2280
tgcaggtacc accaaaaggc accaataccg ttgaatgtgc tcacaactgt gccattgttc     2340
tttgcgattg gttccttggt gggttatata ctgtatggtg cagctatgca catagtaaaa     2400
gtcgaagatg atttccatga aatgcaagag cttaaagttc gagcagaagc tgctgatgtc     2460
```

```
gctaaatcgc agtttcttgc taccgtgtct cacgagatca ggacaccaat gaatggcatt      2520
ctcggtacta catcttcaaa caaattccag tactgttgcc tttcatcttt ggtttctcaa      2580
actgcctcaa agattctgtt ttaaaaattt tctgcaggaa tgcttgctat gctcctagat      2640
acagaactaa gctcgacaca gagagattac gctcaaaccg ctcaagtatg tggtaaagct      2700
ttgattgcat tgataaatga ggttcttgat cgcgccaaga ttgaagctgg aaagctggag      2760
ttggaatcag taccatttga tatccgttca atattggatg atgtcctttc tctattctct      2820
gaggagtcaa ggaacaaaag cattgaggta agttttcaat ccaaggaata agatacatc      2880 tatttggagt tgtggctgct aatttcttga tttcaaattt ggcagctcgc ggttttcgtt      2940
tcagacaaag taccagagat agtcaaagga gattcaggga gatttagaca gataatcata      3000
aaccttgttg gaaattcggt taagttagt ccctatttca atctctgcct ttgttggcag      3060
cttgtgtata tgattttgt ttgatcaaga tgttgtcttt ttgacagttc acagagaaag      3120
gacatatctt tgttaaagtc catcttgcgg aacaatcaaa agatgaatct gaaccgaaaa      3180
atgcattgaa tggtggagtg tctgaagaaa tgatcgttgt ttccaaacag tcaagttaca      3240
acacattgag cggttacgaa gctgctgatg gtcggaatag ctgggattca ttcaagcatt      3300
tggtctctga ggagcagtca ttatcggagt ttgatatttc tagcaatgtt aggcttatgg      3360
tttcaatcga agacacgggt attggaatcc ctttagttgc gcaaggccgt gtgtttatgc      3420
cgtttatgca agcagatagc tcgacttcaa gaaactatgg aggtactggt attggtttga      3480
gtataagcaa gtgtcttgtt gaacttatgc gtggtcagat aaatttcata gccggcctc      3540 atattggaag cacgttctgg ttcacggctg ttttagagaa atgcgataaa tgcagtgcga      3600
ttaaccatat gaagaaacct aatgtggaac acttgccttc tacttttaaa ggaatgaaag      3660
ctatagttgt tgatgctaag cctgttagag ctgctgtgac tagataccat atgaaaagac      3720
tcggaatcaa tgttgatgtc gtgacaagtc tcaaaaccgc tgttgttgca gctgctgcgt      3780
ttgaaagaaa cggttctcct ctcccaacaa aaccgcaact tgatatgatc ttagtagaga      3840
aagattcatg gatttcaact gaagataatg actcagagat tcgtttattg aattcaagaa      3900
ccaacggaaa cgttcatcac aagtctccga aactagctct attcgcaaca aacatcacaa      3960
attcggagtt cgacagagct aaatccgcag gatttgcaga tacggtaata atgaaaccgt      4020
taagagcaag catgattggg gcgtgtctgc aacaagttct cgagctgaga aaaacaagac      4080
aacaacatcc agaaggatca tcacccgcaa ctctcaagag cttgcttaca gggaagaaga      4140
ttcttgtggt tgatgataat atagttaaca ggagagtagc tgcaggagct ctcaagaaat      4200
ttggagcaga agtggtttgt gcagagagtg gtcaagttgc tttgggtttg cttcagattc      4260
cacacacttt cgatgcttgc ttcatggata ttcaaatgcc acagatggac gggtaactaa      4320
atcacaacta atactatttt tggattattc ggttttgaa ttgttcggta tgaaaaattt      4380
cccgccaaat tataactgac ttggtttggt tcggattcgg ttaaaatctt ttataaactt      4440
cattgattct cagatttgaa gcaactcgtc agataagaat gatggagaag gaaactaaag      4500
agaagacaaa tctcgaatgg catttaccga ttctagcgat gactgcggat gtgatacacg      4560
cgacctacga ggaatgtctg aaaagtggga tggatggtta cgtctccaaa ccttttgaag      4620
aagagaatct ctataaatcc gttgccaaat cattcaaacc taatcctatc tcaccttcgt      4680
cgtaa                                                                  4685
```

<210> SEQ ID NO 10

<211> LENGTH: 2000
<212> TYPE: DNA
<213> ORGANISM: Arabidopsis thaliana

<400> SEQUENCE: 10

| | | | | | |
|---|---|---|---|---|---|
| taatttgaat | atttatattc | aatttcatac | atattatttt | aaaatttata | attttatata | 60 |
| ctaaaataat | taataacata | ttagattttt | taatgtgtat | gatgtgattc | aattttttaat | 120 |
| acaagttgga | aaatcctaga | attgacgggt | ttaaatcaat | attaatacaa | gatggtatag | 180 |
| tacaggtgaa | actctaaaat | taacaatcaa | aatacaagta | tataattttta | aacattaaac | 240 |
| aatataaata | atatcaacaa | aacatataca | actagcagtt | tactatacat | ttaaaatcaa | 300 |
| ataaaataat | atcatatatt | tgtaatcaac | tttacaataa | aagtttttag | tttaactaaa | 360 |
| atataagcct | acctgctgta | taatgcaagt | taaaattata | aataagcaga | ttaccatcac | 420 |
| gatggatgta | ccttctcaca | tacacaccta | tcaaaaactt | aaaacctttc | aaaacctctt | 480 |
| ggtatattca | aattaggatt | cttcattcat | agaatcatta | ttccaagggt | tttgggatgt | 540 |
| cttatgaaat | gattttggca | gaagaggatg | taaattttttt | tgaataaaag | gtattcaaca | 600 |
| aaacatatgt | tttattggga | ttttttagat | aattaaatca | gagaataggg | ctgggcatat | 660 |
| gagtaaccca | ttcgagttcg | ggtagaaccc | gttcgggttt | gggattaatg | ggtatatgat | 720 |
| ttactaccta | atagaataat | tctaaatatt | cggttcgggt | cgggtccagt | tgggtttggg | 780 |
| tcagtttgga | taaaaagttt | caggccctaa | aaatactcaa | aaaaatagaa | acgagtattt | 840 |
| tgtatgtaga | tagtgcgtct | ctaaacaaaa | aaaactttta | aatttattaa | gttttaataa | 900 |
| atttaattat | atttgaatat | attttactaa | attttgacaa | atataacaaa | taattttgat | 960 |
| aaacataaca | aacataacaa | agtatacaat | gtaatttata | caaatatatta | atgcccgtgc | 1020 |
| tatacagcac | gggttatgat | ctagtcctaa | tatatttca | aagtcaaata | caattttaaa | 1080 |
| cagaacttct | tacataaaaa | taatcagaat | cataaatgta | actgggagac | aaagatacat | 1140 |
| aaactgataa | aaagaaataa | gatgtacata | tagaatcaaa | tcaatacccca | cttctcgtaa | 1200 |
| aacccactca | tcgttatatt | ttatacaaga | taagataaga | cttaagagta | gatgttaaac | 1260 |
| tatgctaatg | aagcaattta | aaaacaccaa | aaagaccaaa | caaaaaacaa | ataacaatga | 1320 |
| gtaggtttta | ggagaagcat | gtattgattc | ttggtatagt | tgagtttatt | tatattttca | 1380 |
| ttagccaatc | actttttcta | atttaactaa | aaatgttata | ataccttccc | cacctagatg | 1440 |
| atgagataat | catggaccca | aaaacctcag | tttttaaaaa | tgtttattca | ccaaaagaca | 1500 |
| aaaacaataa | taataatcaa | aagtagagta | aaagaagaga | gaagtgacat | tcttttttctt | 1560 |
| tagctcataa | tttctctaac | aaatgcttct | tttatccaaa | ctctgatcat | tgagtccagt | 1620 |
| tgggtaatga | gagacaccag | ctgggtttct | tttgtttaag | ctcacaaaca | tctaaaacag | 1680 |
| agaaagcttt | gtcatttttc | tttaccctga | aaccatgaaa | gaagataaag | ctttgtcctt | 1740 |
| tttctctttt | ccgtttcttt | actctcaaca | atgtcttctt | tctcccattg | caacaaccac | 1800 |
| tgggtttggt | tcatcttgtc | ctcttgcgtc | ttaagtaaga | aaaagaaaa | aagctttgcg | 1860 |
| tttgggacta | tgtcacagct | tcttgttctt | cttgtggatg | gtttcaagaa | ctcaactatg | 1920 |
| agattgttgt | tgatagagtt | ttagttttgg | gtttgaagag | atctgaattt | cttcagctga | 1980 |
| atctgagatt | aggagtcgaa | | | | | 2000 |

<210> SEQ ID NO 11
<211> LENGTH: 2000
<212> TYPE: DNA
<213> ORGANISM: Arabidopsis thaliana

<400> SEQUENCE: 11

```
tctggatcca tctctttctt cgtcttcctt tttgatcctt agctcttgcg tcgtgctttt      60
tcaacaggcg agagaggatc gagagggtta gataatttac tgaaaaatta tacgaatgga     120
ccaagactag agatactgaa atgagtgttt gacgatactt taaatgggcc ttatatttt      180
caagttgggc ccgttaatat atgggacaat aacagtata gctcaattgg taaattgact     240
aacttcattt gattcctaca ccatttaaag attttaatc aaattctgat ataactaaga     300
taatatttta aagcatttaa ctaacatgga aaattatgaa atgaaatatt aattttggat     360
agaaaattta aaacatttat ctttgtgaaa taaaaagaaa gtctcttata atataacttg     420
taaagtaatc ctttaaattc taaaagatct aaaacaaaat gagttaaatc ctatgtctat     480
gtgttgaatc tggaagatcg aggtggaaga aaaaggatca tgattcatgg gtgagagaac     540
aaccgttgat tggtgtgttt caactttcaa gcaatcccat tttaaaaaaa taaatttatg     600
taagcaattg caaacaaaat gaatgatta tgctttaaga tatcgacacg tgtaaaacag     660
atgacgtacc aagaaaataa atgattctgt attttgtttt agccatttgt ttttctta     720
aaggaaagtg tatgttgaaa ttgaaaaaac aaaccgagtt atatatatag agttatttga     780
ctaaagaagg aagctttggt taaactaact tgtataattc ttttgtgtag tttagttttg     840
ataaaatggc caaacaattt tggtcacttt accaactact gcaaaaaaac cattttcata     900
ataataaatt gtaacacgcc ttttattttt attattggag ggtgagaact gagaccatat     960
atgcctttgt tcccttcttg tgggtccctt tagccttttt ttttcttttg cctgcgccgt    1020
ttagtgtttt ttcttttata tataaataga ggtaagttat tttaccaatc atttggtgtt    1080
attaatagta gtattaatga ggttctaaac ttgtttataa aaatcagatc ttactaaaca    1140
aactcaaaga atctcaacta tgaacatttt tcttctagaa tcgagttta acatcatcat    1200
cagcaggata taatttttg tgtttgaatt ttatctgtat ttttttagg agtacataag    1260
cagcttaaga ttaaaatata tattaatgga agtatgaatg aaaaaagaaa agaaagataa    1320
tcagataata gagagagaga gagagagaag gaagcagaca tttgtcttcc accatattct    1380
tctcatcttt tccgatgata gattcttctt cttcttcttc ttctactact acttctgctc    1440
ctctttctta agtttctcca tttgataatt cactcaagtc tccagctcct cttcttcttc    1500
tcgttgcttt attcgctctc tttcactcat catcatcaca ctcaaagatt tctgttgtat    1560
tggagcaagc tctagcgaat tttcgtactc cccttgtaga attttagttt cctgttttag    1620
atttcgagga atctcgcttt ggaaacttta agctcctgtt caaagtttct accttttgttt    1680
attttgtttt tgttttcttc tctcttatct ttcgtcatct ttgattaagt aaccactttg    1740
atctctcaat ttcagccttt gggttgtcta atctgacacg ttcctctgtc ttagcttttcc    1800
ttttctcttc tcgtttgtgg gaagcctaca aggattaatt attaaatacc caaccccaaa    1860
aaattcttcc ttttttgattc tctgattcgt cccttttttgt acatggtttc tgtttggttg    1920
ttagagcttc ttgctgagtt gaattgagct ggttgcaatc actctgtttc ttgggggttg    1980
atcgtgtatt caagtggtgg                                                 2000
```

<210> SEQ ID NO 12
<211> LENGTH: 2000
<212> TYPE: DNA
<213> ORGANISM: Arabidopsis thaliana

<400> SEQUENCE: 12

```
ccaattcacg ttaaatctat ctcttgctct tgcttcctcc aaaaaaaaaa aaaaatcatt      60
cccagatcca tcgatatgaa attgtataga aaaaatggta ttcgatccaa gtttattgtc     120
ttctattttt cttaggttaa tttcacttta ttccagattc attgtttgtt ttttctttct     180
cggaagagca caatgtgagt ttcactggcc tctgttataa acatatatag aaatctgtaa     240
caaaaatcat tactaaaatt ctgtgacatg tgcagcgatc aaagaatcaa tagcggaaaa     300
agaaactaca ctgcattcat ctatgactga agcttctga tcaagccatg aaattaaggt      360
atcccaaaca cgtatcttct ctatgtttat caatcttgct ttaagttcta attctgcata     420
tttcaaagga accatacaag tgttcctaaa atccatttga atattcaaaa acttctctca     480
aatatcatgt agttatagaa gctactgtct ctaagcgcac gagagaaagc tacacaaccc     540
acgtcagttt ccatctacac atataaggta ataataatat tttcatgtat ctttaataat     600
agctctatgt tttttctgt attttcatt ataaaactca taactatgtt atcatttaat       660
atggtactaa tttaatggga ttgatttact attgcctcaa acatgtaata atttaatgat     720
tttttgtttt taacgttttt agaaattcat gagcatttta aatttgtggt taggtcataa     780
caatttgcta ttacaaaaaa aagaaacact ctaaataata taaaaaatag tttaccgtat     840
aatactagta gtaaataaat aatttgattg ttattcataa attttgaatt ctaaaatctc     900
ctgaatcaac tcatgcaatt gtcttaagaa ttacacgtgg ataaatcatg ggcttatgag     960
tcaggcccat ttaaccgggg tattttcgta gttaagagac tagaatggtg ggtatttcag    1020
gtaaaaggtc tatggggcca gatctgcgct ttgtcgcgat gtcattatcg ccaaagatat    1080
gcgatagcga ctctcgtaca aagtctctca ctcacctata ttttttgttt tcttatattt    1140
caacaaaaaa acgttttatt ttccttttgg tgtaagtaaa aaaacaaaac aaaacgtttt    1200
atttctaaag ttcagaaaac ttatttatac caaggaaaaa atagataata aattttgaga    1260
agttggtgac tatatattac ttcacttatt caagaaattt aaacatggta aatgttactt    1320
taaatgttaa atgatgtata agaaatgtaa tgaaattgaa taaatgtagt tttaaagatg    1380
ttttaattag taagacaaac ctagttagtg tcacaataat tatatttttt tttttgtcat    1440
ccaaaattat taaagctcaa gtaaaccaat cctgagggat attatttaca aatgtgtatat   1500 gatgcggttc ggtgcggatc ttccgcgcca aattatacgc ttttatatta gcattataaa    1560
aaattataga taaagagaag tttgtgaatt cttcattgtc gctttgcaat ttctctaaat    1620
acacagtaaa taccgacaat tcggttagag aaaatatatc tatttcgtat aataatgtta    1680
actttgagga gatttgggt aaaataataa cttttgttgg atggatcata tcatgagcca     1740
ttaagaaaaa gtccaaaact tttcttcttc aaagttggac tcaagttaga aaagaaaaa     1800 agagctagag agatataaaa atgaaaagaa agttcatggc aaaaaactga tatagacaga    1860
gacacagaga gagagaaacg tatctgaaga aaatctaaaa aattcgattc aatttttttc    1920
ttacttttaa aagcaaaaaa tctcactaaa acaaaagaag aagaagaag aaagaaaatg    1980 gaatacctac atttgaagtg                                                2000
```

<210> SEQ ID NO 13  
<211> LENGTH: 2000  
<212> TYPE: DNA  
<213> ORGANISM: artificial sequence  
<220> FEATURE:  
<223> OTHER INFORMATION: Modified AtCHK2 promoter with SNP

<400> SEQUENCE: 13

```
taatttgaat atttatattc aatttcatac atattatttt aaaatttata attttatata      60
```

```
ctaaaataat taataacata ttagattttt taatgtgtat gatgtgattc aattttaat      120
acaagttgga aaatcctaga attgacgggt ttaaatcaat attaatacaa gatggtatag      180
tacaggtgaa actctaaaat taacaatcaa atacaagta tataatttta aacattaaac       240
aatataaata atatcaacaa aacatataca actagcagtt tactatacat ttaaaatcaa      300
ataaaataat atcatatatt tgtaatcaac tttacaataa aagttttag tttaactaaa       360
atataagcct acctgctgta taatgcaagt taaaattata aataagcaga ttaccatcac      420
gatggatgta ccttctcaca tacacaccta tcaaaaactt aaaacctttc aaaacctctt      480
ggtatattca aattaggatt cttcattcat agaatcatta ttccaagggt tttgggatgt      540
cttatgaaat gattttggca gaagaggatg taaattttt tgaataaaag gtattcaaca       600
aaacatatgt tttattggga ttttttagat aattaaatca gagaataggg ctgggcatat      660
gagtaaccca ttcgagttcg ggtagaaccc gttcgggttt gggattaatg ggtatatgat      720
ttactaccta atagaataat tctaaatatt cggttcgggt cgggtccagt tgggtttggg      780
tcagtttgga taaaagttt caggccctaa aaatactcaa aaaaatagaa acgagtattt       840
tgtatgtaga tagtgcgtct ctaaacaaaa aaacttta aatttattaa gttttaataa        900
atttaattat atttgaatat attttactaa attttgacaa atataacaaa taattttgat      960
aaacataaca aacataacaa agtatacaat gtaatttata caaatatta atgcccgtgc       1020
tatacagcac gggttatgat ctagtcctaa tatattttca aagtcaaata caattttaaa      1080
cagaacttct tacataaaaa taatcagaat cataaatgta actgggagac aaagatacat      1140
aaactgataa aaagaaataa gatgtacata tagaatcaaa tcaatacccca cttctcgtaa    1200
aacccactca tcgttatatt ttatacaaga taagataaga cttaagagta gatgttaaac     1260
tatgctaatg aagcaattta aaaacaccaa aaaggccaaa caaaaaacaa ataacaatga     1320
gtaggtttta ggagaagcat gtattgattc ttggtatagt tgagtttatt tatattttca     1380
ttagccaatc actttttcta atttaactaa aaatgttata ataccttccc cacctagatg     1440
atgagataat catggaccca aaaacctcag ttttaaaaa tgtttattca ccaaaagaca      1500
aaaacaataa taataatcaa aagtagagta aaagaagaga gaagtgacat tcttttttctt    1560
tagctcataa tttctctaac aaatgcttct tttatccaaa ctctgatcat tgagtccagt     1620
tgggtaatga gagacaccag ctgggtttct tttgtttaag ctcacaaaca tctaaaacag     1680
agaaagcttt gtcatttttc tttaccctga aaccatgaaa gaagataaag ctttgtcctt    1740
tttctctttt ccgtttcttt actctcaaca atgtcttctt tctcccattg caacaaccac    1800
tgggtttggt tcatcttgtc ctcttgcgtc ttaagtaaga aaaagaaaa aagctttgcg     1860
tttgggacta tgtcacagct tcttgttctt cttgtggatg gtttcaagaa ctcaactatg    1920
agattgttgt tgatagagtt ttagtttttgg gtttgaagag atctgaattt cttcagctga   1980
atctgagatt aggagtcgaa                                                  2000
```

<210> SEQ ID NO 14
<211> LENGTH: 34
<212> TYPE: DNA
<213> ORGANISM: artificial sequence
<220> FEATURE:
<223> OTHER INFORMATION: pAtCHK2_F

<400> SEQUENCE: 14
taatttgaat atttatattc aatttcatac atat                                  34

<210> SEQ ID NO 15
<211> LENGTH: 23
<212> TYPE: DNA
<213> ORGANISM: artificial sequence
<220> FEATURE:
<223> OTHER INFORMATION: pAtCHK2_R

<400> SEQUENCE: 15
ttcgactcct aatctcagat tca                                              23

<210> SEQ ID NO 16
<211> LENGTH: 26
<212> TYPE: DNA
<213> ORGANISM: artificial sequence
<220> FEATURE:
<223> OTHER INFORMATION: pAtCHK4_F

<400> SEQUENCE: 16
ccaattcacg ttaaatctat ctcttg                                           26

<210> SEQ ID NO 17
<211> LENGTH: 26
<212> TYPE: DNA
<213> ORGANISM: artificial sequence
<220> FEATURE:
<223> OTHER INFORMATION: pAtCHK4_R

<400> SEQUENCE: 17
cacttcaaat gtaggtattc catttt                                           26

<210> SEQ ID NO 18
<211> LENGTH: 26
<212> TYPE: DNA
<213> ORGANISM: artificial sequence
<220> FEATURE:
<223> OTHER INFORMATION: AtCHK2_F_CDS

<400> SEQUENCE: 18
atgtctataa cttgtgagct cttgaa                                           26

<210> SEQ ID NO 19
<211> LENGTH: 24
<212> TYPE: DNA
<213> ORGANISM: artificial sequence
<220> FEATURE:
<223> OTHER INFORMATION: AtCHK2_R_CDS

<400> SEQUENCE: 19
ttaacaaggt tcaaagaatc ttgc                                             24

<210> SEQ ID NO 20
<211> LENGTH: 55
<212> TYPE: DNA
<213> ORGANISM: artificial sequence
<220> FEATURE:
<223> OTHER INFORMATION: AtCHK2_F_CDS_attB1F

<400> SEQUENCE: 20
ggggacaagt ttgtacaaaa aagcaggcta tgtctataac ttgtgagctc ttgaa           55

<210> SEQ ID NO 21
<211> LENGTH: 53
<212> TYPE: DNA
<213> ORGANISM: artificial sequence
<220> FEATURE:
<223> OTHER INFORMATION: AtCHK2_R_CDS_attB2R

<400> SEQUENCE: 21
ggggaccact tgtacaaga aagctgggtt taacaaggtt caaagaatct tgc    53

<210> SEQ ID NO 22
<211> LENGTH: 32
<212> TYPE: DNA
<213> ORGANISM: artificial sequence
<220> FEATURE:
<223> OTHER INFORMATION: AtCHK4_F_CDS

<400> SEQUENCE: 22
atgagaagag attttgtgta taataataat gc    32

<210> SEQ ID NO 23
<211> LENGTH: 22
<212> TYPE: DNA
<213> ORGANISM: artificial sequence
<220> FEATURE:
<223> OTHER INFORMATION: AtCHK4_R_CDS

<400> SEQUENCE: 23
ttacgacgaa ggtgagatag ga    22

<210> SEQ ID NO 24
<211> LENGTH: 61
<212> TYPE: DNA
<213> ORGANISM: artificial sequence
<220> FEATURE:
<223> OTHER INFORMATION: AtCHK4_F_CDS_attB1F

<400> SEQUENCE: 24
ggggacaagt ttgtacaaaa aagcaggcta tgagaagaga ttttgtgtat aataataatg    60
c    61

<210> SEQ ID NO 25
<211> LENGTH: 51
<212> TYPE: DNA
<213> ORGANISM: artificial sequence
<220> FEATURE:
<223> OTHER INFORMATION: AtCHK4_R_CDS_attB2R

<400> SEQUENCE: 25
ggggaccact tgtacaaga aagctgggtt tacgacgaag gtgagatagg a    51

<210> SEQ ID NO 26
<211> LENGTH: 22
<212> TYPE: DNA
<213> ORGANISM: artificial sequence
<220> FEATURE:
<223> OTHER INFORMATION: Q_CHK4_ F

<400> SEQUENCE: 26
taagcctgtt agagctgctg tg    22

<210> SEQ ID NO 27
<211> LENGTH: 20
<212> TYPE: DNA
<213> ORGANISM: artificial sequence
<220> FEATURE:
<223> OTHER INFORMATION: Q_CHK4_ R

<400> SEQUENCE: 27
tctttcaaac gcagcagctg    20

<210> SEQ ID NO 28
<211> LENGTH: 22
<212> TYPE: DNA
<213> ORGANISM: artificial sequence
<220> FEATURE:
<223> OTHER INFORMATION: Q_CHK2_F

<400> SEQUENCE: 28
gctacagaag aacagcgtgt tg                                            22

<210> SEQ ID NO 29
<211> LENGTH: 20
<212> TYPE: DNA
<213> ORGANISM: artificial sequence
<220> FEATURE:
<223> OTHER INFORMATION: Q_CHK2_R

<400> SEQUENCE: 29
tgtttgctgg caagttggtg                                               20

<210> SEQ ID NO 30
<211> LENGTH: 3708
<212> TYPE: DNA
<213> ORGANISM: Solanum lycopersicum

<400> SEQUENCE: 30
atgtccttaa attgcaaatt gttgggcatg aatgggagct tctcttcaag ttttaggttg    60
aagaaggcca gagagtcttt gccaggacca agttgtgggt ggaaatggca aaggaagctt   120
ttgtttttat ggctcatttt ctttggaatt ggatttttt ggttggtcat tagcttaaat    180
ggtgatgttt atagttggaa gaaggaggcg tcagaactaa atgaagataa atcttatttt   240
cttcttgaac gtttcaatgt cagcaaggaa caaattcaag atttagctac cttattcttt   300
gaaaaagatc agatttcatc cttggaatgc tcaaaagttc ataagcacga aatgcctatg   360
agtactacca ttacttgcct tctcaaggtg ctaggttcgg agagtctgga atatgaacag   420
catgagatgg ttgtagacaa tattgaagca aaggccagt gcccagttcc agatgaggag    480
acactgaaaa atagtgacat ttcactagat gaaaagtcgt taccatttgt tttgcatcgt   540
ttatcttctc taatctcaac agatcctaag ttctttgaaa agaaagcatc acaaataaga   600
gaagttggga attttaaccc agagcattgt gatagtattg ccttctgttt cacaaaaacta   660 tgctggtggg tccttcttgg gattgtgatc agttggaaga tacttctgtt atgtgcaaaa   720
ggtggggaac atcaacagaa cggattcatt cagcagcaac cactctctca caacttcat    780 ccactacagc agttgcagca gcagcaagtt cagatttcct gtcgaactgg tggaaagtgg   840
aggaaaaagg ctcttgttat ctttgtcttt ggtggggtga ctctagccat ctggttgtat   900
ttgtacctga gtgcagacat tgcattgagg aggaaagaaa cactgacaag catgtgtgac   960
gaacgagcgc gaatgttgca ggaccagttc aacgtaagca tgaaccatgt tcatgcattg  1020
gctattcttg tttccacatt tcaccatgga aaacaacctt ctgcaataga ccagaaaact  1080
tttgaagaat atactgagag aacagctttc gaaaggccac ttacaagtgg tgttgcctat  1140
gctttaagag ttcgtcactc agagagagaa gagtttgaga agctgcatgg gtggactata  1200
aagaaaatgg aagcagagga ccaaacttta ggacatgatt atatccctgc aaacttggat  1260
cctgctcctg atcaagatga atatgcgcct gtcatatttt cacaacaaac agtttcccat  1320
atcgtctcta ttgatatgat gtctggaaag gaagatcgtg agaacatttt gcagcgagg   1380 gcttctggca agggggtttt gacgtcaccg tttaagctat tgaaatccaa tcacctgggt  1440

```
gttgttctta catttgcggt ctataatact catctccttc cttatgctac cccggtggac    1500
cgcatcaatg ctactgttgg gtacattggt gcttcttacg atgttccatc attagttgaa    1560
aagcttctgc agcagcttgc gagcaaacaa actattgtgg taaatgttta tgatacaact    1620
aacaagtttg ctccaattaa aatgtatggc atggatgaga acgacacagg attacttcac    1680
gttagcaacc ttgattttgg ggatcctgca aggagccacg agatgcattg caggttcaag    1740
cagaaacctt ctccaccctg gactgcaata actctatctg tcggagtcct tgttatcact    1800
ctgcttattg gtcatatctt ccatgctgcc atcaacagaa ttgctgaagt tgagggtcag    1860
tatcaggaaa tgatggagct caaacatcgt gctgaggctg cagatatagc aaaatcacag    1920
tttcttgcaa cggtttctca tgaaatcagg actccaatga atggtgtttt aggcatgctt    1980
cagatgctca tggacacgaa ccttgaccta acgcaactgg attatgcaca aactgctctt    2040
agtagtggga atgaactgat atcattgatt aatgaggtgc tggatcaggc taagattgaa    2100
tcaggaaggc ttgagctgga ggctgttcct tttgatctcc gtgctgaact tgataatgtt    2160
tcatcgctct tctcgggaaa atctcataaa aagggattg agttggctgt ttatgtttct    2220
gacctagtcc cagaagttgt tatcggagat tcaggacggt tcaagcagat aattacgaat    2280
ctagttggaa actcagttaa gttcacaaat gacaaagggc acatatttgt cacagtacat    2340
ttagctgatg aagtgaggaa ccctcatgat gtgacggatg aagtcttgaa acaaagctta    2400
acctttgttc aagaaaggtc aaatgcatct tggaatacct tcagtgggtt tcctgtagtt    2460
gacagatggc aaagttggca aaagtttgat aggctgagca gcacagagga agaagtggga    2520
aagatcaagt tgttagtgac catagaagac actggtgtgg gaattcctct tgaagcacag    2580
gcccgcattt tcacaccttt tatgcaggct gacagttcaa catctcgaac atatggcgga    2640
acagggatag gattgagcat tagcaaacgt ttggtagacc tcatgggggg agaaataggc    2700
tttttcagtg aacctggcag agggagtaca ttttcattca ctgcagcctt cacaagagga    2760
gaagaaggtt ctttagagcg taaatggaaa cagtatgatc cagcttttcc agaatttcgt    2820
gggttaagag cattggtggt tgatgataaa agcattaggg cagtggtcac aagataccat    2880
ttgcagagac tgggtatatg tgtcaacata acttccacaa tgcgttcagc atgctctatat   2940 ctctctaatt actccaatac tagttcgttg gaacatttag ccgtggtttt tgttgaccaa    3000
gatagttggg ataaagaaac ttctcttgca ctaagtaata tgttgaaaga ggtcagacca    3060
aatggctcaa ctactacttt ggggaagcct ccaaaaatct gtctcttatg tatgaacttt    3120
atggagagag ctgagcttaa aatagctgga attgtggatc acgtgttaac aaagcctgtg    3180
cggttgagtg cgttgataac atgtgttcaa gaagccattg gctgccaaaa taagaagcaa    3240
gtgactcaac ctacaactct tggaagtttg ctgacaggaa agcatatatt ggtggtagat    3300
gacaataatg taaacaggag agtggcagaa ggtgctctaa agaagtatgg ggcgatagtg    3360
acctgtgtag acagtggaaa ggctgctttg acacatctta atccaccaca caagtttgat    3420
gcttgtttta tggacctcca aatgcctgaa atggatgggt ttgaagcgac acgacaaata    3480
cgtaatctag aaaacaaata taatgaaaag gtcaattctg gtgagttatt ttccggcatg    3540
tctgccagag tggctcattg gcacacacca atattagcaa tgcagcagaa tgtaattcaa    3600
gcaacaaatg aagagtgcgt gaagtgcggt atggatgatt atgtatcaaa accgtttgaa    3660
aaagggcagc tttattcaac agtggcacgc ttctttgggt caggttga              3708
```

<210> SEQ ID NO 31

<211> LENGTH: 1235
<212> TYPE: PRT
<213> ORGANISM: Solanum lycopersicum

<400> SEQUENCE: 31

```
Met Ser Leu Asn Cys Lys Leu Leu Gly Met Asn Gly Ser Phe Ser Ser
1               5                   10                  15

Ser Phe Arg Leu Lys Lys Ala Arg Glu Ser Leu Pro Gly Pro Ser Cys
                20                  25                  30

Gly Trp Lys Trp Gln Arg Lys Leu Phe Leu Trp Leu Ile Phe Phe
            35                  40                  45

Gly Ile Gly Phe Phe Trp Leu Val Ile Ser Leu Asn Gly Asp Val Tyr
        50                  55                  60

Ser Trp Lys Lys Glu Ala Ser Glu Leu Asn Glu Asp Lys Ser Tyr Phe
65                  70                  75                  80

Leu Leu Glu Arg Phe Asn Val Ser Lys Glu Gln Ile Gln Asp Leu Ala
                85                  90                  95

Thr Leu Phe Phe Glu Lys Asp Gln Ile Ser Ser Leu Glu Cys Ser Lys
            100                 105                 110

Val His Lys His Glu Met Pro Met Ser Thr Thr Ile Thr Cys Leu Leu
        115                 120                 125

Lys Val Leu Gly Ser Glu Ser Leu Glu Tyr Glu Gln His Glu Met Val
130                 135                 140

Val Asp Asn Ile Glu Ala Glu Gly Gln Cys Pro Val Pro Asp Glu Glu
145                 150                 155                 160

Thr Leu Lys Asn Ser Asp Ile Ser Leu Asp Glu Lys Ser Leu Pro Phe
                165                 170                 175

Val Leu His Arg Leu Ser Ser Leu Ile Ser Thr Asp Pro Lys Phe Phe
            180                 185                 190

Glu Lys Lys Ala Ser Gln Ile Arg Glu Val Gly Asn Phe Asn Pro Glu
        195                 200                 205

His Cys Asp Ser Ile Ala Phe Cys Phe Thr Lys Leu Cys Trp Trp Val
210                 215                 220

Leu Leu Gly Ile Val Ile Ser Trp Lys Ile Leu Leu Leu Cys Ala Lys
225                 230                 235                 240

Gly Gly Glu His Gln Gln Asn Gly Phe Ile Gln Gln Gln Pro Leu Ser
                245                 250                 255

Gln Gln Leu His Pro Leu Gln Gln Leu Gln Gln Gln Val Gln Ile
            260                 265                 270

Ser Cys Arg Thr Gly Gly Lys Trp Arg Lys Ala Leu Val Ile Phe
        275                 280                 285

Val Phe Gly Gly Val Thr Leu Ala Ile Trp Leu Tyr Leu Tyr Leu Ser
290                 295                 300

Ala Asp Ile Ala Leu Arg Arg Lys Glu Thr Leu Thr Ser Met Cys Asp
305                 310                 315                 320

Glu Arg Ala Arg Met Leu Gln Asp Gln Phe Asn Val Ser Met Asn His
                325                 330                 335

Val His Ala Leu Ala Ile Leu Val Ser Thr Phe His His Gly Lys Gln
            340                 345                 350

Pro Ser Ala Ile Asp Gln Lys Thr Phe Glu Glu Tyr Thr Glu Arg Thr
        355                 360                 365

Ala Phe Glu Arg Pro Leu Thr Ser Gly Val Ala Tyr Ala Leu Arg Val
370                 375                 380

Arg His Ser Glu Arg Glu Glu Phe Glu Lys Leu His Gly Trp Thr Ile
```

```
            385                 390                 395                 400
Lys Lys Met Glu Ala Glu Asp Gln Thr Leu Gly His Asp Tyr Ile Pro
                405                 410                 415
Ala Asn Leu Asp Pro Ala Pro Asp Gln Asp Glu Tyr Ala Pro Val Ile
                420                 425                 430
Phe Ser Gln Gln Thr Val Ser His Ile Val Ser Ile Asp Met Met Ser
                435                 440                 445
Gly Lys Glu Asp Arg Glu Asn Ile Leu Arg Ala Arg Ala Ser Gly Lys
    450                 455                 460
Gly Val Leu Thr Ser Pro Phe Lys Leu Lys Ser Asn His Leu Gly
465                 470                 475                 480
Val Val Leu Thr Phe Ala Val Tyr Asn Thr His Leu Leu Pro Tyr Ala
                485                 490                 495
Thr Pro Val Asp Arg Ile Asn Ala Thr Val Gly Tyr Ile Gly Ala Ser
                500                 505                 510
Tyr Asp Val Pro Ser Leu Val Glu Lys Leu Leu Gln Gln Leu Ala Ser
            515                 520                 525
Lys Gln Thr Ile Val Val Asn Val Tyr Asp Thr Thr Asn Lys Phe Ala
            530                 535                 540
Pro Ile Lys Met Tyr Gly Met Asp Glu Asn Asp Thr Gly Leu Leu His
545                 550                 555                 560
Val Ser Asn Leu Asp Phe Gly Asp Pro Ala Arg Ser His Glu Met His
                565                 570                 575
Cys Arg Phe Lys Gln Lys Pro Ser Pro Pro Trp Thr Ala Ile Thr Leu
                580                 585                 590
Ser Val Gly Val Leu Val Ile Thr Leu Leu Ile Gly His Ile Phe His
            595                 600                 605
Ala Ala Ile Asn Arg Ile Ala Glu Val Glu Gly Gln Tyr Gln Glu Met
            610                 615                 620
Met Glu Leu Lys His Arg Ala Glu Ala Ala Asp Ile Ala Lys Ser Gln
625                 630                 635                 640
Phe Leu Ala Thr Val Ser His Glu Ile Arg Thr Pro Met Asn Gly Val
                645                 650                 655
Leu Gly Met Leu Gln Met Leu Met Asp Thr Asn Leu Asp Leu Thr Gln
                660                 665                 670
Leu Asp Tyr Ala Gln Thr Ala Leu Ser Ser Gly Asn Glu Leu Ile Ser
            675                 680                 685
Leu Ile Asn Glu Val Leu Asp Gln Ala Lys Ile Glu Ser Gly Arg Leu
    690                 695                 700
Glu Leu Glu Ala Val Pro Phe Asp Leu Arg Ala Glu Leu Asp Asn Val
705                 710                 715                 720
Ser Ser Leu Phe Ser Gly Lys Ser His Lys Lys Gly Ile Glu Leu Ala
                725                 730                 735
Val Tyr Val Ser Asp Leu Val Pro Glu Val Val Ile Gly Asp Ser Gly
            740                 745                 750
Arg Phe Lys Gln Ile Ile Thr Asn Leu Val Gly Asn Ser Val Lys Phe
            755                 760                 765
Thr Asn Asp Lys Gly His Ile Phe Val Thr Val His Leu Ala Asp Glu
            770                 775                 780
Val Arg Asn Pro His Asp Val Thr Asp Glu Val Leu Lys Gln Ser Leu
785                 790                 795                 800
Thr Phe Val Gln Glu Arg Ser Asn Ala Ser Trp Asn Thr Phe Ser Gly
                805                 810                 815
```

-continued

Phe Pro Val Val Asp Arg Trp Gln Ser Trp Gln Lys Phe Asp Arg Leu
        820                 825                 830

Ser Ser Thr Glu Glu Val Gly Lys Ile Lys Leu Leu Val Thr Ile
        835                 840                 845

Glu Asp Thr Gly Val Gly Ile Pro Leu Glu Ala Gln Ala Arg Ile Phe
        850                 855                 860

Thr Pro Phe Met Gln Ala Asp Ser Ser Thr Ser Arg Thr Tyr Gly Gly
865                 870                 875                 880

Thr Gly Ile Gly Leu Ser Ile Ser Lys Arg Leu Val Asp Leu Met Gly
            885                 890                 895

Gly Glu Ile Gly Phe Phe Ser Glu Pro Gly Arg Gly Ser Thr Phe Ser
            900                 905                 910

Phe Thr Ala Ala Phe Thr Arg Gly Glu Glu Gly Ser Leu Glu Arg Lys
            915                 920                 925

Trp Lys Gln Tyr Asp Pro Ala Phe Pro Glu Phe Arg Gly Leu Arg Ala
        930                 935                 940

Leu Val Val Asp Asp Lys Ser Ile Arg Ala Val Val Thr Arg Tyr His
945                 950                 955                 960

Leu Gln Arg Leu Gly Ile Cys Val Asn Ile Thr Ser Thr Met Arg Ser
                965                 970                 975

Ala Cys Ser Tyr Leu Ser Asn Tyr Ser Asn Thr Ser Ser Leu Glu His
            980                 985                 990

Leu Ala Val Val Phe Val Asp Gln Asp Ser Trp Asp Lys Glu Thr Ser
            995                 1000                1005

Leu Ala Leu Ser Asn Met Leu Lys Glu Val Arg Pro Asn Gly Ser
     1010                1015                 1020

Thr Thr Thr Leu Gly Lys Pro Pro Lys Ile Cys Leu Leu Cys Met
     1025                1030                 1035

Asn Phe Met Glu Arg Ala Glu Leu Lys Ile Ala Gly Ile Val Asp
     1040                1045                 1050

His Val Leu Thr Lys Pro Val Arg Leu Ser Ala Leu Ile Thr Cys
     1055                1060                 1065

Val Gln Glu Ala Ile Gly Cys Gln Asn Lys Lys Gln Val Thr Gln
     1070                1075                 1080

Pro Thr Thr Leu Gly Ser Leu Leu Thr Gly Lys His Ile Leu Val
     1085                1090                 1095

Val Asp Asp Asn Asn Val Asn Arg Arg Val Ala Glu Gly Ala Leu
     1100                1105                 1110

Lys Lys Tyr Gly Ala Ile Val Thr Cys Val Asp Ser Gly Lys Ala
     1115                1120                 1125

Ala Leu Thr His Leu Asn Pro Pro His Lys Phe Asp Ala Cys Phe
     1130                1135                 1140

Met Asp Leu Gln Met Pro Glu Met Asp Gly Phe Glu Ala Thr Arg
     1145                1150                 1155

Gln Ile Arg Asn Leu Glu Asn Lys Tyr Asn Glu Lys Val Asn Ser
     1160                1165                 1170

Gly Glu Leu Phe Ser Gly Met Ser Ala Arg Val Ala His Trp His
     1175                1180                 1185

Thr Pro Ile Leu Ala Met Thr Ala Asp Val Ile Gln Ala Thr Asn
     1190                1195                 1200

Glu Glu Cys Val Lys Cys Gly Met Asp Asp Tyr Val Ser Lys Pro
     1205                1210                 1215

```
Phe Glu Lys Gly Gln Leu Tyr Ser Thr Val Ala Arg Phe Phe Gly
    1220                1225                1230

Ser Gly
    1235

<210> SEQ ID NO 32
<211> LENGTH: 6097
<212> TYPE: DNA
<213> ORGANISM: artificial sequence
<220> FEATURE:
<223> OTHER INFORMATION: expression cassette SlyCHK2

<400> SEQUENCE: 32
ggggacaact tgtatagaa  aagttgagtt tatcaatatt ttgagatttt tatatattta      60
cattagtaat tttcttaata ataatctcca gaatttataa ttattttatt aattactcta     120
ccatcgaata ttttttattg gttgttctaa tttccttgtc actttcaact tgtaattgac     180
caaaagaaat attttagctt agataagttt cttacatcat atttcctctc tcttttata      240 tgctttattt gtataggagt ttattatttt ttatatagtg tttggagctt atattaaatt     300
tggatcgcac actgtaaaga ttcatataaa gtgatgcttc gaacaagttt ttctctatat     360
ctaagctcga aattattttt ctccatacac gaaactcaaa tccgaaatat ttaattaaag     420
tgaatcagtt tcaccccaat accataacca taaatcatgt tgattagttg ctatcaactt     480
ctttcttcat gttcaaatgt ttttttttaat gaaaaggtat taataattca catgcattca    540
tcaactagct taatttaatt ttattttgat aaataattca ataacaattt ctactacaat     600
tgactcattc aaggattta catataatgc aaactcacct atatgtattt attaagcaca      660
caatagttgt ttagaatcac aagaaatcat ataatgatgg tcaaactaat catgtctttt    720
taatattaaa agtgattagt tttatctaac actattaaac ataccaattc atttattatt    780
atattaaata atattattcc ccttattttt tttttagta atttaaaaca cattagggtt     840
attattaggg agaagtgggg ttggagagat gaggtgcatt agccagccaa ctggatgcc     900 cacatcatca attatcttcc aagaataaag tgtaggataa gcatctcaag tagccggcgc    960 atttagtac ctagcccttg ctttattatt attttttcac gccgattaat cgccgatctt    1020
ttgtagttcg tacgccgtat tatcaaaagc atagatgctt ttttttttta aaaataaatt    1080
tatttttaaa ttttaatttt ttttttgttct tttctccatg tgaaatgaac aaatacaact   1140
ggctagctct tcccacaacc atcccttttc tttttttttc tttctttttc tcctctccca    1200
ttctttatat ttattatgcc tagccatata tttatatttt gttcgtttga tttatgtgat    1260
gttatttgat tagatgttaa aattttaaaa tataattata tttataatat tttaaattat    1320
tcttaaaaaa ataaattta aatattttt tatcaaataa gtgagagcaa acatgcgata     1380
gcgttattaa attctgataa gtaagaaaaa atatgaattt aaaaataaac atgtaatata    1440
aattagaata aaaagtatt attttttcta atcgaaggca atatttcgag gggaaaaacc     1500
ctatatagac ctatgtgaga tgattttgaa ttagtaagaa tccaatgtgc ccgacatcga    1560
atgttttttt tttaaaaata tttacagtta cattatattg aaactgaaaa gggacagtga    1620
aggaatggag ctatcttaaa aagcaaagaa aactatcttt ttattattt tactatatag     1680 acaagaaaag aaatatggta acaaaaattt gcatattgtg gaagtgtaaa catttgagaa    1740
atgcataatt ttcggggaaa gatgatgatc gaaattttgg agatatatct taattaaatt    1800
aaggacatat tattttaaat atatattttt ttgtaattt gtgcatcttt ttgatgtacg     1860
tgacatttaa atattttcca catgcctcaa ttgcgtgaaa ttatggagtg tgtcacgtaa    1920
```

```
gacaaaaaat atacaaaata ataataaaat aatttaagaa taataaaacc tcaatataat    1980
taatgtgtat atatgaaatt ttaatcataa tttaagaggt atttgtatga gcttttctgc    2040
tctgagtggg tttgctctta agttttcaag gcattttttg aagatatgta ggtggattct    2100
attaaagatg tccttaaatt gcaaattgtt gggcatgaat gggagcttct cttcaagttt    2160
taggttgaag aaggccagag agtctttgcc aggaccaagt tgtgggtgga aatggcaaag    2220
gaagcttttg tttttatggc tcattttctt tggaattgga tttttttggt tggtcattag    2280
cttaaatggt gatgtttata gttggaagaa ggaggcgtca gaactaaatg aagataaatc    2340
ttattttctt cttgaacgtt tcaatgtcag caaggaacaa attcaagatt tagctacctt    2400
attctttgaa aaagatcaga tttcatcctt ggaatgctca aaagttcata agcacgaaat    2460
gcctatgagt actaccatta cttgccttct caaggtgcta ggttcggaga gtctggaata    2520
tgaacagcat gagatggttg tagacaatat tgaagcagaa ggccagtgcc cagttccaga    2580
tgaggagaca ctgaaaaata gtgacatttc actagatgaa aagtcgttac catttgtttt    2640
gcatcgttta tcttctctaa tctcaacaga tcctaagttc tttgaaaaga aagcatcaca    2700
aataagagaa gttgggaatt ttaacccaga gcattgtgat agtattgcct tctgtttcac    2760
aaaactatgc tggtgggtcc ttcttgggat tgtgatcagt tggaagatac ttctgttatg    2820 tgcaaaggt ggggaacatc aacagaacgg attcattcag cagcaaccac tctctcaaca    2880
acttcatcca ctacagcagt tgcagcagca gcaagttcag atttcctgtc gaactggtgg    2940
aaagtggagg aaaaaggctc ttgttatctt tgtctttggt ggggtgactc tagccatctg    3000
gttgtatttg tacctgagtg cagacattgc attgaggagg aaagaaacac tgacaagcat    3060
gtgtgacgaa cgagcgcgaa tgttgcagga ccagttcaac gtaagcatga accatgttca    3120
tgcattggct attcttgttt ccacatttca ccatggaaaa caaccttctg caatagacca    3180
gaaaactttt gaagaatata ctgagagaac agctttcgaa aggccactta caagtggtgt    3240
tgcctatgct ttaagagttc gtcactcaga gagagaagag tttgagaagc tgcatgggtg    3300
gactataaag aaaatggaag cagaggacca aactttagga catgattata tccctgcaaa    3360
cttggatcct gctcctgatc aagatgaata tgcgcctgtc atattttcac aacaaacagt    3420
ttcccatatc gtctctattg atatgatgtc tggaaaggaa gatcgtgaga acattttgcg    3480
agcgagggct tctggcaagg ggttttgac gtcaccgttt aagctattga aatccaatca    3540
cctgggtgtt gttcttacat ttgcggtcta taatactcat ctccttcctt atgctacccc    3600
ggtggaccgc atcaatgcta ctgttgggta cattggtgct tcttacgatg ttccatcatt    3660
agttgaaaag cttctgcagc agcttgcgag caaacaaact attgtggtaa atgtttatga    3720
tacaactaac aagtttgctc caattaaaat gtatggcatg gatgagaacg acacaggatt    3780
acttcacgtt agcaaccttg attttgggga tcctgcaagg agccacgaga tgcattgcag    3840
gttcaagcag aaaccttctc caccctggac tgcaataact ctatctgtcg gagtccttgt    3900
tatcactctg cttattggtc atatcttcca tgctgccatc aacagaattg ctgaagttga    3960
gggtcagtat caggaaatga tggagctcaa acatcgtgct gaggctgcag atatagcaaa    4020
atcacagttt cttgcaacgg tttctcatga aatcaggact ccaatgaatg tgttttagg    4080 catgcttcag atgctcatgg acacgaacct tgacctaacg caactggatt atgcacaaac    4140
tgctcttagt agtgggaatg aactgatatc attgattaat gaggtgctgg atcaggctaa    4200
gattgaatca ggaaggcttg agctggaggc tgttcctttt gatctccgtg ctgaacttga    4260
```

```
taatgtttca tcgctcttct cgggaaaatc tcataaaaaa gggattgagc agttggctgt    4320
ttatgtttct gacctagtcc cagaagttgt tatcggagat tcaggacggt tcaagcagat    4380
aattacgaat ctagttggaa actcagttaa gttcacaaat gacaaagggc acatatttgt    4440
cacagtacat ttagctgatg aagtgaggaa ccctcatgat gtgacggatg aagtcttgaa    4500
acaaagctta acctttgttc aagaaaggtc aaatgcatct tggaatacct tcagtgggtt    4560
tcctgtagtt gacagatggc aaagttggca aaagtttgat aggctgagca gcacagagga    4620
agaagtggga aagatcaagt tgttagtgac catagaagac actggtgtgg gaattcctct    4680
tgaagcacag gcccgcattt tcacaccttt tatgcaggct gacagttcaa catctcgaac    4740
atatggcgga acagggatag gattgagcat tagcaaacgt ttggtagacc tcatgggggg    4800
agaaataggc tttttcagtg aacctggcag agggagtaca ttttcattca ctgcagcctt    4860
cacaagagga gaagaaggtt ctttagagcg taaatggaaa cagtatgatc cagcttttcc    4920
agaatttcgt gggttaagag cattggtggt tgatgataaa agcattaggg cagtggtcac    4980
aagataccat ttgcagagac tgggtatatg tgtcaacata acttccacaa tgcgttcagc    5040
atgctcatat ctctctaatt actccaatac tagttcgttg gaacatttag ccgtggtttt    5100
tgttgaccaa gatagttggg ataaagaaac ttctcttgca ctaagtaata tgttgaaaga    5160
ggtcagacca aatggctcaa ctactacttt ggggaagcct ccaaaaatct gtctcttatg    5220
tatgaacttt atggagagag ctgagcttaa aatagctgga attgtggatc acgtgttaac    5280
aaagcctgtg cggttgagtg cgttgataac atgtgttcaa gaagccattg gctgccaaaa    5340
taagaagcaa gtgactcaac ctacaactct tggaagtttg ctgacaggaa agcatatatt    5400
ggtggtagat gacaataatg taaacaggag agtggcagaa ggtgctctaa agaagtatgg    5460
ggcgatagtc acctgtgtag acagtggaaa ggctgctttg acacatctta atccaccaca    5520
caagtttgat gcttgtttta tggacctcca aatgcctgaa atggatgggt ttgaagcgac    5580
acgacaaata cgtaatctag aaaacaaata taatgaaaag gtcaattctg gtgagttatt    5640
ttccggcatg tctgccagag tggctcattg gcacacacca atattagcaa tgacagcaga    5700
tgtaattcaa gcaacaaatg aagagtgcgt gaagtgcggt atggatgatt atgtatcaaa    5760
accgtttgaa aaagggcagc tttattcaac agtggcacgc ttctttgggt caggttgaga    5820
tcgttcaaac atttggcaat aaagtttctt aagattgaat cctgttgccg gtcttgcgat    5880
gattatcata taatttctgt tgaattacgt taagcatgta ataattaaca tgtaatgcat    5940
gacgttattt atgagatggg tttttatgat tagagtcccg caattataca tttaatacgc    6000
gatagaaaac aaaatatagc gcgcaaacta ggataaatta tcgcgcgcgg tgtcatctat    6060
gttactagat cggggacaac tttgtataat aaagttg                            6097
```

SHOOT REGENERATION BY OVEREXPRESSION OF CHK GENES

CROSS-REFERENCE TO RELATED APPLICATIONS

This application is a continuation of International Application No. PCT/EP2019/058614 filed Apr. 5, 2019, which claims the benefit of and priority to European Application No. 18165895.6 filed Apr. 5, 2018, both of which are hereby incorporated by reference herein in their entireties.

SEQUENCE LISTING

The instant application contains a Sequence Listing which is being submitted in ASCII format via EFS-WEB and is hereby incorporated by reference in its entirety. Said ASCII copy, created on Apr. 5, 2019, is named 085342-3800SequenceListing.txt and is 96 kb.

FIELD OF THE INVENTION

The present invention relates to the field of molecular plant biology, in particular to the field of plant regeneration. The invention concerns methods for improving the regeneration capacity of plant cells.

BACKGROUND

Plant breeding aims to improve the productivity and performance of crop plants through selection and recombination of useful and superior traits, and to improve such plant traits by genetic technologies. These technologies are often faced with a central technical challenge: how to regenerate from a single cell back to a fertile plant. This is true both for techniques aimed at making genetic changes (mutagenesis, genome editing, genetic transformation) and for those affecting the genome as a whole (DH production, polyploidisation, somatic hybridisations). This is because the genetic or genomic changes realised occur in only one or a small number of cells, and never in all cells of an organism at once in exactly the same manner. Therefore, an important limitation of these current techniques is the identification and singling out of the desired cells, and subsequently growing them back to complete and fertile plants.

Techniques of genome improvement are hampered by the potential of in vitro regeneration of modified single cells into whole fertile plants. Regeneration typically passes through a stage whereby a single cell first undergoes sustained cell division to form a multicellular structure or callus. Subsequently, under the influence of exogenously supplied plant growth regulators, cells in the multicellular mass form organized structures. Hence regeneration involves at least two sequential critical steps, i.e. a step of cell division followed by a step of differentiation to form organized structures. The first step one may involve callus formation. The second step must involve de novo meristem formation.

In vitro plant regeneration follows one of two alternative pathways, organogenesis and somatic embryogenesis, both of which rely on the induction by plant growth regulators (Duclercq et al., 2011, TIPS 16: 597). Monocotyledonous and dicotyledonous plants can use either both or only one of these two alternative pathways to regenerate.

A common pathway of plant regeneration in dicotyledonous plants is organogenesis, in which de novo apical meristems are formed from undifferentiated cells. These meristems usually grow out to form shoots, which are then dissected from the underlying cell mass and induced to form roots. Organogenesis is typically induced in culture media containing cytokinins, or a mixture of auxins or cytokinins in which the cytokinins are often predominantly present. Cytokinins are a group of plant growth regulators or phytohormones, derivatives of adenine, and capable of promoting cell division (Mok and Mok, 2001, Annu. Rev. Plant Physiol. Plant Mol. Biol. 52: 89-118). The group encompasses naturally occurring cytokinins such as zeatin, and synthetic cytokinins such as kinetin and 6-benzylaminopurine (6-BAP).

Another regeneration pathway, often found in monocotyledonous and woody species, is through somatic embryogenesis, whereby undifferentiated cells in a callus, under proper conditions, generate embryogenic cells that ultimately form structures that resemble zygotic embryos, the so-called somatic embryos (Quiroz-Figueroa et al., 2006, PCTOC 86: 285-301). These somatic embryos are then capable of being converted into small plantlets, either spontaneous or under low concentrations of plant growth regulators. Embryogenic potential in callus or cell suspensions is typically induced by auxins, a group of naturally occurring or synthetic plant growth regulators.

A major bottleneck is the generally limited capacity of plant cells to regenerate into fertile and healthy plants. Regeneration potential is highly dependent on plant species, on variety and on tissue origin. Even with established protocols, the fraction of cells successfully regenerating to plants is usually quite low (Srinivasan et al., 2007, Planta 225: 341-351). Plant species or varieties in which the regeneration fails or the efficiency is poor are considered recalcitrant. Examples of crop species recalcitrant in organogenesis are pepper, soybean, cucumber and sugar beet.

In the past, recalcitrance has often been addressed by trial and error approaches through empirical variations in tissue culture conditions (media composition, light, temperature), and met with limited success. Protocols developed in this way are still dependent on genotype and laboratory conditions, and therefore to some extent unpredictable.

Regeneration through organogenesis or somatic embryogenesis can be enhanced by the ectopic expression of transgenes. An example of such approach is the overexpression of ESR1 (an AP2/EREBP transcription factor) in *Arabidopsis* (Banno et al., 2001, Plant Cell 13: 2609-2618), resulting in enhanced shoot regeneration from root explants. Another example is the overexpression of BBM, an AP2/ERF transcription factor, in tobacco (Srinivasan et al., 2007, Planta 225: 341-351), resulting in increased shoot formation and a higher competence for somatic embryogenesis. However, the constitutive expression of these transcription factors results in morphological and developmental defects, and these therefore require the controlled expression by exogenously supplied inducers (estradiol-inducible and dexamethasone-inducible system, respectively). The requirement of controlled expression thus currently limits the use of transgenes for regeneration.

Hence, there is still a need in the art for improving the generation capacity of a plant, especially for improving the generation capacity of a plant having a low or insufficient regeneration capacity. In particular, there is also a need in the art to improve the regeneration capacity of a plant, without requiring the controlled expression of transgenes.

SUMMARY OF THE INVENTION

In a first aspect, the invention pertains to a method for improving a cytokinin-induced regeneration capacity of a plant cell, wherein the method comprises a step of increasing or introducing the expression of a histidine kinase in the plant cell and wherein the histidine kinase is at least one of CHK2, CHK3 and CHK4, wherein preferably the histidine kinase is at least one of CHK2 and CHK4, preferably wherein the histidine kinase is CHK4.

In one embodiment, the histidine kinase is encoded by a nucleotide sequence having at least 50% sequence identity with at least one of SEQ ID NO: 1, SEQ ID NO:2 and SEQ ID NO: 3, wherein preferably the nucleotide sequence has at least 50% sequence identity with SEQ ID NO: 3.

Preferably, the regeneration capacity of the plant cell is improved as compared to an identical plant cell not having an increased or introduced expression of the histidine kinase.

In an embodiment, the amino acid sequence of the histidine kinase has at least 50% sequence identity with at least one of SEQ ID NO: 4, SEQ ID NO: 5 and SEQ ID NO: 6, wherein preferably the amino acid sequence of the histidine kinase has at least 50% sequence identity with SEQ ID NO: 6

Preferably, the expression of the histidine kinase is transiently increased or introduced into the plant cell.

In one embodiment of the invention, the expression of the histidine kinase is continuously increased or introduced in the plant cell.

Preferably, the plant cell is obtainable from a plant selected from the group consisting of barley, cabbage, canola, cassava, cauliflower, chicory, cotton, cucumber, eggplant, grape, hot pepper, lettuce, maize, melon, oilseed rape, potato, pumpkin, rice, rye, *sorghum*, squash, sugar cane, sugar beet, sunflower, sweet pepper, tomato, water melon, wheat, zucchini, soybean, *chrysanthemum* and *Arabidopsis*.

In a further embodiment, the cytokinin is an adenine-type cytokinin, wherein preferably the adenine-type cytokinin is selected from the group consisting of kinetin, zeatin, trans-zeatin, cis-zeatin, dihydrozeatin, 6-benzylaminopurine and 2iP.

In a second aspect, the invention concerns a method for regenerating a plant comprising the steps of:
  incubating the plant cell as defined herein in a medium comprising a cytokinin; and
  allowing the plant cell to regenerate into a plant.

Preferably the medium comprises at least one further plant hormone, wherein preferably the one further plant hormone is an auxin.

In an embodiment, the plant cell is part of a multicellular tissue, preferably a callus tissue, a plant organ or an explant.

Preferably the explant is at least one of a hypocotyl explant, a stem explant, a cotyledon explant, a root explant, a leaf explant, a flower explant and a meristematic tissue.

In a further embodiment, the concentration cytokinin in the medium is about 100-3000 ng/ml, wherein preferably the concentration cytokinin is about 200-600 ng/ml.

In an embodiment of the invention, the improved cytokinin-induced regeneration capacity is selected from the group of an improved meristem formation, an improved adventitious shoot formation, an improved inflorescence formation, an improved somatic embryo formation, an improved root formation, an improved elongation of adventitious shoots and an improved regeneration of a complete plant.

In a third aspect, the invention relates to a plant or plant part obtainable by the method of the invention as defined herein, wherein preferably the plant part is a seed, a fruit or a non-propagating material.

In another aspect, the invention pertains to an expression construct comprising a first nucleotide sequence having at least 50% sequence identity with SEQ ID NO: 3 and a second nucleotide sequence having at least 50% sequence identity with SEQ ID NO: 1, wherein preferably at least one of the first and the second nucleotide sequence is operably linked to a regulatory element.

In a further aspect, the invention concerns the use of a CHK2, CHK3 and/or CHK4 histidine kinase or the expression construct as defined herein, for improving a cytokinin-induced regeneration capacity of a plant.

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein.

It is clear for the skilled person that any methods and materials similar or equivalent to those described herein can be used for practising the present invention.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al. Molecular Cloning. A Laboratory Manual, 2nd Edition, Cold Spring Harbor Laboratory Press, Cold Spring Harbor, N. Y., 1989; Ausubel et al. Current Protocols in Molecular Biology, John Wiley & Sons, New York, 1987 and periodic updates; and the series Methods in Enzymology, Academic Press, San Diego.

The singular terms "a," "an," and "the" include plural referents unless the context clearly dictates otherwise. Thus, for example, reference to "a cell" includes a combination of two or more cells, and the like. The indefinite article "a" or "an" thus usually means "at least one".

The term "and/or" refers to a situation wherein one or more of the stated cases may occur, alone or in combination with at least one of the stated cases, up to with all of the stated cases.

As used herein, the term "about" is used to describe and account for small variations. For example, the term can refer to less than or equal to ±(+ or −) 10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The term "comprising" is construed as being inclusive and open ended, and not exclusive. Specifically, the term and variations thereof mean the specified features, steps or components are included. These terms are not to be interpreted to exclude the presence of other features, steps or components.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein." An "isolated protein" is used to refer to a protein which is no longer in its natural environment, for example in vitro or in a recombinant bacterial or plant host cell.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing.

"Plant cell(s)" include protoplasts, gametes, suspension cultures, microspores, pollen grains, etc., either in isolation or within a tissue, organ or organism. The plant cell can e.g. be part of a multicellular structure, such as a callus, meristem, plant organ or an explant.

"Similar conditions" for culturing the plant/plant cells means among other things the use of a similar temperature, humidity, nutrition and light conditions, and similar irrigation and day/night rhythm.

The terms "homology", "sequence identity" and the like are used interchangeably herein. Sequence identity is herein defined as a relationship between two or more amino acid (polypeptide or protein) sequences or two or more nucleotide (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The percentage sequence identity/similarity can be determined over the full length of the sequence.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nlm.nih.gov/.

The terms "nucleic acid construct", "nucleic acid vector", "vector" and "expression construct" are used interchangeably herein and is herein defined as a man-made nucleic acid molecule resulting from the use of recombinant DNA technology. The terms "nucleic acid construct" and "nucleic acid vector" therefore does not include naturally occurring nucleic acid molecules although a nucleic acid construct may comprise (parts of) naturally occurring nucleic acid molecules.

The vector backbone may for example be a binary or superbinary vector (see e.g. U.S. Pat. No. 5,591,616, US 2002138879 and WO 95/06722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors can comprise further genetic elements to facilitate their use in molecular cloning, such as e.g. selectable markers, multiple cloning sites and the like.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3' non-translated sequence (3' end) comprising a polyadenylation site.

"Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked may mean that the DNA sequences being linked are contiguous.

"Promoter" refers to a nucleic acid fragment that functions to control the transcription of one or more nucleic acids. A promoter fragment is preferably located upstream (5') with respect to the direction of transcription of the transcription initiation site of the gene, and is structurally identified by the presence of a binding site for DNA-dependent RNA polymerase, transcription initiation site(s) and can further comprise any other DNA sequences, including, but not limited to transcription factor binding sites, repressor and activator protein binding sites, and any other sequences of nucleotides known to one of skill in the art to act directly or indirectly to regulate the amount of transcription from the promoter.

Optionally the term "promoter" may also include the 5' UTR region (5' Untranslated Region) (e.g. the promoter may herein include one or more parts upstream of the translation initiation codon of transcribed region, as this region may have a role in regulating transcription and/or translation). A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

The term "regeneration" is herein defined as the formation of a new tissue and/or a new organ from a single plant cell, a callus, an explant, a tissue or from an organ. A preferred regeneration pathway is organogenesis, i.e. the formation of new organs from (undifferentiated) cells. Preferably, the regeneration is at least one of ectopic apical meristem formation, shoot regeneration and root regeneration. The regeneration as defined herein can preferably concern at least de novo shoot formation. For example, regeneration can be the regeneration of a(n) (elongated) hypocotyl explant towards a(n) (inflorescence) shoot.

Regeneration may further include the formation of a new plant from a single plant cell or from e.g. a callus, an explant, a tissue or an organ. The regeneration process can occur directly from parental tissues or indirectly, e.g. via the formation of a callus.

The term "conditions that allow for regeneration" is herein understood as an environment wherein a plant cell or tissue can regenerate. Such conditions include at minimum a suitable temperature (i.e. between 0° C.-60° C.), nutrition, day/night rhythm, irrigation and the plant hormone cytokinin. These conditions can include one, two or three of the conditions specified in the examples. Furthermore, "optimal conditions that allow for regeneration" are those environmental conditions that allow for a maximum regeneration of the plant cells.

The terms "introduced expression" and "de novo expression" are used interchangeable herein.

DETAILED DESCRIPTION OF THE INVENTION

The inventors discovered that introducing or enhancing the expression of a histidine kinase in a plant cell increases the regeneration capacity of this plant cell when grown in a medium comprising a cytokinin. The regeneration potential surprisingly increased in comparison to unmodified plant cells grown in the same cytokinin-comprising medium. Introducing a histidine kinase in a plant cell thus significantly augments the effect of the cytokinin. This enhanced effect of increasing the expression of a histidine kinase in combination with growing the cells on cytokinin-comprising medium surprisingly increased the maximum ability of a cell to regenerate. The inventors thus discovered that introducing a histidine kinase into a plant cell can transform a plant cell having a poor regeneration capacity into a plant cell that can regenerate, when grown in a cytokinin-comprising medium.

Without wishing to be bound to any theory, histidine kinase genes such as CHK genes encoding the cytokinin receptor molecules, seem to render plants more sensitive, and consequently more responsive to cytokinin, resulting in greatly improved shoot regeneration capacity. CHK genes previously have been implicated in the cytokinin signal transduction (Kakimoto, 1996, Science 274: 982-985), and enhanced expression of CHK genes have been associated with functions attributed to cytokinin response, but not regeneration capacity (Deng et al., 2010, Plant Cell 22: 1232-1248).

WO02/099079, EP2272862, and Riefler M et al, (The Plant Cell, Vol. 18 (2006): p 40-54) concern cytokinin response regulators and uses thereof. These documents are however silent on the combination of expressing a histidine kinase and maintaining the cells in cytokinin-comprising medium. In particular, the inventors now show that expressing a histidine kinase in cells in combination with maintaining the cells in cytokinin-comprising medium can push the cells above their natural maximum ability to regenerate.

In a first aspect, the invention therefore pertains to a method for improving a cytokinin-induced regeneration capacity of a plant cell, wherein the method comprises a step of increasing or introducing the expression of a histidine kinase in the plant cell.

The plant cell may be a protoplast. A cytokinin-induced regeneration is defined herein as the regeneration of a plant cell when exposed to at least a cytokinin, e.g. the regeneration response of a plant cell when exposed to a cytokinin under conditions that allow for the regeneration of the plant cell.

The cytokinin-induced regeneration capacity of a plant cell is herein understood as the maximum potential of a plant cell to regenerate when exposed to at least the plant hormone cytokinin under conditions, preferably optimal conditions, that allow for the regeneration of the plant cell. It is well-known in the art that plant cells have a certain inherent maximum potential to regenerate in a medium comprising a cytokinin. For example, the maximum regeneration potential of a plant cell obtained from e.g. a tobacco plant is usually higher than the maximum regeneration potential of a plant cell obtained from e.g. a cucumber plant. The regeneration capacity of plant cells may be assessed by determining the number of de novo formed shoots on a multicellular tissue or tissues. As a non-limiting example upon induction of regeneration, tobacco multicellular tissues may provide for a higher number of de novo formed shoots per multicellular tissue as compared to the same number of cucumber multicellular tissues. A preferred multicellular tissue is a callus or explant.

In addition or alternatively, the maximum potential of a plant cell to regenerate can for example be measured by comparing the amount of starting material with the amount of material that is regenerated after exposure to cytokinin. As a non-limiting example, the number of multicellular tissues that form the starting material can be determined. Subsequently after exposure to at least a cytokinin under conditions, preferably optimal conditions that allow for regeneration, the number of multicellular tissues that are regenerated can be determined. The percentage of regenerated multicellular tissues is herein understood to be the cytokinin-induced regeneration capacity of the plant cell. As non-limiting example, the starting material can be a hypocotyl explant, such as an elongated hypocotyl explant, and/or the regenerated tissue can be a shoot, such as an inflorescence shoot.

The cytokinin-induced regeneration may be at least one of meristem formation, adventitious shoot formation, inflorescence formation, somatic embryo formation, root formation, elongation of adventitious shoots and regeneration of a complete plant. As a non-limiting example, the number of de novo formed shoots per multicellular tissue may be determined.

The skilled person understands that there are other similar approaches known in the art to determine the cytokinin-induced regeneration capacity.

Preferably, the cytokinin-induced regeneration capacity of the plant cell is improved as compared to a control preferably as tested under the same, or substantially the same conditions, or optimal conditions. Preferably, said control is an identical plant cell or substantial identical plant cell that has the same genetic background as compared to the plant cell obtained or obtainable by the method of the invention, with the exception of the modified or newly introduced histidine kinase. In other words, preferably, the control is a plant cell that is genetically identical to the plant cell obtained by the method of the invention before the step of increasing or introducing the expression of a histidine kinase of the method of the invention. Thus, preferably the identical plant cell or substantially identical plant cell has the same genetic background as the plant cell having an improved regeneration capacity, but does not have an introduced or increased expression of the histidine kinase as defined herein.

The cytokinin-induced regeneration capacity of a plant cell is the maximum potential of the plant cell to regenerate under conditions, preferably optimal conditions, that allow for regeneration. The optimal conditions preferably includes at least an optimal concentration of a cytokinin.

The regeneration capacity can be expressed as the percentage of the starting material that regenerates. As a non-limiting example, if 7 of the 360 explants regenerate under conditions that allow for regeneration, the regeneration capacity is (7/360*100%) 1.9%. Expression of a histidine kinase as defined herein allows for an improved regeneration capacity. As a non-limiting example, introduced or increased expression of a histidine kinase can increase the number of regenerated explants to e.g. 160 when grown under similar or substantially the same regeneration conditions. The regeneration capacity has increased to (160/360*100%) to 44.4%. Hence, the regeneration capacity has improved (44.4–1.9) 42.5% (see e.g. Table 2). As a further non-limiting example, the regeneration capacity of a plant cell can be expressed as the number of shoots formed per explant at a certain time point. For example 183 days after induced regeneration, 93 shoots can be harvested from 200 explants that have an introduced or increased expression of a histidine kinase (see also table 4), e.g. the regeneration capacity at day 183 is (93/200*100%) 46.5%. At the same time point 64 shoots can be harvested from 200 control explants, e.g. the regeneration capacity at day 183 is (64/200*100%) 32%. The regeneration capacity thus has improved ((46.5–32)/32*100%) 45% (see e.g. Table 4).

As a non-limiting example, the improvement in cytokinin-induced regeneration capacity can be expressed as the difference in regeneration capacity between a plant cell having an increased or introduced expression of the histidine kinase as defined herein and an identical cell not having said increased or introduced expression. Preferably, the regeneration capacity of the plant cell is improved at least about 1%, 2%, 5%, 10%, 15%, 20%, 25%, 30%, 35%, 40%, 45%, 50%, 55%, 60%, 65%, 70%, 75%, 80%, 85%, 90%, 95%, or about 100% as compared to an identical plant cell not having an increased or introduced expression of the histidine kinase.

The skilled person understands that there are other suitable approaches in the art to determine an improvement in cytokinin-induced regeneration capacity, which can be equally used in the method of the invention.

A regenerated plant cell has preferably at least one of meristem formation or de novo meristem formation, shoot formation or adventitious shoot formation, inflorescence formation, somatic embryo formation, root formation, elongation of adventitious shoots and the regeneration of a complete plant.

The method can further comprise, for example, testing the plant cell for an improved regeneration capacity. The improved regeneration capacity is preferably improved compared to a control, wherein the control is preferably an identical plant cell not having an increased or introduced expression of a histidine kinase as defined herein.

As a non-limiting example, the testing step may be performed by determining the number of de novo formed shoots. Hence, the method of the invention may further comprise a step of determining, e.g. counting, the number of de novo formed shoots. The number of de novo formed shoots can be determined in relation to the number of multicellular tissues, preferably the number of explants, prior to shoot formation. Alternatively or in addition, the number of meristems may be determined or any tissues derived therefrom. It is however understood herein that the formation of callus or "green callus" is not indicative of the number of shoots that can be formed. The formation of callus can be an indicator of proliferation, but not an indicator of organisation/differentiation.

As a further non-limiting example, the testing step may be performed by determining the number of explants that regenerate. Hence, the method of the invention may further comprise a step of determining, e.g. counting, the number of explants that have regenerated. The number of regenerated explants can be determined in relation to the number of explants that formed the starting material.

A histidine kinase for use in the invention is a protein that is capable of transferring a phosphate group to a histidine residue on a specific substrate. Preferably, the histidine kinase for use in the invention is a transmembrane protein and can act as a cellular receptor for cytokinin. Upon binding the cytokinin, the histidine kinase can initiate a signal transduction resulting in the activation of Type B ARRs (*Arabidopsis* response regulators) and subsequent cytokinin-regulated transcription.

The histidine kinase may be a CHASE-domain containing histidine kinase (CHK). These receptors preferably display a complex multidomain structure with a N-terminal part including preferably at least two hydrophobic membrane-spanning domains (TM) that border an extracytosolic sensing domain referred to as CHASE (Cyclase/Histidine kinase Associated Sensory Extracellular) as well as a cytoplasmic C-terminal part containing a catalytic histidine kinase (HK) domain and both receiver and pseudo-receiver domains (REC and REC-like, respectively). The HK domain is preferably composed of an HK dimerization and phosphoacceptor domain (HisKA) and an HK catalytic domain called the HK-like ATPase domain (HATPase) (Daudu et al, "*CHASE-Containing Histidine Kinase Receptors in Apple Tree: From a Common Receptor Structure to Divergent Cytokinin Binding Properties and Specific Functions*", Front Plant Sci. (2017); 8: 1614).

The histidine kinase for use in the invention can be a protein that is native to the plant cell, e.g. an endogenous histidine kinase protein that is expressed, or overexpressed, in the cell. Hence, the endogenous protein can be a protein that is encoded in the genome of a wild-type plant cell and its expression is introduced or enhanced. In addition or alternatively, additional copies of the endogenously encoded protein can be introduced into the plant cell.

In an embodiment, the histidine kinase for use in the invention is not native, i.e. is foreign, to the plant cell. Such exogenous protein may be a homologous protein. The protein can be derived from the same subgenus, genus, tribe, subfamily, family, order and/or clade. Alternatively, the protein can be derived from a different subgenus, genus, tribe, subfamily, family, order and/or clade. The histidine kinase protein can be an artificial protein, e.g. a protein that does not occur in nature but fulfils the same or similar function as a naturally-occurring histidine kinase.

In a preferred embodiment, the histidine kinase is at least one of CHK2, CHK3 and CHK4. Preferably the histidine kinase is at least one of CHK2 and CHK4. In an embodiment, the histidine kinase is CHK2. In another embodiment, the histidine kinase is CHK4. It is envisioned herein that the expression of a combination of histidine kinases is introduced or increased in the plant cell. For example, the expression of at least two different CHK2 proteins, at least two different CHK3 and/or at least two different CHK4 proteins is increased or introduced in the plant cell. Alternatively or in addition, the plant cell may have an increased or introduced expression of at least a CHK2 and CHK4 protein, at least a CHK2 and CHK3 protein, or at least a CHK3 and CHK4 protein. The plant cell can have an increased or introduced expression of at least a CHK2, CHK3 and a CHK4 protein as defined herein.

The histidine kinase of the invention may be encoded by a nucleotide sequence having at least 50% sequence identity with at least one of SEQ ID NO: 1, SEQ ID NO:2 and SEQ ID NO: 3. Preferably, the nucleotide sequence encoding the CHK2 can have at least about 50%, 55%, 60%, 65%, 70%, 75%, 80%, 85%, 90%, 95%, 98%, 99% or 100% sequence identity with SEQ ID NO: 1. SEQ ID NO: 1 is the *Arabidopsis* CHK2 coding sequence, also annotated as AHK2.

Preferably, the nucleotide sequence encoding the CHK3 can have at least about 50%, 55%, 60%, 65%, 70%, 75%, 80%, 85%, 90%, 95%, 98%, 99% or 100% sequence identity with SEQ ID NO: 2. SEQ ID NO: 2 is the *Arabidopsis* CHK3 coding sequence, also annotated as AHK3.

Preferably, the nucleotide sequence encoding the CHK4 preferably has at least about 50%, 55%, 60%, 65%, 70%, 75%, 80%, 85%, 90%, 95%, 98%, 99% or 100% sequence identity with SEQ ID NO: 3. SEQ ID NO: 3 is the *Arabidopsis* CHK4 coding sequence, also annotated as AHK4, CRE1, WOL1, WOODEN LEG 1.

In one embodiment, the nucleotide sequence encoding the CHK2 protein is, or is derived from the gene At5g35750 (SEQ ID NO: 7), a homolog thereof or a sequence having at least about 50%, 55%, 60%, 65%, 70%, 75%, 80%, 85%, 90%, 95%, 98%, 99% or 100% sequence identity with At5g35750 or its homolog. The percentage identity can be determined over the full length of the genomic sequence. Alternatively the percentage identity can be determined over the full length of the coding sequence of the gene.

Examples of homologs include *Glycine max* (Soybean) (GLYMA02G47611 or GLYMA14G01040), *Oryza sativa* (Rice) (0510G0362300, OSJNBA0058E19.1 or OSJNBA0073L01.1), *Populus trichocarpa* (Black Cottonwood) (POPTR_0014516260 G), *Solanum lycopersicum* (Tomato) (SOLYC07G047770.2) and *Vitis vinifera* (Grape) (VIT_1250057 G00690). A preferred homolog is *Solanum lycopersicum* SOLYC07G047770.2.

Preferably, the nucleotide sequence encoding the CHK2 protein is, or is derived from the gene SOLYC07G047770.2 (SEQ ID NO: 30), a homolog thereof and/or a sequence having at least about 50%, 55%, 60%, 65%, 70%, 75%, 80%, 85%, 90%, 95%, 98%, 99% or 100% sequence identity with SOLYC07G047770.2. The percentage identity can be determined over the full length of the genomic sequence. Alternatively the percentage identity can be determined over the full length of the coding sequence of the gene.

In one embodiment, the sequence encoding the CHK3 protein is, or is derived from the gene At1g27320 (SEQ ID NO: 8), a homolog thereof or a sequence having at least about 50%, 55%, 60%, 65%, 70%, 75%, 80%, 85%, 90%, 95%, 98%, 99% or 100% sequence identity with At1g27320 or its homolog. The percentage identity can be determined over the full length of the genomic sequence. Alternatively the percentage identity can be determined over the full length of the coding sequence of the gene.

Examples of homologs include *Brachypodium distachyon* (Purple false brome) (BRAD12G59127), *Glycine max* (Soybean) (GLYMA05G28070 or GLYMA08G11060), *Oryza sativa* (Rice) (B1455F06.33), *Populus trichocarpa* (Black Cottonwood) (HK3A or POPTR_0003516950 G), *Solanum lycopersicum* (Tomato) (SOLYC05G015610.2) and *Vitis vinifera* (Grape) (VIT_0150010 G03780).

In one embodiment, the sequence encoding the CHK4 protein is, or is derived from, the gene At2g01830 (SEQ ID NO: 9), a homolog thereof, or a sequence having at least about 50%, 55%, 60%, 65%, 70%, 75%, 80%, 85%, 90%, 95%, 98%, 99% or 100% sequence identity with At2g01830 or its homolog. The percentage identity can be determined over the full length of the genomic sequence. Alternatively the percentage identity can be determined over the full length of the coding sequence of the gene.

Examples of homologs include *Brachypodium distachyon* (Purple false brome) (BRADI1G10660), *Glycine max* (Soybean) (GLYMA02G09550, GLYMA05G34310, GLYMA07G19620, GLYMA07G27540 or GLYMA08G05370), *Physcomitrella patens* (Moss) (CKI3A, CKI3B, CKI3C, CRE1, CRE2, CRE3, PHYPADRAFT_162473, PHYPADRAFT_169293, PHYPADRAFT_172225, PHYPADRAFT_229095 or PHY- PADRAFT_68053), *Populus trichocarpa* (Black Cottonwood) (CRE1B, POPTR_0008513720 G), *Solanum lycopersicum* (Tomato) (SOLYC04G008110.2), *Sorghum bicolor* (Sorghum) (SB01G010070) and *Vitis vinifera* (Grape) (VIT_01S0011G06190)

The sequence encoding the histidine kinase may be codon-optimized for expression in plant cells, preferably codon-optimized for expression in the plant cell of the method of the invention. As a non-limiting example, the expressed or de novo expressed histidine kinase can be an endogenous protein while the sequence encoding this endogenous protein is an exogenous, codon-optimized, sequence. Alternatively, the codon-optimized sequence can encode a histidine kinase that is exogenous for the plant cell.

In one embodiment, the amino acid sequence of the histidine kinase has at least 50% sequence identity with at least one of SEQ ID NO: 4, SEQ ID NO: 5 and SEQ ID NO: 6.

The amino acid sequence encoding the CHK2 can have at least about 50%, 55%, 60%, 65%, 70%, 75%, 80%, 85%, 90%, 95%, 98%, 99% or 100% sequence identity with SEQ ID NO: 4. SEQ ID NO: 4 is the *Arabidopsis* CHK2 protein.

Alternatively, the nucleotide sequence encoding the CHK3 can have at least about 50%, 55%, 60%, 65%, 70%, 75%, 80%, 85%, 90%, 95%, 98%, 99% or 100% sequence identity with SEQ ID NO: 5. SEQ ID NO: 5 is the *Arabidopsis* CHK3 protein.

Preferably, the nucleotide sequence encoding the CHK4 preferably has at least about 50%, 55%, 60%, 65%, 70%, 75%, 80%, 85%, 90%, 95%, 98%, 99% or 100% sequence identity with SEQ ID NO: 6. SEQ ID NO: 6 is the *Arabidopsis* CHK4 protein.

In one embodiment, the CHK2 amino acid sequence is or is derived from AT5G35750.1 (AHK2), a homolog thereof, or a sequence having at least about 50%, 55%, 60%, 65%, 70%, 75%, 80%, 85%, 90%, 95%, 98%, 99% or 100% sequence identity with AHK2 or its homolog. A preferred homolog is *Solanum lycopersicum* CHK2 (SlyCHK2) having a sequence of SEQ ID NO: 31, and/or a sequence having at least about 50%, 55%, 60%, 65%, 70%, 75%, 80%, 85%, 90%, 95%, 98%, 99% or 100% sequence identity with SlyCHK2.

Examples of homologs include *Glycine max* (Soybean) (K7KBR1 or K7M476), *Oryza sativa* (Rice) (Q0IY65, Q9AUQ0 or Q8S6P5), *Populus trichocarpa* (Black Cottonwood) (B9IAR0), *Solanum lycopersicum* (Tomato) (K4CEY3) and *Vitis vinifera* (Grape) (F6HHM7).

In one embodiment, the CHK3 amino acid sequence is or is derived from AT1G27320 (AHK3), a homolog thereof, or a sequence having at least about 50%, 55%, 60%, 65%, 70%, 75%, 80%, 85%, 90%, 95%, 98%, 99% or 100% sequence identity with AHK3 or its homolog.

Examples of homologs include *Brachypodium distachyon* (Purple false brome) (I1HUP8), *Glycine max* (Soybean) (I1K3M7 or I1KS30), *Oryza sativa* (Rice) (Q5JJP1), *Populus trichocarpa* (Black Cottonwood) (B9GML7 or B9GZP2), *Solanum lycopersicum* (Tomato) (K4BYS7) and *Vitis vinifera* (Grape) (D7TAZ7).

In one embodiment, the CHK4 amino acid sequence is or is derived from AT2G01830 (AHK4), a homolog thereof, or a sequence having at least about 50%, 55%, 60%, 65%, 70%, 75%, 80%, 85%, 90%, 95%, 98%, 99% or 100% sequence identity with AHK4 or its homolog.

Examples of homologs include *Brachypodium distachyon* (Purple false brome) (I1GNZ3), *Glycine max* (Soybean) (K7K767, K7KRH0, K7L210, K7L2C5 or I1KQE9), *Physcomitrella patens* (Moss) (A9RME1, A9SJM1, A9T3T9, A9S5U9, A9TAF3, A9TKN3, A9S2L4, A9TCH3, A9TVM0, A9SEU1 or A9RME0), *Populus trichocarpa* (Black Cottonwood) (B9HVS3 or B9HJJ3), *Solanum lycopersicum* (Tomato) (K4BNW7), *Sorghum bicolor* (Sorghum) (C5WN04) and *Vitis vinifera* (Grape) (F6HFB2)

In an embodiment of the invention, the histidine kinase having increased or introduced expression is a functional histidine kinase. A functional histidine kinase is preferably fulfilling the same or similar function in a plant cell as the function of a histidine kinase having amino acid sequence SEQ ID NO: 4, SEQ ID NO: 5 or SEQ ID NO: 6 in *Arabidopsis thaliana*. A CHK2 as defined herein is preferably fulfilling the same or similar function in a plant cell as the function of a protein having amino acid sequence of SEQ ID NO: 4 in *Arabidopsis thaliana*. A CHK3 as defined herein is preferably fulfilling the same or similar function in a plant cell as the function of a protein having amino acid sequence of SEQ ID NO: 5 in *Arabidopsis thaliana*. A CHK4 as defined herein is preferably fulfilling the same or similar function in a plant cell as the function of a protein having amino acid sequence of SEQ ID NO: 6 in *Arabidopsis thaliana*. In context of the invention, a functional histidine kinase, or CHASE-domain containing histidine kinase, is preferably capable of binding cytokinin and initiates a signal transduction that results in cytokinin-regulated transcription. Alternatively or in addition, the functional histidine kinase can also be defined as a histidine kinase that is capable of improving the cytokinin-induced regeneration capacity of a plant cell upon increased or introduced expression.

The method can comprise, for example, a step of genetically engineering the plant, plant protoplast or plant cell to overexpress or express de novo a histidine kinase protein. In one embodiment, the expression of the histidine kinase is transiently increased or introduced into the plant cell. It is well-known in the art how to transiently increase or introduce the expression of a protein and the invention is not limited to any specific method.

As a non-limiting example, the method can comprise transforming a plant cell with a vector or expression construct comprising a recombinant nucleic acid encoding the histidine kinase as described herein, preferably as an expression construct of the ninth aspect as defined herein. Such vector or expression construct preferably does not integrate into the plant genome. As a result, the histidine kinase protein transcribed from the expression construct will be temporarily expressed. Introduction of a nucleic acid encoding the histidine kinase can be performed using any suitable means known in the art, for example such as described in WO2009/082190. In some embodiments, the method comprises contacting the plant protoplast or plant cell with an *Agrobacterium* strain comprising the vector to introduce the recombinant nucleic acid into the plant protoplast or plant cell.

Alternatively or in addition, the plant cells can be transformed with a histidine kinase protein as defined herein. The introduction of the histidine kinase protein can be performed by any suitable means known to the skilled person.

In one embodiment, the genome of the plant cell can be modified to transiently express or overexpress the histidine kinase protein as defined herein. As a non-limiting example, an expression cassette can be introduced into the genome of a plant cell, wherein the expression cassette at least comprises an inducible promoter and a sequence encoding the histidine kinase. The histidine kinase can for example be expressed upon the presence of an inducer. The inducer can bind to a transactivator, e.g. an introduced transactivator, which transactivator initiates or augments the expression of the histidine kinase, for example by binding to the inducible promoter that is operably linked to the sequence encoding the histidine kinase.

In an embodiment, the expression of the histidine kinase is continuously increased or introduced in the plant cell.

Continuous overexpression or continuous de novo expression of the histidine kinase protein can be achieved by, for example, inserting at least one additional copy of an endogenous gene encoding the histidine kinase protein into the genome of a plant, plant protoplast or plant cell. Further ways are modulating promoter and/or further regulating sequences that are operably linked to an endogenous histidine kinase-encoding sequence, resulting in enhanced or introduced expression. These regulating sequences can include genomic as well as epigenomic regulators.

In an embodiment, the genome of the plant is modified to overexpress or de novo express a histidine kinase as defined herein by modifying a genomic promoter fragment having at least about 50%, 55%, 60%, 65%, 70%, 75%, 80%, 85%, 90%, 95%, 98% or 100% sequence identity with at least one of SEQ ID NO: 10, SEQ ID NO: 11 and SEQ ID NO: 12.

In one embodiment, the genome of the plant cell is modified to overexpress or de novo express a histidine kinase as defined herein. As a non-limiting example, regulatory sequences surrounding a gene encoding an endogenous histidine kinase as defined herein can be modified to increase or induce the expression of the histidine kinase. These regulatory sequences can be located less than about 10 kb, 8 kb, 5 kb, 3 kb, 2 kb, 1 kb, 800 bp, 600 bp, 400 bp, 200 bp, 100 bp or less than about 50 bp upstream from the start codon encoding the histidine kinase. Alternatively, these regulatory sequences can be located less than about 10 kb, 8 kb, 5 kb, 3 kb, 2 kb, 1 kb, 800 bp, 600 bp, 400 bp, 200 bp, 100 bp or less than about 50 bp downstream from the start codon encoding the histidine kinase.

In an embodiment, the regulatory sequences modified to increase or induce the expression of an endogenous histidine kinase as defined herein can be located less than about 10 kb, 8 kb, 5 kb, 3 kb, 2 kb, 1 kb, 800 bp, 600 bp, 400 bp, 200 bp, 100 bp or less than about 50 bp upstream of a sequence having at least about 50%, 60%, 70%, 80%, 90%, 95%, 98% or 100% sequence identity with SEQ ID NO: 7.

In an embodiment, the regulatory sequences modified to increase or induce the expression of an endogenous histidine kinase as defined herein can be located less than about 10 kb, 8 kb, 5 kb, 3 kb, 2 kb, 1 kb, 800 bp, 600 bp, 400 bp, 200 bp, 100 bp or less than about 50 bp upstream of a sequence having a sequence with at least about 50%, 60%, 70%, 80%, 90%, 95%, 98% or 100% sequence identity with SEQ ID NO: 8.

In an embodiment, the regulatory sequences modified to increase or induce the expression of an endogenous histidine kinase as defined herein can be located less than about 10 kb, 8 kb, 5 kb, 3 kb, 2 kb, 1 kb, 800 bp, 600 bp, 400 bp, 200 bp, 100 bp or less than about 50 bp upstream of a sequence having a sequence with at least about 50%, 60%, 70%, 80%, 90%, 95%, 98% or 100% sequence identity with SEQ ID NO: 9.

In an embodiment, the plant genome can be modified at specific position using for example KeyBase®, targeted nucleotide exchange (TNE), oligo-directed mutagenesis (ODM) or Oligonucleotide Directed Targeted Mutagenesis (OD™) to increase or introduce the expression of a histidine kinase as defined herein.

In some embodiment, methods for editing the genome of the plant cell to introduce or increase the expression of an endogenous histidine kinase as defined herein includes, but is not limited to, the use of specific nucleases such as the CRISPR system, ZFNs or TALENs. Non-limiting examples of specific nucleases of the CRISPR system include Cas9, Cpf1 and CasX.

Instead or in addition to introducing or increasing the expression of an endogenous histidine kinase, an exogenous histidine kinase protein can be stably expressed in a plant cell. For example, a nucleic acid encoding a histidine kinase, e.g. an exogenous histidine kinase, can be stably inserted into the genome of a plant cell. The expression of such histidine kinase can be regulated by sequences operably linked to the introduced sequence. These regulating sequences can be endogenous to the cell, or may be introduced e.g. together with the introduction of the nucleic acid encoding the histidine kinase. These regulating sequences can include genomic as well as epigenomic regulators.

The method of the invention may further comprise a step of testing overexpression or de novo expression of the histidine kinase of the method of the invention. In other words, the invention also provides for a method for improving a cytokinin-induced regeneration capacity of a plant cell comprising the steps of:

a) increasing or introducing the expression of a histidine kinase as defined herein in the plant cell; and, b) detecting the expression level of said histidine kinase in the plant cell.

Methods for testing overexpression or de novo expression of the histidine kinase protein include, but are not limited to, PCR analysis, sequencing of genomic DNA, sequencing of mRNA transcript, analyzing mRNA transcript levels (Northern-blot analysis), analyzing copy number (Southern blot analysis), etc. Preferably, the method of the invention results in at least 2%, 5%, 10%, 20%, 30%, 40%, 50%, 60%, 70%, 80%, 90%, or 100% increase of expression of the histidine kinase as compared to the control as defined herein.

In an embodiment, the plant cell is obtained or obtainable from a plant that is known to have an inefficient regeneration capacity. An insufficient regeneration capacity is herein understood as the regeneration capacity is less than about 25%, 20%, 15%, 10%, 8%, 5%, 4%, 3%, 2%, or 1%, preferably when the plant cell is kept under defined conditions, preferably optimal conditions, that allow for regeneration. Examples of plants having an inefficient regeneration capacity include, but are not limited to sweet pepper, cucumber and melon.

The plant cell for use in the invention may be obtained or obtainable from a plant that is incapable to regenerate under conditions that should allow for regeneration.

In one embodiment, the plant cell is obtained or obtainable from a plant selected from the group consisting of barley, cabbage, canola, cassava, cauliflower, chicory, cotton, cucumber, eggplant, grape, hot pepper, lettuce, maize, melon, oilseed rape, potato, pumpkin, rice, rye, *sorghum*, squash, sugar cane, sugar beet, sunflower, sweet pepper, tomato, water melon, wheat, zucchini, soybean, *chrysanthemum* and *Arabidopsis*.

In one embodiment, the plant cell is obtained or obtainable from a plant selected from the group consisting of sweet pepper, cucumber, melon, soybean, *chrysanthemum* and *Arabidopsis*.

In an embodiment, the plant cell is obtained or obtainable from a plant selected from the group consisting of sweet pepper, cucumber and melon.

In one embodiment, the plant cell is obtained or obtainable from tomato or pepper, preferably the plant cell is obtained or obtainable from *Solanum lycopersicum* or *Capsicum annuum*.

In a second aspect, the invention pertains to a method for regenerating a plant comprising the steps of i) incubating a plant cell obtained or obtainable by the method of the first aspect of the invention in a medium comprising a cytokinin as defined herein; and ii) allowing the plant cell to regenerate into a plant.

The invention therefore also pertains to a method for regenerating a plant comprising the steps of:
  a) increasing or introducing the expression of a histidine kinase as defined herein in the plant cell;
  b) optionally detecting the expression level of said histidine kinase in the plant cell and optionally selecting a plant cell having an increased or introduced expression of the histidine kinase;
  c) incubating the plant cell, optionally the plant cell selected in step b), in a medium comprising a cytokinin as defined herein; and
  d) allowing the plant cell to regenerate into a plant.

In one embodiment, the plant cell is a plant cell as specified in the first aspect of the invention. The plant cell can be obtained or obtainable from a plant selected from the group consisting of barley, cabbage, canola, cassava, cauliflower, chicory, cotton, cucumber, eggplant, grape, hot pepper, lettuce, maize, melon, oilseed rape, potato, pumpkin, rice, rye, sorghum, squash, sugar cane, sugar beet, sunflower, sweet pepper, tomato, water melon, wheat, zucchini, soybean, chrysanthemum and Arabidopsis.

The method of the invention relates to improving a cytokinin-induced regeneration capacity of a plant cell, wherein the method comprises a step of increasing or introducing the expression of a histidine kinase protein. Cytokinins (CK) are a class of plant growth substances (phytohormones) that promote cell division, or cytokinesis, in plant roots and shoots. Cytokinins can travel up the xylem and promote lateral growth. They are involved primarily in cell growth and differentiation, but can also affect apical dominance, axillary bud growth, and leaf senescence.

The cytokinin for use in the invention can be an adenine-type cytokinin or a phenylurea-type cytokinin. Similarly, the cytokinin can be a naturally produced phytohormone or can be a synthesized compound. The adenine-type cytokinin can be a phytohormone that is synthesized in at least one of roots, seeds and fruits. In addition, cambium and other actively dividing tissues can also synthesize cytokinins A non-limiting example of a naturally occurring adenine-type cytokinin is Zeatin as well as its metabolic precursor 2iP. Non-limiting examples of synthetic adenine-type cytokinins are kinetin and 6-benzylaminopurine (BAP). Substituted urea compounds, such as thidiazuron and CPPU do not occur in plants but can act as cytokinins in tissue culture.

The adenine-type cytokinin can be selected from the group consisting of kinetin, zeatin, trans-zeatin, cis-zeatin, dihydrozeatin, 6-benzylaminopurine and 2iP, and combinations thereof. The phenylurea-type cytokinin can be diphenylurea or thidiazuron.

In one embodiment, the plant cell as defined herein is incubated in a medium comprising a cytokinin as defined herein under conditions that allow for the regeneration of the plant cell. The plant cell can be incubated in the medium comprising a cytokinin for at least about 1, 2, 3, 4, 5, 6, 7, 8, 9 or about 10 days, under conditions that allow for regeneration. The plant cell can be incubated in the medium comprising a cytokinin for at least about 1, 2, 3, 4, 5, 6, 7, 8, 9, 10, 11 or about 12 weeks, under conditions that allow for regeneration.

In one embodiment, the plant cell as defined herein is incubated in a medium comprising a cytokinin for at least 5, 6, 7, 8, 9 weeks.

In one embodiment, the regenerated plant cell can be further developed into a cotyledonary embryo. The terms "cotyledonary embryo" and "cotyledonary stage embryo" can be used interchangeably herein. The cotyledonary embryo is preferably a cotyledonary stage somatic embryo. In an embodiment, all cells of the cotyledonary embryo express or overexpress the histidine kinase as defined herein. The mutagenized cotyledonary embryo produced by the method of the invention can be further developed into a plantlet. The plantlet can further be developed into a plant.

In an embodiment of the invention, the method therefore comprises a further step of regenerating a plantlet and/or a plant from the plant cell.

In one embodiment, the plant cell as defined herein is incubated in a medium comprising a cytokinin. The cytokinin in the medium can be only one type of cytokinin. Alternatively, the plant cell can also be incubated in a mixture of cytokinins. For example, the plant cell can be incubated in a medium comprising at least 1, 2, 3, 4 or 5 different types of cytokinins.

A mixture of at least two cytokinins is for example selected from the group consisting of kinetin and zeatin, kinetin and trans-zeatin, kinetin and cis-zeatin, kinetin and dihydrozeatin, kinetin and 6-benzylaminopurine, kinetin and 2iP, zeatin and trans-zeatin, zeatin and cis-zeatin, zeatin and dihydrozeatin, zeatin and 6-benzylaminopurine, zeatin and 2iP, trans-zeatin, and cis-zeatin, trans-zeatin and dihydrozeatin, trans-zeatin and 6-benzylaminopurine, trans-zeatin and 2iP, cis-zeatin and dihydrozeatin, cis-zeatin and 6-benzylaminopurine, cis-zeatin and 2iP, dihydrozeatin and 6-benzylaminopurine, dihydrozeatin and 2iP, and 6-benzylaminopurine and 2iP. The skilled person understands that (an) additional type(s) of cytokinin(s) can be added to the mixture of the at least two cytokinins. It is known in the art that the type of added cytokinin is dependent on the type of plant cell and the skilled person can straightforwardly select the suitable cytokinin(s).

In one embodiment, the medium can contain additional compounds that promote the regeneration of the plant cell. Such additional compounds can for example be one or more growth regulators, e.g. one or more plant hormones. Plant hormones (also known as phytohormones or 'plant growth substances') are chemicals that can regulate plant growth. A plant hormone can affect at least one of plant shape, seed growth, flowering time, the sex of flowers, senescence of leaves, and senescence of fruits. Alternatively or in addition, plant hormone can affect at least one of upward growth of tissues, downward growth of tissues, leaf formation, stem growth, fruit development, fruit ripening, plant longevity, and plant death.

The further plant hormone for use in the method of the invention can be at least one of an auxin, abscisic acid, ethylene and a gibberellin. Alternatively or in addition, the further plant hormone can be at least one of a brassinosteroid, salicylic acid, a jasmonate, a plant peptide hormone, a polyamine, nitric oxide, a strigolactones, a Karrikin and triacontanol.

The at least one further plant hormone can be an auxin. Auxins are a class of plant hormones that can have morphogen-like characteristics. The auxin can be an endogenously synthesized auxin. The endogenously synthesized auxin can be selected from the group consisting of indole- 3-acetic acid (IAA), 4-chloroindole-3-acetic acid, phenylacetic acid, indole-3-butyric acid and indole-3-propionic acid.

The auxin can be a synthetic auxin, e.g. an auxin analog. The synthetic auxin can be at least one of 1-naphthaleneacetic acid, 2,4-dichlorophenoxyacetic acid (2,4-D), α-Naphthalene acetic acid (α-NAA), 2-Methoxy-3,6-dichlorobenzoic acid (dicamba), 4-Amino-3,5,6-trichloropicolinic acid (tordon or picloram), 1-naphthaleneacetic acid (NAA), indole-3-butyric acid (IBA) and 2,4,5-trichlorophenoxyacetic acid (2,4,5-T). The auxin can be 1-naphthaleneacetic acid (NAA).

In addition or alternatively, the further plant hormone can be at least a gibberellin. The gibberellin can be a 19-carbon gibberellin or a 20-carbon gibberellin. The gibberellin can be a dihydroxylated gibberellin. The gibberellin can be at least one of GA1, GA3, GA4 and GA7.

The concentration of the at least one further plant hormone (e.g. auxin) in the medium can be the same or similar to the concentration cytokinin (e.g. a ratio of about 1:1). Alternatively, the concentration of the at least one further plant hormone can be lower than the concentration cytokinin in the medium. The ratio of the at least one further plant hormone to cytokinin can be about 0.9:1.0; 0.8:1.0; 0.7:1.0; 0.6:1.0; 0.5:1.0; 0.4:1.0; 0.3:1.0; 0.2:1.0; 0.1:1.0; 0.01:1.0 or even about 0.001:1.0.

Alternatively, the concentration of the at least one further plant hormone can be higher than the concentration cytokinin in the medium. The ratio of the at least one further plant hormone to cytokinin can be about 1:0.9; 1:0.8; 1:0.7; 1:0.6; 1:0.5; 1:0.4; 1:0.3; 1:0.2; 1:0.1; 1:0.01 or even about 1:0.001.

The concentration cytokinin in the medium can be at least about 50 ng/ml, 75 ng/ml, 100 ng/ml, 125 ng/ml, 150 ng/ml, 175 ng/ml, 200 ng/ml, 225 ng/ml, 250 ng/ml, 275 ng/ml, 300 ng/ml, 325 ng/ml ng/ml, 350 ng/ml, 375 ng/ml, 400 ng/ml, 425 ng/ml, 450 ng/ml, 475 ng/ml, 500 ng/ml, 525 ng/ml, 550 ng/ml, 575 ng/ml, 600 ng/ml, 625 ng/ml, 650 ng/ml, 675 ng/ml, 700 ng/ml, 750 ng/ml, 800 ng/ml, 850 ng/ml, 900 ng/ml, 950 ng/ml, 1000 ng/ml, 1100 ng/ml, 1200 ng/ml, 1300 ng/ml, 1400 ng/ml, 1500 ng/ml, 1750 ng/ml, 2000 ng/ml, 2225 ng/ml, 2500 ng/ml, 2750 ng/ml, 3000 ng/ml, 3250 ng/ml, 3500 ng/ml, 3750 ng/ml, 4000 ng/ml, 4250 ng/ml, 4500 ng/ml, 4750 ng/ml or at least about 5000 ng/ml.

Alternatively or in addition, the concentration cytokinin in the medium can at most about 50 ng/ml, 75 ng/ml, 100 ng/ml, 125 ng/ml, 150 ng/ml, 175 ng/ml, 200 ng/ml, 225 ng/ml, 250 ng/ml, 275 ng/ml, 300 ng/ml, 325 ng/ml ng/ml, 350 ng/ml, 375 ng/ml, 400 ng/ml, 425 ng/ml, 450 ng/ml, 475 ng/ml, 500 ng/ml, 525 ng/ml, 550 ng/ml, 575 ng/ml, 600 ng/ml, 625 ng/ml, 650 ng/ml, 675 ng/ml, 700 ng/ml, 750 ng/ml, 800 ng/ml, 850 ng/ml, 900 ng/ml, 950 ng/ml, 1000 ng/ml, 1100 ng/ml, 1200 ng/ml, 1300 ng/ml, 1400 ng/ml, 1500 ng/ml, 1750 ng/ml, 2000 ng/ml, 2225 ng/ml, 2500 ng/ml, 2750 ng/ml, 3000 ng/ml, 3250 ng/ml, 3500 ng/ml, 3750 ng/ml, 4000 ng/ml, 4250 ng/ml, 4500 ng/ml, 4750 ng/ml or about 5000 ng/ml.

In an embodiment, the concentration cytokinin in the medium is in the range of about 50-5000 ng/ml, 75-4000 ng/ml, 100-3000 ng/ml, 125-2000 ng/ml, 130-1500 ng/ml, 140-1250 ng/ml, 150-1000 ng/ml, 175-800 ng/ml, 200-600 ng/ml or about 250-500 ng/ml.

The concentration cytokinin in the medium is preferably a concentration that is optimal to allow regeneration of a plant cell. The skilled person knows how to establish such optimal concentrations, e.g. through routine experimentation or these concentrations have been described previously in the art. A preferred optimal concentration is about 1000 ng/ml.

The medium for incubating the plant cell as defined herein can be a liquid medium or a solid medium. The medium is preferably sterile.

In the method and use of the invention as defined herein in the different aspects, the plant cell can be part of a multicellular tissue. A plant multicellular tissue can comprise differentiated cells. Alternatively or in addition, a multicellular tissue can comprise undifferentiated cells. In an embodiment, all cells of the multicellular tissue have an increased or introduced expression of a histidine kinase as defined herein. Alternatively, about 5%, 10%, 15%, 20%, 25%, 30%, 35%, 40%, 45%, 50%, 55%, 60%, 65%, 70%, 75%, 80%, 85%, 90%, 95%, 97%, 98% or about 99% of the cells of the multicellular tissue have an increased or de novo expression of a histidine kinase as defined herein.

The multicellular tissue can be a callus tissue, a plant organ or an explant.

The plant cell having induced or introduced expression of a histidine kinase as defined herein can be part of a callus. A callus is a group of undifferentiated cells, preferably derived from adult cells. Callus cells can be capable of undergoing embryogenesis and formation of an entirely new plant. A plant callus is considered a growing mass of unorganized plant parenchyma cells. Callus can be produced from a single differentiated cell, and callus cells can be totipotent, being able to regenerate the whole plant body. The plant callus can be derived from a somatic tissue or tissues, e.g. a tissue that is available for explant culture. The cells that give rise to callus and somatic embryos preferably undergo rapid division and/or are partially undifferentiated such as meristematic tissue. The callus cell used in the method of the invention can be friable or compact. In addition or alternatively the callus cell can be rooty, shooty, or embryogenic callus (Ikeuchi M, Plant Cell. 2013 September; 25(9): 3159-3173).

In an embodiment, the plant cell having an increased or introduced expression of a histidine kinase as defined herein can be part of a plant organ. The plant organ can be a vegetative organ or a reproductive organ. A vegetative organ can be derived from the shoot system or root system. The organ can be at least one of roots, stems and leaves. A reproductive plant organ can be selected from the group consisting of flower, seed, fruit, cone, sori, strobili and gametophores.

In an embodiment, the plant cell having an increased or introduced expression of a histidine kinase as defined herein can be part of an explant. An explant can be defined herein as a sample obtained from a part of a plant. The plant sample can be placed on a solid culture medium or liquid medium. Explants can be taken from many different parts of a plant, including portions of shoots, leaves, stems, flowers, roots, single undifferentiated cells and from mature cells. The cells preferably contain living cytoplasm and nuclei and are able to de-differentiate and resume cell division. An explant can be, or can be obtainable or obtained from, a meristematic end of a plant, such as e.g. the stem tip, axillary bud tip or root tip. In one embodiment, the explant is selected from the group consisting of a hypocotyl explant, a stem explant, a cotyledon explant, a root explant, a leaf explant, a flower explant and a meristematic tissue. In one embodiment, the explant is a hypocotyl explant.

The plant regenerated by the method of the invention may subsequently be crossed to remove the increased or introduced expression of a histidine kinase as defined herein.

Hence the method may comprise a step of crossing the regenerated plant to remove the previously increased or introduced expression of a histidine kinase. The plant may be crossed with a plant of a different species or of the same species and progeny that no longer has an increased or introduced expression of a histidine kinase may be selected.

In a third aspect, the invention pertains to a plant or plant part obtainable or obtained by the method of the invention as defined herein. The plant or plant part can be obtainable or obtained by the process of organogenesis or somatic embryogenesis. Plant cells obtained from the plant or plant part have an increased or introduced expression of a histidine kinase as defined herein. The plant obtainable or obtained by the method of the invention is preferably selected from the group consisting of barley, cabbage, canola, cassava, cauliflower, chicory, cotton, cucumber, eggplant, grape, hot pepper, lettuce, maize, melon, oilseed rape, potato, pumpkin, rice, rye, *sorghum*, squash, sugar cane, sugar beet, sunflower, sweet pepper, tomato, water melon, wheat, zucchini, soybean, *chrysanthemum* and *Arabidopsis*. The plant, plant part or plant cell can have an increased or induced expression of the histidine kinase as defined herein in all cells. Alternatively about 5%, 10%, 15%, 20%, 25%, 30%, 35%, 40%, 45%, 50%, 55%, 60%, 65%, 70%, 75%, 80%, 85%, 90%, 95%, 97%, 98% or about 99% of the plant cells have an increased or introduced expression of the histidine kinase as defined herein. In one embodiment, the plant part is a seed, a fruit or a non-propagating material.

In an embodiment, the plant or the plant cell of the invention comprises a genetic modification, wherein the modification results in an increased or introduced expression of a histidine kinase, as compared to a control plant. Preferred genetic modifications are indicated herein above. The plant or plant cell of the invention preferably comprises a nucleic acid of the eight aspect as defined herein and/or an expression construct of the ninth aspect as defined herein.

In a fourth aspect, the invention concerns a product derived from the plant or plant part obtainable or obtained by the method of the invention, e.g. fruits, leaves, plant organs, plant fats, plant oils, plant starch, and plant protein fractions, either crushed, milled or still intact, mixed with other materials, dried, frozen, and so on. These products may be non-propagating. Preferably, said plant product comprises a genetic modification, wherein the modification results in an increased or introduced expression of a histidine kinase, as compared to a control plant. Preferred genetic modifications are indicated herein above. Said plant product may comprise a nucleic acid of the eight aspect as defined herein and/or an expression construct of the ninth aspect as defined herein. Preferably, these products comprise at least fractions of said genetic modification, nucleic acid and/or construct, which allows to assess that the plant product is derived from a plant obtained by the method of the first and/or second aspect of the invention as defined herein.

In a fifth aspect, the invention concerns progeny of the plant cell, plantlet or plant obtainable or obtained by the method of the invention. Hence, the plant cells of the progeny have an increased or induced expression of a histidine kinase as defined herein and have an improved cytokinin-induced regeneration capacity. Said progeny may comprise the genetic modification, nucleic acid and/or an expression construct of the plant or plant part of the third aspect of the invention as defined herein.

In a sixth aspect, the invention pertains to the use of a CHK2, CHK3 and/or CHK4 histidine kinase, as defined herein for improving a cytokinin-induced regeneration capacity of a plant. In one embodiment, the invention concerns the use of a CHK2 and/or CHK4 histidine kinase as defined herein for improving a cytokinin-induced regeneration capacity of a plant. In a further embodiment, the invention concerns the use of at least a CHK4 histidine kinase as defined herein for improving a cytokinin-induced regeneration capacity of a plant. The plant is preferably a plant as defined herein above.

In a seventh aspect, the invention pertains to the use of a CHK2, CHK3 and/or CHK4 histidine kinase as defined herein above in a method for improving a cytokinin-induced regeneration capacity of a plant. Preferably, the CHK2, CHK3 and/or CHK4 histidine kinase is used in a method as defined in the first and/or second aspect of the invention, for improving a cytokinin-induced regeneration capacity of a plant.

In an eighth aspect, the invention concerns a nucleic acid encoding a histidine kinase as defined herein. In a preferred embodiment, the nucleic acid encodes for at least one of CHK2, CHK3 and CHK4 as defined herein. Preferably the nucleic acid encodes for least one of CHK2 and CHK4 as defined herein. Preferably, the nucleic acid encodes for CHK4 as defined herein.

In one embodiment, the sequence of the nucleic acid can have at least about 40%, 45%, 50%, 55%, 60%, 65%, 70%, 75%, 80%, 85%, 90%, 95%, 98% or about 100% sequence identity with at least one of SEQ ID NO: 1, SEQ ID NO: 2 and SEQ ID NO: 3.

Alternatively, the sequence of the nucleic acid can have at least about 40%, 45%, 50%, 55%, 60%, 65%, 70%, 75%, 80%, 85%, 90%, 95%, 98% or about 100% sequence identity with at least one of SEQ ID NO: 7, SEQ ID NO: 8 and SEQ ID NO: 9.

The nucleic acid can be isolated from its natural environment. In addition or alternatively, at least 1, 2, 3 or 4 nucleotides can flank the nucleic acid as defined herein, wherein said nucleotides do not flank the nucleic acid in a natural environment, i.e. resulting in a non-naturally occurring nucleic acid.

In a ninth aspect, the invention pertains to an expression construct for the expression of a histidine kinase as defined herein. In an embodiment, the expression construct comprises the sequence of a nucleic acid as defined herein above in the eighth aspect. The expression construct can comprise the sequence of at least 1, 2, 3, 4 or 5 nucleic acids as defined herein above in the eighth aspect.

The expression construct can comprise the sequence of at least two or more copies of the same nucleic acid and/or can comprise the sequence of at least two different nucleic acids as defined herein.

As a non-limiting example, the expression construct can comprise at least the sequence of a nucleic acid having at least about 40%, 45%, 50%, 55%, 60%, 65%, 70%, 75%, 80%, 85%, 90%, 95%, 98% or about 100% sequence identity with SEQ ID NO: 1 as well as the sequence of a nucleic acid having at least about 40%, 45%, 50%, 55%, 60%, 65%, 70%, 75%, 80%, 85%, 90%, 95%, 98% or about 100% sequence identity with SEQ ID NO: 3, As an another non-limiting example, the expression construct can comprise at least the sequence of a nucleic acid having at least about 40%, 45%, 50%, 55%, 60%, 65%, 70%, 75%, 80%, 85%, 90%, 95%, 98% or about 100% sequence identity with SEQ ID NO: 7 as well as the sequence of a nucleic acid having at least about 40%, 45%, 50%, 55%, 60%, 65%, 70%, 75%, 80%, 85%, 90%, 95%, 98% or about 100% sequence identity with SEQ ID NO: 9, The expression construct can further comprise one or more regulatory elements that are operably linked to the nucleic acid sequence or nucleic acid sequences as defined herein. A preferred regulatory element is a promoter. The promoter for expression in a plant cells is herein understood as a promoter that is active in plants or plant cells, i.e. the promoter has the general capability to drive transcription within a plant or plant cell.

The promoter can be a constitutive promoter, an inducible promoter or a tissue specific promoter. It is understood herein that a "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

The promoter can be a caulimovirus promoter, such as a cauliflower mosaic virus (CaMV) promoter, a nopaline synthase promoter or an octopine synthase promoter.

The promoter can have at least about 40%, 45%, 50%, 55%, 60%, 65%, 70%, 75%, 80%, 85%, 90%, 95%, 98% or about 100% sequence identity with at least one of SEQ ID NO: 10, SEQ ID NO: 11, SEQ ID NO: 12 and SEQ ID NO: 13. Preferably, the promoter can have at least about 40%, 45%, 50%, 55%, 60%, 65%, 70%, 75%, 80%, 85%, 90%, 95%, 98% or about 100% sequence identity with SEQ ID NO: 12.

The present invention has been described above with reference to a number of exemplary embodiments. Modifications and alternative implementations of some parts or elements are possible, and are included in the scope of protection as defined in the appended claims.

EXAMPLES

Example 1: Cloning of the *Arabidopsis* CHK2 Gene

The coding sequence of the *Arabidopsis* CHK2 gene (AT5G35750) was amplified by PCR using CHK2 specific forward primer 14_04109 and reverse primer 14_04110 from *Arabidopsis thaliana* Col-0 genomic DNA as template. A second PCR amplification was performed with primers 14_04116 (forward) and 14_04117 (reverse) to incorporate Gateway cloning attB sites at the ends of the fragments. The amplification products were purified from gel and cloned into pDONR221 donor vector (Invitrogen™) via standard Gateway BP reaction cloning (thermofisher).

The 2.0 kb promoter sequence upstream of the AtCHK2 gene (AT5G35750) was synthesized by gene synthesis (ThermoFisher Scientific). The synthesized fragment was PCR-amplified using forward primer 15_00083 and reverse primer 15_00084, and cloned into entry vector pENTR™ 5'-TOPO using the pENTR™ 5'-TOPO® TA Cloning® Kit (Invitrogen™).

Example 2: Cloning of the *Arabidopsis* CHK4 Gene

The coding sequence of the *Arabidopsis* CHK4 gene (AT2G01830) was amplified by PCR using CHK4 specific forward primer 14_04106 and reverse primer 14_04107 from *Arabidopsis thaliana* Col-0 genomic DNA as template. A second amplification was performed with primers 14_04114 (forward) and 14_04115 (reverse) to incorporate Gateway cloning attB sites at the ends of the fragments. The amplification products were purified from gel and cloned into pDONR221 donor vector (Invitrogen™) via standard Gateway BP reaction cloning thermofisher).

The 2.0 kb promoter sequence upstream of the AtCHK4 gene (AT2G01830) was synthesized by gene synthesis (ThermoFisher Scientific). The synthesized fragment was PCR-amplified using forward primer 15_00087 and reverse primer 15_00088, and cloned into entry vector pENTR™ 5'-TOPO using the pENTR™ 5'-TOPO® TA Cloning® Kit (Invitrogen™).

Example 3: Construction of Expression Constructs pKG9785 and pKG9791

An expression construct for the *Arabidopsis* CHK2 gene under control of its native 2 kb promoter was obtained by combining the CHK2 promoter fragment and the CHK2 coding sequence fragment from the entry vectors described in Example 1 into multisite Gateway destination vector pK7m24gw,3 through a single step LR cloning reaction (ThermoFisher).

An expression construct for the *Arabidopsis* CHK4 gene under control of its native 2 kb promoter was obtained by combining the CHK4 promoter fragment and the CHK4 coding sequence fragment from the entry vectors described in Example 2 into multisite Gateway destination vector pK7m24gw,3 through a single step LR cloning reaction (ThermoFisher).

The resulting plasmid constructs containing either CHK coding sequence under control of its native promoter were checked using restriction enzyme digestion with the combination NcoI and SacI, or the combination XbaI and HindIII, prior to transformation to *Agrobacterium tumefaciens* strain GV3101 via electroporation. The final constructs were named pKG9785 for the CHK2 expression cassette and pK9791 for the CHK4 expression cassette, respectively. Individual *Agrobacterium* colonies were selected and used in plant transformation to obtain transgenic lines.

Example 4: Transformation of *Arabidopsis*

Transgenic plants with stable integration of either CHK construct (pKG9785 or pKG9791) were obtained by transforming *Arabidopsis thaliana* Col-0 plants using the floral dip method according to the protocol of Clough and Bent (Plant J. 16 (6): 735-743, 1998). Positive transformants were obtained by sterilizing T1 progeny seed using vapor phase (Clough and Bent, 1998, Plant J. 16 (6): 735-743), germinating the seeds in vitro on 0.5MS10 culture medium (which is half strength MS medium according to Murashige and Skoog, 1962, Physiol. Plant. 15: 473-497 containing 100 g·L$^{-1}$ sucrose) supplemented with 50 mg·L$^{-1}$ kanamycin, and selecting kanamycin-resistant seedlings.

Multiple independent kanamycin-resistant seedlings for each construct were subsequently transferred to soil and selfed to obtain T2 seeds. Seeds were sterilized using vapor phase and sown on 0.5MS10 plates supplemented with 50 mg·L$^{-1}$ kanamycin. After two weeks, T3 lines of which the seedlings did not segregate for kanamycin resistance or sensitivity were considered homozygous and used in the regeneration assays. Expression levels of the transgenes in selected transgenic lines was checked by qRT-PCR using RNA extracted from whole in vitro seedlings and compared to the expression levels of the endogenous CHK genes in non-transformed Col-0 control plants. The primers used for qRT-PCR were 17_03894 (forward primer) and 17_03895 (reverse primer) for AtCHK4, and 17_03890 (forward) and 17_03891 (reverse) for AtCHK2. For each of constructs, homozygous plant lines were selected with a moderate to strong expression level to be tested for their regeneration capacity.

Example 5: Regeneration Assays of *Arabidopsis* Lines Expressing CHK Genes

The regeneration assays used are based on the shoot initiation assays described by To et al. (Plant Cell 16: 658-671, 2004, which incorporated herein by reference). *Arabidopsis* seedlings of the tested lines were grown on 0.5MS10 culture medium in square plates placed vertically in the dark for 3-4 days and then in dim light for 3 days to produce elongated and firm hypocotyls. Hypocotyls of around 7 mm in length were excised from the seedlings. Hypocotyl explants were transferred to MS medium (Murashige and Skoog, 1962, Physiol. Plant. 15: 473-497) with 1% (w/v) sucrose and 0.4% (w/v) phytagel containing kinetin (300 ng·mL$^{-1}$) and NAA (100 ng·mL$^{-1}$) and kept for 7 weeks at 25° C. at 16 h light/8 h dark. For each transgenic line 10 individual explants were tested in single square plates that also included five non-transformed (negative) control explants of *Arabidopsis* Col-0 and five explants of the *Arabidopsis* arr3,4,5,6,8,9 hextuple mutant serving as a positive control for regeneration. This mutant is known to regenerate at high efficiencies under these conditions (To et al., 2004, Plant Cell 16: 658-671). In each experiment four independent plates were assayed and the experiment was conducted in duplicate. Shoot regeneration rates were determined based on the number of inflorescence shoot that were formed after 7 weeks of growth.

Regeneration experiments were monitored, imaged and scored over seven weeks. All transgenic lines displayed enhanced regeneration in comparison to the control Col-0 line (Table 2). Regeneration efficiency was expressed as the percentage of explants displaying inflorescence shoot formation out of the total number of explants cultured. It is clear from Table 2 that the regeneration efficiency of plant material expressing CHK2 or CHK4 genes under control of their native promoters outperforms the regeneration efficiency of the positive control (hextuple arr mutant). Overall it is clear that enhanced expression of either CHK2 or CHK4 genes improves the regeneration capacity.

The percentage amino acid identity between CHK2, CHK3 and CHK4 is indicated in Table 3.

TABLE 1A

Sequences

| SEQ ID NO: | Sequence |
|---|---|
| 1 | Arabidopsis thaliana Nucleotide sequence CHK2 |
| 2 | Arabidopsis thaliana Nucleotide sequence CHK3 |
| 3 | Arabidopsis thaliana Nucleotide sequence CHK4 |
| 4 | Arabidopsis thaliana Amino acid sequence CHK2 |
| 5 | Arabidopsis thaliana Amino acid sequence CHK3 |
| 6 | Arabidopsis thaliana Amino acid sequence CHK4 |
| 7 | Arabidopsis thaliana Genomic sequence CHK2 |
| 8 | Arabidopsis thaliana Genomic sequence CHK3 |
| 9 | Arabidopsis thaliana Genomic sequence CHK4 |
| 10 | Arabidopsis thaliana promoter sequence CHK2 |
| 11 | Arabidopsis thaliana promoter sequence CHK3 |
| 12 | Arabidopsis thaliana promoter sequence CHK4 |
| 13 | Arabidopsis thaliana promoter sequence CHK2 with SNP |

TABLE 1B primer sequences

| SEQ ID NO: | Primer name | Sequence |
|---|---|---|
| 14 | pAtCHK2_F | TAATTTGAATATTTATATTCAATTTCATACATAT |
| 15 | pAtCHK2_R | TTCGACTCCTAATCTCAGATTCA |
| 16 | pAtCHK4_F | CCAATTCACGTTAAATCTATCTCTTG |
| 17 | pAtCHK4_R | CACTTCAAATGTAGGTATTCCATTTT |
| 18 | AtCHK2_F_CDS | ATGTCTATAACTTGTGAGCTCTTGAA |
| 19 | AtCHK2_R_CDS | TTAACAAGGTTCAAAGAATCTTGC |
| 20 | AtCHK2_F_CDS_attB1F | GGGGACAAGTTTGTACAAAAAAGCAGGCTATGTCTATAACTTGTGAGCTCTTGAA |
| 21 | AtCHK2_R_CDS_attB2R | GGGGACCACTTTGTACAAGAAAGCTGGGTTTAACAAGGTTCAAAGAATCTTGC |
| 22 | AtCHK4_F_CDS | ATGAGAAGAGATTTTGTGTATAATAATAATGC |
| 23 | AtCHK4_R_CDS | TTACGACGAAGGTGAGATAGGA |
| 24 | AtCHK4_F_CDS_attB1F | GGGGACAAGTTTGTACAAAAAAGCAGGCTATGAGAAGAGATTTTGTGTATAATAATAATGC |
| 25 | AtCHK4_R_CDS_attB2R | GGGGACCACTTTGTACAAGAAAGCTGGGTTACGACGAAGGTGAGATAGGA |
| 26 | Q_CHK4_F | TAAGCCTGTTAGAGCTGCTGTG |
| 27 | Q_CHK4_R | TCTTTCAAACGCAGCAGCTG |

TABLE 1B-continued primer sequences

| SEQ ID NO: | Primer name | Sequence |
| --- | --- | --- |
| 28 | Q_CHK2_F | GCTACAGAAGAACAGCGTGTTG |
| 29 | Q_CHK2_R | TGTTTGCTGGCAAGTTGGTG |

TABLE 2

Regeneration efficiencies of Arabidopsis hypocotyl explants expressing CHK alleles on medium with kinetin and NAA

| Type of CHK alleles | # explants | # regener. | % regener. |
| --- | --- | --- | --- |
| Effect of CHK alleles | | | |
| AtCHK2 (pKG9785) | 79 | 40 | 50.6 |
| AtCHK4 (pKG9791) | 68 | 43 | 63.2 |
| Controls | | | |
| Arabidopsis arr3,4,5,6,8,9 hextuple mutant | 360 | 160 | 44.4 |
| Col-0 negative control | 360 | 7 | 1.9 |

TABLE 3

Percentage amino acid sequence identity between CHK2, CHK3 and CHK4

| | CHK2 | CHK3 | CHK4 |
| --- | --- | --- | --- |
| CHK2 | 100% | 58% | 54% |
| CHK3 | | 100% | 53% |
| CHK4 | | | 100% |

Example 6: Identifying the Tomato CHK2 Orthologue

An orthology search was carried out with a query of the AtCHK2 and AtCHK4 genes (AT5G35750 and AT2G0183) in 15 plant proteome databases using multiple protein sequence alignment software JackHMMER (http://hmmer.org, version 3.2.1; June 2018; Johnson et al., BMC Bioinformatics, 11: 431, 2010, doi: 10.1186/1471-2105-11-431). JackHMMER blast searches were supplemented with a MEME Suite motif-based sequence analysis (http://meme-suite.org/index.html; Meme Suite 4.12.0., June 2017; Bailey et al., Nucl. Acids Res. 37: W2302-W208, 2009, doi.org/10.1093/nar/gkp335) to identify and visualize known protein domains. The orthology search revealed single candidate genes in the tomato genome for both AtCHK2 and AtCHK4 genes as queries, with amino acid identities of >50%. These tomato genes are Solyc07g047770 (SlyCHK2) and Solyc07g008110 (SlyCHK4) as most likely homologs of AtCHK2 and AtCHK4, respectively. Solyc07g047770 (SlyCHK2) was selected for further work.

Example 7: Construction of a Tomato CHK Expression Cassette

A functional expression cassette of SlyCHK2 containing 2 kb of its native promoter sequence was designed in silico. The nopaline synthase terminator and Gateway adapters were appended to the sequence to create a cloning fragment for direct cloning in a Gateway destination vector. The synthesis of the cassette was ordered from GeneART (www.thermofisher.com). The full sequence of the cassette is given in SEQ ID NO: 32. The fragment was introduced in Gateway binary destination vector pKm43GW (Karimi et al., Plant Physiol. 145: 1144-1154, 2007, doi.org/10.1104/pp.107.106989) through a single step LR cloning reaction (www.thermofisher.com). pKm43GW is a Gateway multi-site binary destination vector containing streptomycin and spectinomycin resistance markers for bacterial selection, and an nptII gene for selection of plant tissue on kanamycin. The resulting plasmid construct was named pKG10867 and was cloned in E. coli and checked by restriction enzyme digestion using the combination EcoRV and NheI. Miniprep plasmid DNA was electroporated to Agrobacterium tumefaciens strain GV3101.

Example 8: Tomato Transformation

The SlyCHK2 under its native promoter was introduced into tomato cultivar Moneyberg-Plus (TMV-resistant) by Agrobacterium-mediated transformation. Approximately 50 tomato seeds were sterilized and germinated on ½ MS10 medium for 11 days. Cotyledon explants from the seedlings were dissected and precultured for 24 h on 2N1B medium (=M520 medium containing 2 mg·l$^{-1}$ NAA and 1 mg·l$^{-1}$ BAP) supplemented with 40 µg·l$^{-1}$ acetosyringone. The explants were submerged in a suspension of Agrobacterium tumefaciens GV3101 carrying pKG10867 grown overnight in TY medium containing 20 mg·l$^{-1}$ streptomycin and 50 mg·l$^{-1}$ spectinomycin, and diluted to OD$_{600}$ 0.138. The explants were blotted dry and cocultivated for 2 days on 2N1B plates with 40 µg·l$^{-1}$ acetosyringone. Subsequently, the explants were transferred to selective medium MS20ZVCK consisting of MS20 medium with 1 mg·l$^{-1}$ zeatin, 200 mg·l$^{-1}$ vancomycin, 200 mg·l$^{-1}$ cefotaxim and 100 mg·l$^{-1}$ kanamycin and cultivated at 25° C. and 3000 lux (16/8 h photoperiod) in a growth chamber. The explants were subcultured every 3 weeks onto fresh medium. When callus had formed on the selective medium, the callus was subcultered and the original explants were discarded.

Example 9: Recording Transformation Efficiencies

Tomato callus subcultured every 3 weeks onto fresh medium MS20ZCVK started to produce shoot meristems and shoots from day 114 of the experiment. Shoots over 5 mm in length were taken off the calli, and transferred to rooting medium consisting of MS20 without any additions. The accumulated number of shoots harvested in this way was recorded (Table 4) and compared to similarly cultivated tomato Moneyberg cotyledon explants that had not been contacted with *Agrobacterium tumefaciens* and were grown on medium without kanamycin. It is clear that shoots harvested from kanamycin-resistant callus after pKG10867-transformation appear in larger numbers and faster than shoots regenerating from control tomato explants. This effect is attributed to the ectopic expression of the SlyCHK2 gene.

TABLE 4

Shoot regeneration efficiencies of tomato Moneyberg cotyledon explants transformed with SlyCHK2 (pKG10867), recorded as the cumulative number of shoots harvested from transformed calli over time.

| | # | day 114 | day 136 | day 156 | day 183 |
|---|---|---|---|---|---|
| Moneyberg pKG10867 | 200 | 1 | 26 | 47 | 93 |
| Moneyberg control | 200 | 1 | 7 | 29 | 64 |

The invention claimed is:

1. A method for improving cytokinin-induced de novo shoot formation of a plant cell, comprising:
    (a) increasing or introducing expression of at least one a histidine kinase in the plant cell;
    (b) inducing de novo formation of a number of shoots and elongation of the number of shoots by exposing the plant cell of (a) to a cytokinin-comprising medium;
    (c) dissecting a de novo formed shoot; and
    (d) inducing root formation of the dissected shoot, wherein the number of de novo formed shoots is increased as compared to an identical cell not having an increased or introduced expression of the histidine kinase, and wherein the histidine kinase has at least 80% sequence identity with SEQ ID NO: 31.

2. The method according to claim 1, wherein the amino acid sequence of the histidine kinase has at least 90% sequence identity with SEQ ID NO: 31.

3. The method according to claim 1, wherein the amino acid sequence of the histidine kinase has at least 95% sequence identity with SEQ ID NO: 31.

4. The method according to claim 1, wherein the histidine kinase is encoded by a nucleotide sequence having at least 50% sequence identity with SEQ ID NO: 30.

5. The method according to claim 1, wherein the expression of the histidine kinase is transiently increased or introduced into the plant cell.

6. The method according to claim 1, wherein the expression of the histidine kinase is continuously increased or introduced in the plant cell.

7. The method according to claim 1, wherein the plant cell is from a plant selected from the group consisting of barley, cabbage, canola, cassava, cauliflower, chicory, cotton, cucumber, eggplant, grape, hot pepper, lettuce, maize, melon, oilseed rape, potato, pumpkin, rice, rye, *sorghum*, squash, sugar cane, sugar beet, sunflower, sweet pepper, tomato, water melon, wheat, zucchini, soybean, *chrysanthemum* and *Arabidopsis*.

8. The method according to claim 1, wherein the cytokinin is an adenine-type cytokinin.

9. The method according to claim 8, wherein the adenine-type cytokinin is selected from the group consisting of kinetin, zeatin, trans-zeatin, cis-zeatin, dihydrozeatin, 6-benzylaminopurine and 2iP.

10. The method according to claim 1, further comprising:
    (a) incubating the plant cell having increased or introduced expression of the histidine kinase in the medium comprising a cytokinin plant hormone; and
    (b) allowing the plant cell to regenerate into a plant.

11. The method according to claim 5, wherein the medium comprises at least one further plant hormone.

12. The method according to claim 11, wherein the one further plant hormone is an auxin.

13. The method according to claim 10, wherein the plant cell is part of at least one of a multicellular tissue, a callus tissue, a plant organ, an explant, a hypocotyl explant, a stem explant, a cotyledon explant, a root explant, a leaf explant, a flower explant and a meristematic tissue.

14. A method according to claim 10, wherein the concentration of cytokinin in the medium is 100-3000 ng/ml.

15. The method according to claim 14, wherein the concentration of cytokinin in the medium is 200-600 ng/ml.

16. The method according to claim 1, wherein the plant cell is incubated in a medium comprising a cytokinin for at least 5 weeks prior to dissecting a de novo formed shoot.

17. The method according to claim 1, wherein the plant cell is a plant cell of a recalcitrant plant.

* * * * *